(12) United States Patent
Garcia-Barcelo et al.

(10) Patent No.: US 7,198,898 B2
(45) Date of Patent: Apr. 3, 2007

(54) PHOX2B POLYMORPHISMS AS HIRSCHSPRUNG'S DISEASE DIAGNOSTIC MARKERS AND METHODS BASED THEREON

(75) Inventors: Maria Mercedes Garcia-Barcelo, Hong Kong (HK); Mai Har Sham, Hong Kong (HK); Paul Kwong Hang Tam, Aberdeen (HK); Vincent Chi Hang Lui, Hong Kong (HK); Benedict Ling Sze Chen, New Territories (HK)

(73) Assignee: The University of Hong Kong, Hong Kong (HK)

( * ) Notice: Subject to any disclaimer, the term of this patent is extended or adjusted under 35 U.S.C. 154(b) by 404 days.

(21) Appl. No.: 10/408,501

(22) Filed: Apr. 7, 2003

(65) Prior Publication Data

US 2003/0224424 A1    Dec. 4, 2003

Related U.S. Application Data

(60) Provisional application No. 60/370,968, filed on Apr. 8, 2002.

(51) Int. Cl.
*C12Q 1/68* (2006.01)
*C12P 19/34* (2006.01)

(52) U.S. Cl. .......................................... 435/6; 435/91.2
(58) Field of Classification Search ................ None
See application file for complete search history.

(56) References Cited

OTHER PUBLICATIONS

Yokoyama et al (1999), Genomics 59, pp. 40-50.*
Amiel et al (2001), Journal of Medical Genetics 38, pp. 729-739.*
Hofstra et al (1997) European journal of Human Genetics 5, pp. 180-185.*
Parisi et al (2000) Current Opinions in Pediatrics 12, pp. 610-617.*
Pattyn et al (1999) Nature 399, pp. 366-370.*
Gaultier et al (2005) Pediatric Research, vol. 58, No. 1, pp. 1-5.*
By Andrew Chin, "On the preparation and utilization of isolated and purified oligonucleotides", published Mar. 14, 2002 at Kathrine R. Everett Law Library of the University of North Carolina (submitted herewith in a form of CD-ROM and a partial written description (2 pages) from the CD-ROM).

* cited by examiner

*Primary Examiner*—Juliet C. Switzer
*Assistant Examiner*—Stephen Kapushoc
(74) *Attorney, Agent, or Firm*—Dickstein Shapiro LLP

(57) ABSTRACT

The invention relates generally to polymorphisms or mutations of the PHOX2B gene. More particularly, the invention relates to polymorphisms or mutations of the PHOX2B gene that are responsible for the disease Hirschsprung's disease (HSCR), which is a neural crest-associated developmental disorder. Specifically, the invention relates to the detection of a single base-pair polymorphism in the PHOX2B gene that is associated with HSCR. The invention also relates to methods and kits for screening for carriers of mutations of the PHOX2B gene and the diagnosis of increased risk of HSCR. The invention further relates to diagnosing predisposition or susceptibility to increased risk of developing HSCR by screening for the presence of a polymorphism associated with HSCR. The invention also relates to compositions for screening for the polymorphism and treatment choices for patients having the polymorphism of the present invention. The invention further relates to providing polymorphisms in the PHOX2B gene for forensic use and in paternity test. The invention also relates to screening assays and therapeutic and prophylactic methods.

5 Claims, 18 Drawing Sheets

Figure 1A

Figure 5:
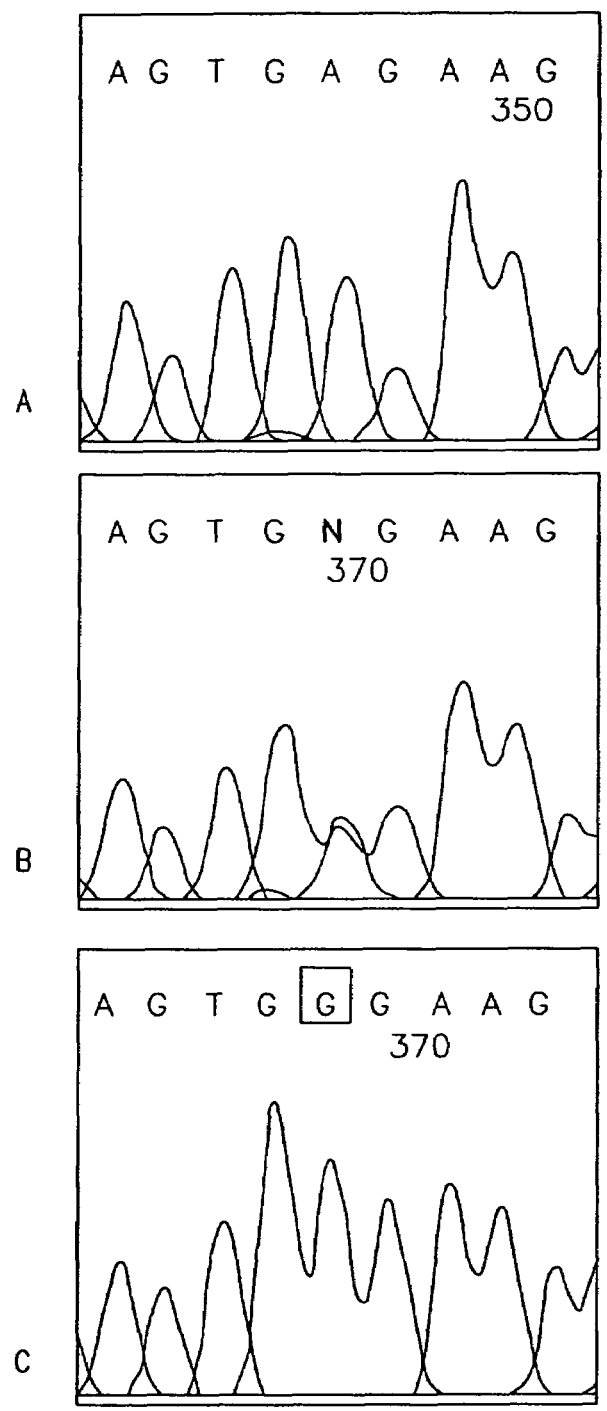

```
   1 cctgagtctc ttgaaagcac atttagctgc aagaagaaat gcaatttata agatgctttc
  61 tctctgtctc tctttgtttt taacccctc taaccaggtg tatttttaaa gaaatccgct
 121 tatcgttcac ataaacccc ttggcccact tactctatgt tacagggcgc ctgagtcttg
 181 ccaatgtccc agtcctttat aacatttcat gcacttcggg gggtaggctt gttgttaaat
 241 tgagcgtgta acactcttac aaaacaggtt ttctatgaca tcaaggtttc ttctccctaa
 301 ccgaggggga aaaaagaag aggacgaaga aggggaaaa cacacacact atctcaattt
 361 atgcctaagg tatatgatca gttaaaaagg cttaaaagct cggggaaatt ggatcaggga
 421 gaatcgtcac ccaactttca ttatttccaa gtagtgtgat tgaattaaag ggcagggagc
 481 tggttagaag ggaggatcag gggctcggtg cgtaatggtg tggtattaaa ttctaattag
 541 agatgcagga atcaatgata gggaggttgg acagctcagt tccccagtgc cagcccaata
 601 gacggatgag ttattgtcat gtaaaaagcg ccagcaataa gaccaaccgc tttgctattg
 661 tccaagtgga aagagccaag tttattatga ggactatatg ctctagagac ctcagacaag
 721 gcatctcata ggaggctttt tcataaaact aggctctgct ggtagtaagg aggccagttt
 781 ggaggcaggc gttgagctgt gcacatctcc ccactccagc caccttctcc atatccatct
 841 tttatttcat ttttccactt ggctgagcca tccagaacct tttcaatgta taaaatggaa
 901 tattcttacc tcaattcctc tgcctacgag tcctgtatgg ctgggatgga cacctcgagc
 961 ctggcttcag cctatgctga cttcagttcc tgcagccagg ccagtggctt ccagtataac
1021 ccgataagga ccacttttgg ggccacgtcc ggctgccctt ccctcacgcc gggatcctgc
1081 agcctgggca ccctcaggga ccaccagagc agtccgtacg ccgcaggtta ggaccttcag
1141 ctttctcagc ggaggaagcc gcctttccgc ccgtatatag aagccttga ttgcatttga
1201 aaatggaaat gtgtttagta tttaccaaac gaaatttgct tacacaaatg aaagaattta
1261 tcacgtttga agcgattgca gggaggggta attcacttac agggttacac tatcctagtc
1321 acacccgaac cgcccacaaa attatcttaa gctgccaaaa tgataggcat aatttattta
1381 ctttgcgatg agacgtatag cttagaaaat aattgaatta caaagagtaa agctcattac
1441 tggcagtgtc tcttttttta agaaccgaga gcggctcaca cttcttgggc tggtcatttt
1501 tatgattatt tctttaattt attattattt ttttgcagct cttcccccca acttttgagc
1561 cgggtcaact ttctgagaat tgaaaagttc ccaaagtggg actgtttggt aacttctttc
1621 cctggctccc ctgatattcc gactgatgtt ttgggatttt tttcctctct ggttttttcc
1681 tgctgaaagc actatctcaa gtccgtcaca tcgcgctgtt tcaatccacc caaaggcgct
1741 tgtgccagaa aggactccgc caagcccgaa gtttgagccc aggtttccgc agataacaaa
```

Figure 1A Cont'd

```
1801  tttcctcggt ttcttcccgc agcttctctc ggcaactctc tcgcgcgggt gtaggtagcg
1861  gctgccgtat gacctgacct tggagtcctc acattctagc tccacggccg gcgagctgcc
1921  ggctgatttg ctcactttct gtctcctctg tcatactcta gttccttaca aactcttcac
1981  ggaccacggc ggcctcaacg agaagcgcaa gcagcggcgc atccgcacca ctttcaccag
2041  tgcccagctc aaagagctgg aaagggtctt cgcggagact cactaccccg acatctacac
2101  tcgggaggag ctggccctga agatcgacct cacagaggcg cgagtccagg tacgcgcgcc
2161  tggaaaccga ccccgctccg ccgcactggt ccggggaggt gtggggtgag gggcggctgg
2221  tgaaattcga agtcctggag cctcgagtga aaggaccta gggccccatg gccgatcaga
2281  aatactggat ttggtgtggc tgtgcgttcg agagaggctt agagcgcacg ctcttggcat
2341  tttatttaca gttgcgaagt gtttcccacc cgagcagaga catgggggc cttgggacgt
2401  ggatgagcga tgcaatttcg gggacaggaa gtgcctgtgg tggaaggtgt gcagactttg
2461  ctcccgtatt ataagttttt ccttctcccc tcccgccccc caaaaaaatg cctcctaact
2521  caagtgcttt taacctggcc ccatggcata taggttcatt ttcccggaaa ctgtgacttg
2581  cattagattt gcaaagggtc tgtgacttca tgaaggtcaa gaaccatgac ttactccaac
2641  ctgttaaaca caggtgcgct cacgagttgg ccacagcgcc ttttgggtg agcccccgac
2701  cgagaagcgg tgcgcaccat tgcacgcttt tccaggctca aaggccgggg atgggcagcg
2761  gagcaaaccc agagaggatc ccttttcctt ttaccaatta gagtttaact ttagaactta
2821  ggcttagggg tgaatggcga gctcggggct tgctcaagaa gccgactgaa cagaggccca
2881  ccaaaataag gccttccctt ttcgggtctt tctgggacct gcggcttttt aaactctgcc
2941  gcaagccttc atgtccctgg cgtgctcact cccctaaga aagtttctcc gaaaatgcac
3001  agcaataaga agcggtagac ttggtggatg tgcgcgcggg ggtgatcaca gcgcatgggg
3061  aggagggtgt taaaacaagc cgaagtagaa cttgggccac cctaaccggt gcttttcttt
3121  cccatttct tctttctccc cctgcttcac cgtctctcct tccgtcttgg gccaggtgtg
3181  gttccagaac cgccgcgcca agtttcgcaa gcaggagcgc gcagcggcag ccgcagcggc
3241  cgcggccaag aacggctcct cgggcaaaaa gtctgactct tccagggacg acgagagcaa
3301  agaggccaag agcactgacc cggacagcac tggggccca ggtcccaatc caacccccac
3361  ccccagctgc ggggcgaatg gaggcggcgg cggcgggccc agccggctg gagctccggg
3421  ggcggcgggg cccgggggcc cgggaggcga acccggcaag ggcggcgcag cagcagcggc
3481  ggcggccgcg gcagcggcgg cggcggcagc ggcagcggcg gcagctggag gcctggctgc
3541  ggctggggc cctggacaag gctgggctcc cggccccggc ccatcacct catcccgga
3601  ttcgcttggg ggtcccttcg gcagcgtcct atcttcgctc caaagaccca acggtgccaa
3661  agccgcctta gtgaagagca gtatgttctg atctggaatc ctgcggcggc ggcggcggcg
3721  gcgacagcgg gcgagccagg gcccgggcgg gcgagtgggc gagcgggtag gcccaaggct
3781  attgtcgtcg ctgctgccat ggcttttca ttgagggcct aaagtaatcg cgctaagaat
3841  aaagggaaaa cggcgtcgcc ctcatttcaa ccccactcct acccccttcc tcaacccca
```

Figure 1A Cont'd

```
3901 aacaaaacaa acaaacttcc ctggcttcgc acctgcctgg ggcctcgcag cggggccagg
3961 gctccgcctg ctgatcgggg gttgtgagca gcgcggcctg gacgcggggc actctcaggg
4021 ggctgtgtct gcgtgtcagt ttgtgtctgt ctcggggaat gtgtgtctgt ggcccaagca
4081 ggtgacagga agagatgggg ggcctcaacc aacttagtga cttgtttaga aaaaaaagac
4141 aaaaagtaa aataaaaac aaaaagttg gaaggcagaa accattaaaa aacaaaaagc
4201 caacaaccca gaaaggttta aaaaacataa ggaaaaaaaa gacaaattaa aggaggggct
4261 aggggagaag ctgcagctgg agctgaaggc tcgatcttgt gaacccctaa atccgctccc
4321 tcctaacagc acggattctc ttggggctct tcttcaggga agagtaggga cgccgttcca
4381 gccccccttc ctatcgtgtc cttgggttcg ggtcactgcg gcgacgactt gctcagactg
4441 tcccggcggc cggagtgact ttctcgcacc cccttgcctg tccacctcg ctgaacacca
4501 tcccgccatt agcgcatcgg aacccacac agttgcaact cccaacccg aatctttgca
4561 gccgttcggc cctgaaagat gccctatcca tgagatgcct tttcatctgc aaactctgca
4621 aaatgtgtct catgtttcgc aactctttt ttcccctcg ctcccgccta ccccgtcggc
4681 attttcttct tccaccagct tttactgaac tttttggcac tgctttggat tggggtcaat
4741 tgcagtccac gtaactggct gcagagaaat ctaccgagca aggaaaaggc acacacacac
4801 gtttgcaggg gtgtctcggt ttgcatttct gttggaatga tccgaactgg actcacatcc
4861 tgtatggtgg atggactgta tattgagggt tccattcttc gcgcagttta gacatctctg
4921 ttttgattct ttgttgttgt ttttatttta aaaggcacaa actctagata ttagttgaat
4981 gttgaggctt taactttttc ggtgtctttc tacaactgtg ttctgtgact caattgtatc
5041 gtgttaatat cagtgcagac tgtctcctct acgtgaccgt ataatgtttt tctcgtcttg
5101 tagtctctat ggcgtgtctt tatggtgtaa taaggttctc acggggtcaa tcttttgtgt
5161 ttagagaggc cacggttcag acaatggtat atattttgt tatcaggtgc atgtctgtct
5221 gatttctttt tttttcctgt tggactatgt ttgtgaacat aattgtcata agttatgttt
5281 cagatttttg aatttattta tatgtgttat aatgaatgct tctatttaaa agggaaatat
5341 ttctacatgt gcttatagtt ttccaagagt gtaccattaa cttgattgtt gataataaaa
5401 accaaaagca agtctagcaa ttgaactctc ctttttcttg attctttttt tttttttttt
5461 tttgggttgg tcattgtttt tttttttaa gttttttttt aaaaggat
```

Figure 1B

```
  1  mykmeysyln  ssayescmag  mdtsslasay  adfsscsqas  gfgynpirtt  fgatsgcpsl
 61  tpgscslgtl  rdhqsspyaa  vpyklftdhg  glnekrkqrr  irttftsaql  kelervfaet
121  hypdiytree  lalkidltea  rvquwfqnrr  akfrkgeraa  aaaaaaakng  ssgkksdssr
181  ddeskeakst  dpdstggpgp  npnptpscga  nggggggpsp  agapgaagpg  gpggepgkgg
241  aaaaaaaaaa  aaaaaaaaaa  gglaaaggpg  qgwapgpgpi  tsipdslggp  fgsvlsslqr
301  pngakaalvk  ssmf
```

Figure 2

```
   1 cctgagtctc ttgaaagcac atttagctgc aagaagaaat gcaatttata agatgctttc
  61 tctctgtctc tctttgtttt taaccccctc taaccaggtg tatttttaaa gaaatccgct
 121 tatcgttcac ataaaccccc ttggcccact tactctatgt tacagggcgc ctgagtcttg
 181 ccaatgtccc agtcctttat aacatttcat gcacttcggg gggtaggctt gttgttaaat
 241 tgagcgtgta acactcttac aaaacaggtt ttctatgaca tcaaggtttc ttctccctaa
 301 ccgaggggga aaaaagaag aggacgaaga aggggaaaa cacacacact atctcaattt
 361 atgcctaagg tatatgatca gttaaaaagg cttaaaagct cggggaaatt ggatcaggga
 421 gaatcgtcac ccaactttca ttatttccaa gtagtgtgat tgaattaaag ggcagggagc
 481 tggttagaag ggaggatcag gggctcggtg cgtaatggtg tggtattaaa ttctaattag
 541 agatgcagga atcaatgata gggaggttgg acagctcagt tccccagtgc cagcccaata
 601 gacggatgag ttattgtcat gtaaaaagcg ccagcaataa gaccaaccgc tttgctattg
 661 tccaagtgga aagagccaag tttattatga ggactatatg ctctagagac ctcagacaag
 721 gcatctcata ggaggctttt tcataaaact aggctctgct ggtagtaagg aggccagttt
 781 ggaggcaggc gttgagctgt gcacatctcc ccactccagc caccttctcc atatccatct
 841 tttatttcat ttttccactt ggctgagcca tccagaacct tttcaatgta taaaatggaa
 901 tattcttacc tcaattcctc tgcctacgag tcctgtatgg ctgggatgga cacctcgagc
 961 ctggcttcag cctatgctga cttcagttcc tgcagccagg ccagtggctt ccagtataac
1021 ccgataagga ccactttttgg ggccacgtcc ggctgcccctt ccctcacgcc gggatcctgc
1081 agcctgggca ccctcaggga ccaccagagc agtccgtacg ccgcaggtta ggaccttcag
1141 ctttctcagc ggaggaagcc gcctttccgc ccgtatatag gaagccttga ttgcatttga
1201 aaatggaaat gtgtttagta tttaccaaac gaaatttgct tacacaaatg aaagaattta
1261 tcacgtttga agcgattgca gggaggggta attcacttac agggttacac tatcctagtc
1321 acacccgaac cgcccacaaa attatcttaa gctgccaaaa tgataggcat aatttattta
1381 ctttgcgatg agacgtatag cttagaaaat aattgaatta caaagagtaa agctcattac
1441 tggcagtgtc tcttttttta agaaccgaga gcggctcaca cttcttgggc tggtcatttt
1501 tatgattatt tctttaattt attattattt ttttgcagct ctttccccca actttttgagc
```

Figure 2 Cont'd

```
1561  cgggtcaact ttctgagaat tgaaaagttc ccaaagtggg actgtttggt aacttctttc
1621  cctggctccc ctgatattcc gactgatgtt ttgggatttt tttcctctct ggttttttcc
1681  tgctgaaagc actatctcaa gtccgtcaca tcgcgctgtt tcaatccacc caaaggcgct
1741  tgtgccagaa aggactccgc caagcccgaa gtttgagccc aggtttccgc agataacaaa
1801  tttcctcggt ttcttcccgc agcttctctc ggcaactctc tcgcgcgggt gtaggtagcg
1861  gctgccgtat gacctgacct tggagtcctc acattctagc tccacggccg gcgagctgcc
1921  ggctgatttg ctcactttct gtctcctctg tcatactcta gttccttaca aactcttcac
1981  ggaccacggc ggcctcaacg agaagcgcaa gcagcggcgc atccgcacca ctttcaccag
2041  tgcccagctc aaagagctgg aaagggtctt cgcggagact cactacccg acatctacac
2101  tcgggaggag ctggccctga agatcgacct cacagaggcg cgagtccagg tacgcgcgcc
2161  tggaaaccga ccccgctccg ccgcactggt ccggggaggt gtggggtgag ggcggctgg
2221  tgaaattcga agtcctggag cctcgagtgg aaggaccta gggccccatg gccgatcaga
2281  aatactggat ttggtgtggc tgtgcgttcg agagaggctt agagcgcacg ctcttggcat
2341  tttatttaca gttgcgaagt gtttcccacc cgagcagaga catgggggc cttgggacgt
2401  ggatgagcga tgcaatttcg gggacaggaa gtgcctgtgg tggaaggtgt gcagactttg
2461  ctcccgtatt ataagttttt ccttctcccc tcccgccccc caaaaaaatg cctcctaact
2521  caagtgcttt taacctggcc ccatggcata taggttcatt ttcccggaaa ctgtgacttg
2581  cattagattt gcaaagggtc tgtgacttca tgaaggtcaa gaaccatgac ttactccaac
2641  ctgttaaaca caggtgcgct cacgagttgg ccacagcgcc ttttgggtg agcccccgac
2701  cgagaagcgg tgcgcaccat tgcacgcttt tccaggctca aaggccgggg atgggcagcg
2761  gagcaaaccc agagaggatc ccttttcctt ttaccaatta gagtttaact ttagaactta
2821  ggcttagggg tgaatggcga gctcggggct tgctcaagaa gccgactgaa cagaggccca
2881  ccaaaataag gccttccctt ttcgggtctt tctgggacct gcggcttttt aaactctgcc
2941  gcaagccttc atgtccctgg cgtgctcact ccccctaaga aagtttctcc gaaaatgcac
3001  agcaataaga agcggtagac ttggtggatg tgcgcgcggg ggtgatcaca gcgcatgggg
3061  aggagggtgt taaaacaagc cgaagtagaa cttgggccac cctaaccggt gcttttcttt
3121  cccatttct tctttctccc cctgcttcac cgtctctcct tccgtcttgg gccaggtgtg
3181  gttccagaac cgccgcgcca agtttcgcaa gcaggagcgc gcagcggcag ccgcagcggc
3241  cgcggccaag aacggctcct cgggcaaaaa gtctgactct tccagggacg acgagagcaa
3301  agaggccaag agcactgacc cggacagcac tggggcccca ggtcccaatc caaccccac
3361  ccccagctgc ggggcgaatg gaggcggcgg cggcgggccc agcccggctg gagctccggg
3421  ggcggcgggg cccgggggcc cggaggcga accggcaag ggcggcgcag cagcagcggc
3481  ggcggccgcg gcagcggcgg cggcggcagc ggcagcggcg gcagctggag gcctggctgc
3541  ggctgggggc cctggacaag gctgggctcc cggccccggc ccatcacct ccatcccgga
3601  ttcgcttggg ggtcccttcg gcagcgtcct atcttcgctc caaagaccca acggtgccaa
```

Figure 2 Cont'd

```
3661 agccgcctta gtgaagagca gtatgttctg atctggaatc ctgcggcggc ggcggcggcg
3721 gcgacagcgg gcgagccagg gcccgggcgg gcgagtgggc gagcgggtag gcccaaggct
3781 attgtcgtcg ctgctgccat ggcttttttca ttgagggcct aaagtaatcg cgctaagaat
3841 aaagggaaaa cggcgtcgcc ctcatttcaa ccccactcct accccttcc tcaaccccca
3901 aacaaaacaa acaaacttcc ctggcttcgc acctgcctgg ggcctcgcag cggggccagg
3961 gctccgcctg ctgatcgggg gttgtgagca gcgcggcctg gacgcggggc actctcaggg
4021 ggctgtgtct gcgtgtcagt ttgtgtctgt ctcggggaat gtgtgtctgt ggcccaagca
4081 ggtgacagga agagatgggg ggcctcaacc aacttagtga cttgtttaga aaaaaaagac
4141 aaaaagtaa aataaaaac aaaaagttg gaaggcagaa accattaaaa aacaaaaagc
4201 caacaaccca gaaaggttta aaaaacataa ggaaaaaaaa gacaaattaa aggaggggct
4261 aggggagaag ctgcagctgg agctgaaggc tcgatcttgt gaaccctaa atccgctccc
4321 tcctaacagc acggattctc ttggggctct tcttcaggga agagtaggga cgccgttcca
4381 gccccccttc ctatcgtgtc cttgggttcg ggtcactgcg gcgacgactt gctcagactg
4441 tcccggcggc cggagtgact ttctcgcacc cccttgcctg tcccacctcg ctgaacacca
4501 tcccgccatt agcgcatcgg aaccccacac agttgcaact cccaaccccg aatctttgca
4561 gccgttcggc cctgaaagat gccctatcca tgagatgcct tttcatctgc aaactctgca
4621 aaatgtgtct catgtttcgc aactcttttt ttcccccctcg ctcccgccta ccccgtcggc
4681 atttttcttct tccaccagct tttactgaac tttttggcac tgctttggat tggggtcaat
4741 tgcagtccac gtaactggct gcagagaaat ctaccgagca aggaaaaggc acacacacac
4801 gtttgcaggg gtgtctcggt ttgcatttct gttggaatga tccgaactgg actcacatcc
4861 tgtatggtgg atggactgta tattgagggt tccattcttc gcgcagttta gacatctctg
4921 ttttgattct ttgttgttgt ttttatttta aaaggcacaa actctagata ttagttgaat
4981 gttgaggctt taactttttc ggtgtctttc tacaactgtg ttctgtgact caattgtatc
5041 gtgttaatat cagtgcagac tgtctcctct acgtgaccgt ataatgtttt tctcgtcttg
5101 tagtctctat ggcgtgtctt tatggtgtaa taaggttctc acggggtcaa tcttttgtgt
5161 ttagagaggc cacggttcag acaatggtat atattttgt tatcaggtgc atgtctgtct
5221 gatttctttt ttttccctgt tggactatgt ttgtgaacat aattgtcata agttatgttt
5281 cagattttg aatttattta tatgtgttat aatgaatgct tctatttaaa agggaaatat
5341 ttctacatgt gcttatagtt ttccaagagt gtaccattaa cttgattgtt gataataaaa
5401 accaaaagca agtctagcaa ttgaactctt cttttcttg attctttttt ttttttttt
5461 tttgggttgg tcattgtttt tttttttaa gtttttttt aaaaggat
```

Figure 3

```
   1 cctgagtctc ttgaaagcac atttagctgc aagaagaaat gcaatttata agatgctttc
  61 tctctgtctc tctttgtttt taaccccctc taaccaggtg tatttttaaa gaaatccgct
 121 tatcgttcac ataaaccccc ttggcccact tactctatgt tacagggcgc ctgagtcttg
 181 ccaatgtccc agtcctttat aacatttcat gcacttcggg gggtaggctt gttgttaaat
 241 tgagcgtgta acactcttac aaaacaggtt ttctatgaca tcaaggtttc ttctccctaa
 301 ccgaggggga aaaaagaag aggacgaaga aggggaaaa cacacacact atctcaattt
 361 atgcctaagg tatatgatca gttaaaaagg cttaaaagct cggggaaatt ggatcaggga
 421 gaatcgtcac ccaactttca ttatttccaa gtagtgtgat tgaattaaag ggcagggagc
 481 tggttagaag ggaggatcag gggctcggtg cgtaatggtg tggtattaaa ttctaattag
 541 agatgcagga atcaatgata gggaggttgg acagctcagt tccccagtgc cagcccaata
 601 gacggatgag ttattgtcat gtaaaaagcg ccagcaataa gaccaaccgc tttgctattg
 661 tccaagtgga aagagccaag tttattatga ggactatatg ctctagagac ctcagacaag
 721 gcatctcata ggaggctttt tcataaaact aggctctgct ggtagtaagg aggccagttt
 781 ggaggcaggc gttgagctgt gcacatctcc ccactccagc caccttctcc atatccatct
 841 tttatttcat ttttccactt ggctgagcca tccagaacct tttcaatgta taaatggaa
 901 tattcttacc tcaattcctc tgcctacgag tcctgtatgg ctgggatgga cacctcgagc
 961 ctggcttcag cctatgctga cttcagttcc tgcagccagg ccagtggctt ccagtataac
1021 ccgataagga ccacttttgg ggccacgtcc ggctgccctt ccctcacgcc gggatcctgc
1081 agcctgggca ccctcaggga ccaccagagc agtccgtacg ccgcaggtta ggaccttcag
1141 ctttctcagc ggaggaagcc gcctttccgc ccgtatatag gaagccttga ttgcatttga
1201 aaatggaaat gtgtttagta tttaccaaac gaaatttgct tacacaaatg aaagaattta
1261 tcacgtttga agcgattgca gggaggggta attcacttac agggttacac tatcctagtc
1321 acacccgaac cgcccacaaa attatcttaa gctgccaaaa tgataggcat aatttattta
1381 ctttgcgatg agacgtatag cttagaaaat aattgaatta caaagagtaa agctcattac
1441 tggcagtgtc tctttttta agaaccgaga gcggctcaca cttcttgggc tggtcatttt
1501 tatgattatt tctttaattt attattattt ttttgcagct ctttccccca acttttgagc
1561 cgggtcaact ttctgagaat tgaaaagttc ccaaagtggg actgtttggt aacttctttc
1621 cctggctccc ctgatattcc gactgatgtt ttgggatttt tttcctctct ggttttttcc
1681 tgctgaaagc actatctcaa gtccgtcaca tcgcgctgtt tcaatccacc caaaggcgct
1741 tgtgccagaa aggactccgc caagcccgaa gtttgagccc aggtttccgc agataacaaa
```

Figure 3 Cont'd

```
1801 tttcctcggt ttcttcccgc agcttctctc ggcaactctc tcgcgcgggt gtaggtagcg
1861 gctgccgtat gacctgacct tggagtcctc acattctagc tccacggccg gcgagctgcc
1921 ggctgatttg ctcactttct gtctcctctg tcatactcta gttccttaca aactcttcac
1981 ggaccacggc ggcctcaacg agaagcgcaa gcagcggcgc atccgcacca ctttcaccag
2041 tgcccagctc aaagagctgg aaagggtctt cgcggagact cactaccccg acatctacac
2101 tcgggaggag ctggccctga agatcgacct cacagaggcg cgagtccagg tacgcgcgcc
2161 tggaaaccga ccccgctccg ccgcactggt ccggggaggt gtggggtgag gggcggctgg
2221 tgaaattcga agtcctggag cctcgagtga aaggaccta gggccccatg gccgatcaga
2281 aatactggat ttggtgtggc tgtgcgttcg agagaggctt agagcgcacg ctcttggcat
2341 tttatttaca gttgcgaagt gtttcccacc cgagcagaga catgggggc cttgggacgt
2401 ggatgagcga tgcaatttcg gggacaggaa gtgcctgtgg tggaaggtgt gcagactttg
2461 ctcccgtatt ataagttttt ccttctcccc tcccgccccc caaaaaaatg cctcctaact
2521 caagtgcttt taacctggcc ccatggcata taggttcatt ttcccggaaa ctgtgacttg
2581 cattagattt gcaaagggtc tgtgacttca tgaaggtcaa gaaccatgac ttactccaac
2641 ctgttaaaca caggtgcgct cacgagttgg ccacagcgcc ttttgggtg agccccgac
2701 cgagaagcgg tgcgcaccat tgcacgcttt tccaggctca aaggccgggg atgggcagcg
2761 gagcaaaccc agagaggatc ccttttcctt ttaccaatta gagtttaact ttagaactta
2821 ggcttagggg tgaatggcga gctcggggct tgctcaagaa gccgactgaa cagaggccca
2881 ccaaaataag gccttccctt ttcgggtctt tctgggacct gcggctttt aaactctgcc
2941 gcaagccttc atgtccctgg cgtgctcact cccctaaga aagtttctcc gaaatgcac
3001 agcaataaga agcggtagac ttggtggatg tgcgcgcggg ggtgatcaca gcgcatgggg
3061 aggagggtgt taaaacaagc cgaagtagaa cttgggccac cctaaccggt gcttttcttt
3121 cccattttct tctttctccc cctgcttcac cgtctctcct tccgtcttgg gccaggtgtg
3181 gttccagaac cgccgcgcca agtttcgcaa gcaggagcgc gcagcggcag ccgcagcggc
3241 cgcggccaag aacggctcct cgggcaaaaa gtctgactct tccagggacg acgagagcaa
3301 agaggccaag agcactgacc cggacagcac tgggggccca ggtcccaatc ccaaccccac
3361 ccccagctgc ggggcgaatg gaggcggcgg cggcgggccc agcccggctg gagctccggg
3421 ggcggcgggg cccggggggcc cggaggcga accggcaag ggcggcgcag cagcagcggc
3481 ggcggccgcg gcagcggcgg cggcggcCgc ggcagcggcg gcagctggag gcctggctgc
3541 ggctgggggc cctggacaag gctgggctcc cggccccggc cccatcacct ccatcccgga
3601 ttcgcttggg ggtcccttcg gcagcgtcct atcttcgctc caaagaccca acggtgccaa
3661 agccgcctta gtgaagagca gtatgttctg atctggaatc ctgcggcggc ggcggcggcg
3721 gcgacagcgg gcgagccagg gcccgggcgg gcgagtgggc gagcgggtag gcccaaggct
3781 attgtcgtcg ctgctgccat ggcttttca ttgagggcct aaagtaatcg cgctaagaat
3841 aaagggaaaa cggcgtcgcc ctcatttcaa ccccactcct accccttcc tcaaccccca
```

Figure 3 Cont'd

```
3901 aacaaaacaa acaaacttcc ctggcttcgc acctgcctgg ggcctcgcag cggggccagg
3961 gctccgcctg ctgatcgggg gttgtgagca gcgcggcctg gacgcggggc actctcaggg
4021 ggctgtgtct gcgtgtcagt ttgtgtctgt ctcggggaat gtgtgtctgt ggcccaagca
4081 ggtgacagga agagatgggg ggcctcaacc aacttagtga cttgtttaga aaaaaaagac
4141 aaaaagtaa aataaaaac aaaaagttg gaaggcagaa accattaaaa aacaaaaagc
4201 caacaaccca gaaaggttta aaaaacataa ggaaaaaaaa gacaaattaa aggaggggct
4261 aggggagaag ctgcagctgg agctgaaggc tcgatcttgt gaacccctaa atccgctccc
4321 tcctaacagc acggattctc ttggggctct tcttcaggga agagtaggga cgccgttcca
4381 gcccccttc ctatcgtgtc cttgggttcg ggtcactgcg gcgacgactt gctcagactg
4441 tcccggcggc cggagtgact ttctcgcacc cccttgcctg tcccacctcg ctgaacacca
4501 tcccgccatt agcgcatcgg aaccccacac agttgcaact cccaaccccg aatctttgca
4561 gccgttcggc cctgaaagat gccctatcca tgagatgcct tttcatctgc aaactctgca
4621 aaatgtgtct catgtttcgc aactcttttt ttccccctcg ctcccgccta ccccgtcggc
4681 attttcttct tccaccagct tttactgaac ttttttggcac tgctttggat tggggtcaat
4741 tgcagtccac gtaactggct gcagagaaat ctaccgagca aggaaaaggc acacacacac
4801 gtttgcaggg gtgtctcggt ttgcatttct gttggaatga tccgaactgg actcacatcc
4861 tgtatggtgg atggactgta tattgagggt tccattcttc gcgcagttta gacatctctg
4921 ttttgattct ttgttgttgt ttttatttta aaaggcacaa actctagata ttagttgaat
4981 gttgaggctt taacttttc ggtgtctttc tacaactgtg ttctgtgact caattgtatc
5041 gtgttaatat cagtgcagac tgtctcctct acgtgaccgt ataatgtttt tctcgtcttg
5101 tagtctctat ggcgtgtctt tatggtgtaa taaggttctc acggggtcaa tcttttgtgt
5161 ttagagaggc cacggttcag acaatggtat atattttgt tatcaggtgc atgtctgtct
5221 gatttctttt tttttcctgt tggactatgt ttgtgaacat aattgtcata agttatgttt
5281 cagattttg aatttattta tatgtgttat aatgaatgct tctatttaaa agggaaatat
5341 ttctacatgt gcttatagtt ttccaagagt gtaccattaa cttgattgtt gataataaaa
5401 accaaaagca agtctagcaa ttgaactctt cttttcttg attcttttt ttttttttt
5461 tttgggttgg tcattgtttt tttttttaa gttttttttt aaaggat
```

Figure 4A

```
   1 cctgagtctc ttgaaagcac atttagctgc aagaagaaat gcaatttata agatgctttc
  61 tctctgtctc tctttgtttt taaccccctc taaccaggtg tattttaaa gaaatccgct
 121 tatcgttcac ataaaccccc ttggcccact tactctatgt tacagggcgc ctgagtcttg
 181 ccaatgtccc agtcctttat aacatttcat gcacttcggg gggtaggctt gttgttaaat
 241 tgagcgtgta acactcttac aaaacaggtt ttctatgaca tcaaggtttc ttctccctaa
 301 ccgaggggga aaaaagaag aggacgaaga aggggaaaa cacacacact atctcaattt
 361 atgcctaagg tatatgatca gttaaaaagg cttaaaagct cggggaaatt ggatcaggga
 421 gaatcgtcac ccaactttca ttatttccaa gtagtgtgat tgaattaaag ggcagggagc
 481 tggttagaag ggaggatcag gggctcggtg cgtaatggtg tggtattaaa ttctaattag
 541 agatgcagga atcaatgata gggaggttgg acagctcagt tccccagtgc cagcccaata
 601 gacggatgag ttattgtcat gtaaaaagcg ccagcaataa gaccaaccgc tttgctattg
 661 tccaagtgga aagagccaag tttattatga ggactatatg ctctagagac ctcagacaag
 721 gcatctcata ggaggctttt tcataaaact aggctctgct ggtagtaagg aggccagttt
 781 ggaggcaggc gttgagctgt gcacatctcc ccactccagc caccttctcc atatccatct
 841 tttatttcat ttttccactt ggctgagcca tccagaacct tttcaatgta taaatggaa
 901 tattcttacc tcaattcctc tgcctacgag tcctgtatgg ctgggatgga cacctcgagc
 961 ctggcttcag cctatgctga cttcagttcc tgcagccagg ccagtggctt ccagtataac
1021 ccgataagga ccacttttgg ggccacgtcc ggctgccctt ccctcacgcc gggatcctgc
1081 agcctgggca ccctcaggga ccaccagagc agtccgtacg ccgcaggtta ggaccttcag
1141 ctttctcagc ggaggaagcc gcctttccgc ccgtatatag gaagccttga ttgcatttga
1201 aaatggaaat gtgtttagta tttaccaaac gaaatttgct tacacaaatg aaagaattta
1261 tcacgtttga agcgattgca gggaggggta attcacttac agggttacac tatcctagtc
1321 acacccgaac cgcccacaaa attatcttaa gctgccaaaa tgataggcat aatttattta
1381 ctttgcgatg agacgtatag cttagaaaat aattgaatta caaagagtaa agctcattac
1441 tggcagtgtc tcttttttta agaaccgaga gcggctcaca cttcttgggc tggtcatttt
1501 tatgattatt tctttaattt attattatt ttttgcagct ctttccccca acttttgagc
1561 cgggtcaact ttctgagaat tgaaaagttc ccaaagtggg actgtttggt aacttctttc
1621 cctggctccc ctgatattcc gactgatgtt ttgggatttt tttcctctct ggttttttcc
1681 tgctgaaagc actatctcaa gtccgtcaca tcgcgctgtt tcaatccacc caaaggcgct
1741 tgtgccagaa aggactccgc caagcccgaa gtttgagccc aggtttccgc agataacaaa
1801 tttcctcggt ttcttcccgc agcttctctc ggcaactctc tcgcgcgggt gtaggtagcg
1861 gctgccgtat gacctgacct tggagtcctc acattctagc tccacggccg gcgagctgcc
1921 ggctgatttg ctcactttct gtctcctctg tcatactcta gttccttaca aactcttcac
1981 ggaccacggc ggcctcaacg agaagcgcaa gcagcggcgc atccgcacca ctttcaccag
2041 tgcccagctc aaagagctgg aaagggtctt cgcggagact cactacccg acatctacac
2101 tcgggaggag ctggccctga agatcgacct cacagaggcg cgagtccagg tacgcgcgcc
2161 tggaaaccga ccccgctccg ccgcactggt ccggggaggt gtggggtgag gggcggctgg
```

Figure 4A Cont'd

```
2221 tgaaattcga agtcctggag cctcgagtga aaggaccta gggccccatg gccgatcaga
2281 aatactggat ttggtgtggc tgtgcgttcg agagaggctt agagcgcacg ctcttggcat
2341 tttatttaca gttgcgaagt gtttcccacc cgagcagaga catgggggggc cttgggacgt
2401 ggatgagcga tgcaatttcg gggacaggaa gtgcctgtgg tggaaggtgt gcagactttg
2461 ctcccgtatt ataagttttt ccttctcccc tcccgccccc caaaaaaatg cctcctaact
2521 caagtgcttt taacctggcc ccatggcata taggttcatt ttcccggaaa ctgtgacttg
2581 cattagattt gcaaagggtc tgtgacttca tgaaggtcaa gaaccatgac ttactccaac
2641 ctgttaaaca caggtgcgct cacgagttgg ccacagcgcc ttttttgggtg agcccccgac
2701 cgagaagcgg tgcgcaccat tgcacgcttt tccaggctca aaggccgggg atgggcagcg
2761 gagcaaaccc agagaggatc ccttttcctt ttaccaatta gagtttaact ttagaactta
2821 ggcttagggg tgaatggcga gctcggggct tgctcaagaa gccgactgaa cagaggccca
2881 ccaaaataag gccttccctt ttcgggtctt tctgggacct gcggcttttt aaactctgcc
2941 gcaagccttc atgtccctgg cgtgctcact cccctaaga aagtttctcc gaaaatgcac
3001 agcaataaga agcggtagac ttggtggatg tgcgcgcggg ggtgatcaca gcgcatgggg
3061 aggagggtgt taaaacaagc cgaagtagaa cttgggccac cctaaccggt gctttctttt
3121 cccattttct tctttctccc cctgcttcac cgtctctcct tccgtcttgg gccaggtgtg
3181 gttccagaac cgccgcgcca agtttcgcaa gcaggagcgc gcagcggcag ccgcagcggc
3241 cgcggccaag aacggctcct cgggcaaaaa gtctgactct tccagggacg acgagagcaa
3301 agaggccaag agcactgacc cggacagcac tgggggccca ggtcccaatc ccaaccccac
3361 ccccagctgc ggggcgaatg gaggcggcgg cggcgggccc agcccggctg gagctccggg
3421 ggcggcgggg cccgggggcc cgggaggcga acccggcaag ggcggcgcag cagcagcggc
3481 ggcggccgcg gcagcggcgg cggcggcagc xxxxxxxxxx xxxxxtggag gcctggctgc
3541 ggctggggc cctggacaag gctgggctcc cggccccggc ccatcacct catcccgga
3601 ttcgcttggg ggtcccttcg gcagcgtcct atcttcgctc caaagaccca acggtgccaa
3661 agccgcctta gtgaagagca gtatgttctg atctggaatc ctgcggcggc ggcggcggcg
3721 gcgacagcgg gcgagccagg gcccgggcgg gcgagtgggc gagcgggtag gcccaaggct
3781 attgtcgtcg ctgctgccat ggcttttca ttgagggcct aaagtaatcg cgctaagaat
3841 aaagggaaaa cggcgtcgcc ctcatttcaa ccccactcct accccttcc tcaacccca
3901 aacaaaacaa acaaacttcc ctggcttcgc acctgcctgg ggcctcgcag cggggccagg
3961 gctccgcctg ctgatcgggg gttgtgagca gcgcggcctg gacgcggggc actctcaggg
4021 ggctgtgtct gcgtgtcagt ttgtgtctgt ctcggggaat gtgtgtctgt ggcccaagca
4081 ggtgacagga agagatgggg ggcctcaacc aacttagtga cttgtttaga aaaaaagac
4141 aaaaagtaa aataaaaac aaaaagttg aaggcagaa accattaaaa aacaaaagc
4201 caacaaccca gaaaggttta aaaacataa ggaaaaaaaa gacaaattaa aggagggct
4261 aggggagaag ctgcagctgg agctgaaggc tcgatcttgt gaaccctaa atccgctccc
```

Figure 4A Cont'd

```
4321 tcctaacagc acggattctc ttggggctct tcttcaggga agagtaggga cgccgttcca
4381 gccccccttc ctatcgtgtc cttggttcg ggtcactgcg gcgacgactt gctcagactg
4441 tcccggcggc cggagtgact ttctcgcacc cccttgcctg tcccacctcg ctgaacacca
4501 tcccgccatt agcgcatcgg aaccccacac agttgcaact cccaaccccg aatctttgca
4561 gccgttcggc cctgaaagat gccctatcca tgagatgcct tttcatctgc aaactctgca
4621 aaatgtgtct catgtttcgc aactcttttt ttccccctcg ctcccgccta ccccgtcggc
4681 attttcttct tccaccagct tttactgaac tttttggcac tgctttggat tggggtcaat
4741 tgcagtccac gtaactggct gcagagaaat ctaccgagca aggaaaaggc acacacacac
4801 gtttgcaggg gtgtctcggt ttgcatttct gttggaatga tccgaactgg actcacatcc
4861 tgtatggtgg atggactgta tattgagggt tccattcttc gcgcagttta gacatctctg
4921 ttttgattct ttgttgttgt ttttatttta aaaggcacaa actctagata ttagttgaat
4981 gttgaggctt taacttttttc ggtgtctttc tacaactgtg ttctgtgact caattgtatc
5041 gtgttaatat cagtgcagac tgtctcctct acgtgaccgt ataatgtttt tctcgtcttg
5101 tagtctctat ggcgtgtctt tatggtgtaa taaggttctc acggggtcaa tcttttgtgt
5161 ttagagaggc cacggttcag acaatggtat atattttgt tatcaggtgc atgtctgtct
5221 gatttctttt ttttcctgt tggactatgt ttgtgaacat aattgtcata agttatgttt
5281 cagattttg aatttattta tatgtgttat aatgaatgct tctatttaaa agggaaatat
5341 ttctacatgt gcttatagtt ttccaagagt gtaccattaa cttgattgtt gataataaaa
5401 accaaaagca agtctagcaa ttgaactctt cttttttcttg attctttttt tttttttttt
5461 tttgggttgg tcattgtttt ttttttttaa gttttttttt aaaaggat
```

Figure 4B

```
  1  mykmeysyln ssayescmag mdtsslasay adfsscsqas gfgynpirtt fgatsgcpsl
 61  tpgscslgtl rdhqsspyaa vpyklftdhg glnekrkqrr irttftsaql kelervfaet
121  hypdiytree lalkidltea rvquwfqnrr akfrkgeraa aaaaaaakng ssgkksdssr
181  ddeskeakst dpdstggpgp npnptpscga nggggggpsp agapgaagpg gpggepgkgg
241  aaaaaaaaaa aaaaaxxxxx gglaaaggpg qgwapgpgpi tsipdslggp fgsvlsslqr
301  pngakaalvk ssmf
```

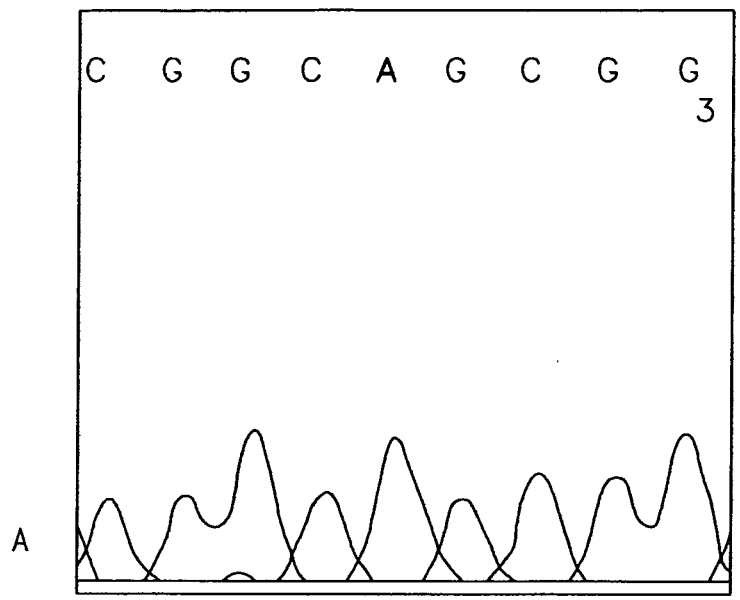
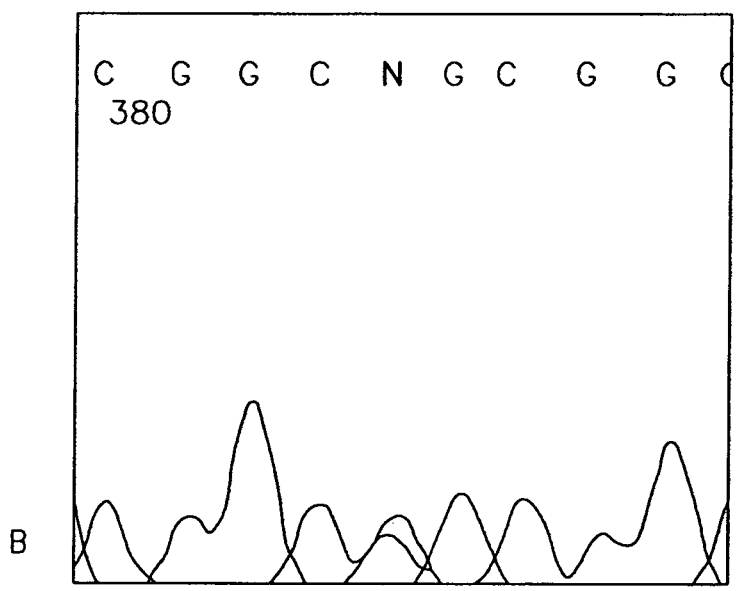
FIG. 6

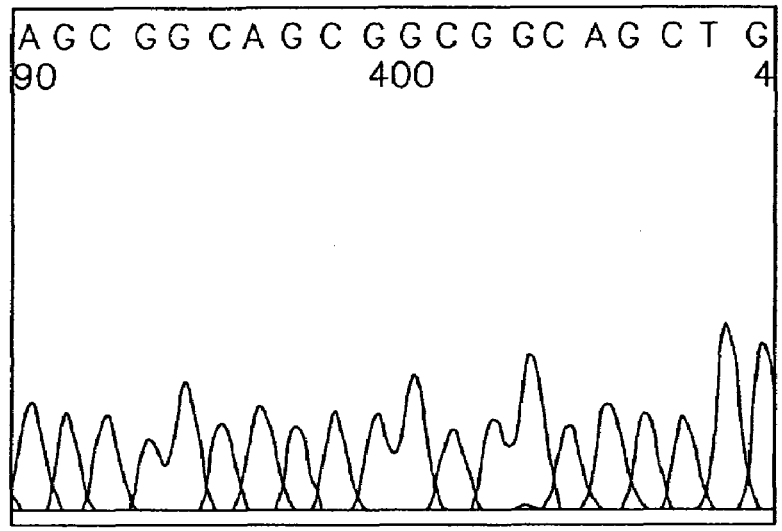
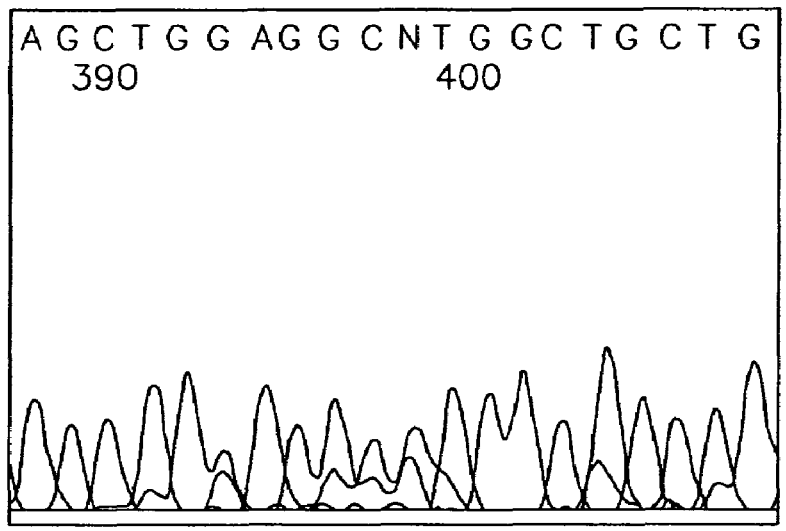
FIG. 7

PHOX2B POLYMORPHISMS AS HIRSCHSPRUNG'S DISEASE DIAGNOSTIC MARKERS AND METHODS BASED THEREON

This application claims the benefit of U.S. Provisional Application No. 60/370,968, filed Apr. 8, 2002, which is incorporated by reference herein in its entirety.

1. FIELD OF THE INVENTION

The invention relates generally to polymorphisms or mutations of the PHOX2B gene. More particularly, the invention relates to polymorphisms or mutations of the PHOX2B gene that are responsible for the disease Hirschsprung's disease (HSCR), which is a neural crest-associated developmental disorder. The invention is directed to the identification, isolation, and cloning of the DNA sequence of mutants of the PHOX2B gene, as well as the characterization of their transcripts and gene products. The invention further identifies deletions, insertions, substitutions of nucleotides in the PHOX2B gene. Specifically, the invention is directed to the detection of a single base-pair polymorphism in the PHOX2B gene that is associated with HSCR. The invention also relates to methods and kits for screening for carriers of mutations of the PHOX2B gene and the diagnosis of HSCR. The invention further relates to diagnosing predisposition or susceptibility to increased risk of developing HSCR by screening for the presence of a polymorphism associated with HSCR. The invention also relates to compositions for screening for the polymorphism and treatment choices for patients having the polymorphism of the present invention. The invention further relates to providing polymorphisms in the PHOX2B gene as genetic markers and for forensic use, paternity test and genetic mapping. The invention is also directed to screening assays and therapeutic and prophylactic methods.

2. BACKGROUND OF THE INVENTION

2.1. Hirschsprung'Disease

Hirschsprung's disease (HSCR), regarded as a multigenic neurocristopathy, is a congenital disorder that involves aganglionosis, in which there is an absence of ganglion cells in the nerve plexuses of the lower digestive tract. The condition presents in the neonatal period as failure to pass meconium, chronic severe constipation, colonic distention, secondary electrolyte disturbances and, sometimes, enterocolitis and bowel perforation. The estimated population incidence is 1/5000 live birth (Holschneider 1982). Males are 3.5–4.0 times more likely to be affected than females (Bodian and Carter 1963; Badner et al. 1990). HSCR may occur with other neurodevelopmental disorders such as Waardenburg syndrome type 4 (Pingault et al. 1998; WS4), and it may also be associated with a variety of other anomalies including chromosomal abnormalities and syndromes with Mendelian pattern of inheritance. Approximately, 20% of the HSCR cases are familial, with a sibling recurrence risk of 4%.

Aganglionosis is due to a disorder of the enteric nervous system (ENS) in which ganglion cells fail to innervate the lower gastrointestinal tract during embryonic development. The extent of the aganglionic segment is variable, and is reflected in the severity of the disease. The genetic signals critical for neural crest migration and differentiation into enteric ganglia include genes encoding neurotrophic factors and their receptors. Substantial evidence has been presented to show that HSCR has a complex genetic etiology requiring the interaction of several unlinked genes, and possibly environmental factors, to produce the phenotype (Angrist et al. 1993; Angrist et al. 1996; Bolk et al. 2000; Doray et al. 1998; Hofstra et al. 1999; Puffenberger et al 1994; Svensson et al. 1999). It has been postulated that the degree of expression of the receptor tyrosine kinase gene (RET) is critical for the HSCR phenotype (Bolk et al. 2000). However, only around 30% of HSCR cases are heterozygous for mutations in this gene. RET mutations do not account for all HSCR cases and lack genotype-phenotype correlation due to low penetrance, indicating that genes other than RET are implicated in the disease. This has led to the search for other susceptibility and modifying genes that could lead to clinical expression in HSCR patients. Interestingly, HSCR genes identified so far code for protein members of two important signaling pathways involved in the development of enteric ganglia: RET and endothelin receptor B (EDNBR) signaling pathways. Interaction between these two signalling pathways could modify RET expression (Chakravarti 1996), and therefore HSCR phenotype (Bolk et al. 2000; Sakai et al. 2001). Nevertheless, for almost every HSCR gene described, incomplete penetrance and variable expression of the HSCR phenotype has also been observed implying that modifying locus are needed for the expression of the HSCR phenotype (Salomon et al. 1996; Hofstra et al. 1997). Therefore, other genes implicated in RET expression and/or intestinal neurodevelopment are to be considered as candidate genes for HSCR. A number of transgenic mouse models have been established which demonstrated the involvement of these genes in enteric neuron system development. Mice that lack the function of Ret are devoid of enteric neurons and similar phenotypes are seen in mice with mutations in other components of the RET (Schuchardt et al. 1994; Shen et al. 2002) as well as EDNRB pathways (Baynash et al. 1994). In addition, mutations in the gene encoding the transcription factor SOX10 account for the Dom phenotype which is regarded as a model for HSCR (Herbarth et al. 1998). Interestingly, Sox10 is needed to modulate Ret and Ednrb expression (Lang et al. 2000; Southard-Smith et al. 1999). In humans, SOX10 mutations have been identified in patients with HSCR and pigmentary anomalies consistent with WS4 (Pingault et al. 1998).

HSCR non-Mendelian pattern suggests a complex disorder with major contributions from predisposing genetic factors, which interact with the overall genetic background and/or environmental insults to determine the phenotype. The ability to identify the genetic factors that increase the risk for HSCR would be a breakthrough for the understanding of HSCR, and other polygenic complex disorders and congenital malformations considered multifactorial in origin.

2.2. The PHOX2B Gene

The paired mesoderm homeobox 2b gene (PHOX2B) encodes a transcription factor (homeodomain protein), which is involved in the development of several noradrenergic neuron populations. In mice, PHOX2B expression starts as soon as the enteroblasts invade the foregut mesenchyme and it is maintained throughout the development into enteric neurons. In PHOX2B homozygous mutants, enteric-neuron precursors arrive at the foregut but migration towards the mid- and hindgut is arrested (Dubreuil et al., 2000, Development 127:5191–5201). Consequently, the homozygous disruption of the PHOX2B gene results in the absence of enteric ganglia, feature which is reminiscent of HSCR. Furthermore, there is no Ret expression in PHOX2B mutant embryos. This indicates that regulation of Ret by PHOX2B could account for the failure of the ENS to develop (Pattyn et al., 1999, Nature 399:366–370).

PHOX2B transcription factor (Goridis, C., and Brunet, J. -F., Curr. Opin. Neurobiol. 9:47–53, 1999) is expressed in all central and peripheral noradrenergic neurons just as these neurons are acquiring their differentiated phenotype (Tiveron, M. -C., et al., J. Neurosci. 16:7649–7660, 1996; Pattyn, A., et al., Development 124:4065–4075, 1997). PHOX2B binding site contribute to dopamine-b-hydroxylase (DBH) promoter activity and forced expression of the factor can activate the promoter in DBH-negative cell lines (Swanson, D. J., et al., J. Biol. Chem. 272:27382–27392, 1997; Yang, C., et al., J. Neurochem. 71:1813–1826, 1998; Kim, H. -S., et al., J. Neurosci. 18:8247–8260, 1998). Moreover, loss of function experiments demonstrate that PHOX2B is an essential determinant of noradrenergic phenotype (Morin, X., et al., Neuron 18:411–423, 1997;).

The DNA and amino acid sequences for PHOX2B have previously been reported (Yokoyama et al. 1996). Its coding region consists of 945 base pairs (bp) allocated in three exons yielding a homeodomain protein of 314 amino acid residues (Yokoyama et al. 1999)(see FIG. 2). PHOX2B DNA and amino acid sequences are hereby incorporated by reference SEQ ID No. 1 and SEQ ID No. 2 respectively). Exon 1 stretches from base 885 to base 1126. Exon 2 stretches from base 1962 to 2149. Exon 3 strectches from 3176 to 3691. (See FIG. 8). The wildtype gene sequence for PHOX2B is provided in SEQ ID No. 1 in FIG. 1.

2.3. Polymorphisms

The genomes of all organisms undergo spontaneous mutation in the course of their continuing evolution generating variant forms of progenitor sequences (Gusella, Ann. Rev. Biochem. 55, 831–854 (1986)). The variant form may confer an evolutionary advantage or disadvantage relative to a progenitor form or may be neutral. In some instances, a variant form confers a lethal disadvantage and is not transmitted to subsequent generations of the organism. In other instances, a variant form confers an evolutionary advantage to the species and is eventually incorporated into the DNA of many or most members of the species and effectively becomes the progenitor form. In many instances, both progenitor and variant form(s) survive and co-exist in a species population. The coexistence of multiple forms of a sequence gives rise to polymorphisms.

Several different types of polymorphism have been reported. A restriction fragment length polymorphism (RFLP) means a variation in DNA sequence that alters the length of a restriction fragment as described in Botstein et al., Am. J. Hum. Genet. 32, 314–331 (1980). The restriction fragment length polymorphism may create or delete a restriction site, thus changing the length of the restriction fragment. RFLPs have been widely used in human and animal genetic analyses (see WO 90/13668; WO90/11369; Donis-Keller, Cell 51, 319–337 (1987); Lander et al., Genetics 121, 85–99 (1989)). When a heritable trait can be linked to a particular RFLP, the presence of the RFLP in an individual can be used to predict the likelihood that the animal will also exhibit the trait.

Other polymorphisms take the form of short tandem repeats (STRs) that include tandem di-, tri- and tetranucleotide repeated motifs. These tandem repeats are also referred to as variable number tandem repeat (VNTR) polymorphisms. VNTRs have been used in identity and paternity analysis (U.S. Pat. No. 5,075,217; Armour et al., 1992, FEBS Lett. 307, 113–115; Horn et al., WO 91/14003; Jeffreys, EP 370,719), and in a large number of genetic mapping studies.

Other polymorphisms take the form of single nucleotide variations between individuals of the same species. Approximately 1 in every 1000 nucleotides differs between any two copies of the human genome (Cooper, 1996, Hum. Genet. 69:201–205). Some of these genetic variations, or SNPs, lead to differences in the proteins encoded by such genes. Others are "silent", residing in non-protein coding regions of the genome. Some of these polymorphisms may also result in defective protein expression (e.g., as a result of defective splicing). Other single nucleotide polymorphisms have no phenotypic effects. Such SNPs are now being used, for example, to diagnose genetic disorders, determine a predisposition to genetic disease, identify or determine the ancestry of a genetic sample, or correlate genetic sequences with phenotypic conditions, such as complex disorders or drug response and toxicity (Risch and Merikangas, 1996, Science 273:1516–1517). This powerful combination of genetic and molecular biological approaches is changing the face of drug development. SNPs have been correlated with Huntington's disease, Alzheimer's disease, and various forms of breast cancer. In the emerging field of pharmacogenomics, specific SNPs are being used to determine and predict a patient's susceptibility to diseases as well as drug toxicity and reponse. Pharmacogenomics can also provide tools to identify new targets for designing drugs and to optimize the use of existing drugs. The hope is that this understanding will ultimately lead to the early diagnosis, prevention, and treatment of genetic diseases. Single nucleotide polymorphisms are far more frequent than RFLPS, STRs and VNTRs. Some single nucleotide polymorphisms occur in protein-coding sequences, in which case, one of the polymorphic forms may give rise to the expression of a defective or other variant protein and, potentially, a genetic disease. Examples of genes, in which polymorphisms within coding sequences give rise to genetic disease include β-globin (sickle cell anemia) and CFTR (cystic fibrosis).

Single nucleotide polymorphisms can be used in the same manner as RFLPs, and VNTRs but offer several advantages. Single nucleotide polymorphisms occur with greater frequency and are spaced more uniformly throughout the genome than other forms of polymorphism. The greater frequency and uniformity of single nucleotide polymorphisms means that there is a greater probability that such a polymorphism will be found in close proximity to a genetic locus of interest than would be the case for other polymorphisms. Also, the different forms of characterized single nucleotide polymorphisms are often easier to distinguish that other types of polymorphism (e.g., by use of assays employing allele-specific hybridization probes or primers).

Despite the increased amount of nucleotide sequence data being generated in recent years, only a minute proportion of the total repository of polymorphisms in humans and other organisms has so far been identified. The paucity of polymorphisms hitherto identified is due to the large amount of work required for their detection by conventional methods. For example, a conventional approach to identifying polymorphisms might be to sequence the same stretch of oligonucleotides in a population of individuals by didoxy sequencing.

3. SUMMARY OF THE INVENTION

The present invention is based upon the observation of the present inventors that a distinct polymorphism in the PHOX2B gene is associated with HSCR. The present invention provides diagnostic screening of a population for predisposition or susceptibility to increased risk for HSCR by detecting a polymorphism in the PHOX2B gene. In accordance with the present invention, mutated form of the PHOX2B gene, which is associated with HSCR, have been identified, isolated, cloned and sequenced. Other mutations identified in the present invention in the PHOX2B gene comprise polymorphisms which include addition, deletion, rearrangement, or replacement of one or more nucleotides. The present invention, therefore, represents the first opportunity to accurately and non-invasively screen and diagnose HSCR in a substantial portion of the population. The present also provides compositions for screening for the polymorphism and improved treatment choices for patients having the polymorphism of the present invention. In addition, the present invention provides method of treatment, prophylaxis, management or amelioration of one or more symptoms associated with HSCR. Still further the PHOX2B gene may be used as genetic markers, including but not limited to, for identifying or determining the source of a genetic sample, or correlate a test sample with other genetic sample, such as for example, in forensic testing and paternity testing.

In a preferred embodiment, the mutation of the PHOX2B gene which is associated with HSCR comprises a single nucleotide polymorphism. In another preferred embodiment, the mutation of the PHOX2B gene comprises deletion of one or more nucleotides.

In specific embodiments, the present invention relates to an isolated nucleic acid molecule comprising a nucleic acid sequence selected from the group consisting of SEQ ID NOS:3, 4, and 6.

In a specific embodiment, the present invention relates to an isolated nucleic acid molecule comprising nucleic acid sequence of SEQ ID NO:3 (which corresponds to the genomic sequence of the PHOX2B gene containing a mutation in which a single base A is substituted by a G at position 2250, as shown in FIG. 2 ("A→G (2250)")). In an embodiment, the mutation is a heterozygous change, in which only one allele of the PHOX2B gene harbors the A to G change, as shown in FIG. 5B. In another embodiment, the mutation is a homozygous change, in which both alleles of the PHOX2B gene harbor the A to G change, as shown in FIG. 5C.

In a specific embodiment, the present invention relates to an isolated nucleic acid molecule comprising nucleic acid sequence of SEQ ID NO:4 (which corresponds to the genomic sequence of the PHOX2B gene containing a mutation in which a single base A is substituted by a C at position 3508, as shown in FIG. 3 ("A→C (3508)")). In an embodiment, the mutation is a heterozygous change, in which only one allele of the PHOX2B gene harbors the A to C change, as shown in FIG. 6B. In another embodiment, the mutation is a homozygous change, in which both alleles of the PHOX2B gene harbor the A to C change.

In a specific embodiment, the present invention relates to an isolated nucleic acid molecule comprising nucleic acid sequence of SEQ ID NO:5 (which corresponds to the genomic sequence of the PHOX2B gene comprising a fifteen bases deletion from position 3511–3525, as shown in FIG. 4A ("DEL (3511)")). In an embodiment, the mutation is a heterozygous change, in which only one allele of the PHOX2B gene harbors the deletion, as shown in FIG. 7B. In another embodiment, the mutation is a homozygous change, in which both alleles of the PHOX2B gene harbor the deletion.

In one embodiment, the nucleic acid is DNA. In another embodiment, the DNA is cDNA. In another embodiment, the nucleic acid is RNA.

The present invention provides nucleic acid molecules comprising fragments having a portion of the PHOX2B gene of the invention. The nucleic acid fragments comprise nucleotide sequences corresponding to a portion of a nucleic acid molecule of the invention.

The present invention provides a cloning vector comprising a nucleic acid molecule of the invention in a host cell for the vector. The invention further provides an expression vector comprising the nucleic acid molecule of the invention operably linked to a promoter sequence capable of directing expression of the nucleic acid molecule in host cells for the vector.

The present invention provides a method of producing a mutant PHOX2B polypeptide comprising the steps of transforming host cells with a vector of the invention; culturing the cells; and isolating the mutant PHOX2B polypeptide.

The present invention provides a mutant PHOX2B polypeptide which comprises the amino acid sequence of SEQ ID NO:6 (which corresponds to the wild-type amino acid sequence of the PHOX2B gene containing a mutation in which 5 alanine residues at positions 256–260, as shown in FIG. 4B). In one embodiment, the peptide is labeled. In another embodiment, the peptide is a fusion protein. In a specific embodiment, the fusion protein is a fusion protein comprising PHOX2B polypeptide and a heterologous polypeptide. As used herein, the term "fusion protein" refers to a polypeptide that comprises an amino acid sequence of a first protein or functional fragment, analog or derivative thereof, and an amino acid sequence of a heterologous protein (i.e., a second protein or functional fragment, analog or derivative thereof different than the first protein or functional fragment, analog or derivative thereof).

The present invention provides a use of a peptide of the invention as an immunogen for the production of antibodies.

The present invention provides a method to detect the presence of a PHOX2B gene mutation that is associated with HSCR in an individual. The method comprises the steps of: providing a biological sample comprising DNA or RNA from the individual; and assessing the DNA or RNA for the presence of the mutant PHOX2B allele of a nucleotide mutation A→G(2250), wherein the presence of the PHOX2B mutation in the genome of the individual indicates that the individual have an increased risk of predisposition or susceptibility to HSCR.

In an embodiment, the invention is directed to a method of determining the source of a first biological sample from a subject compared to a second biological sample. The method comprises: (a) providing a first biological sample from the subject; (b) testing the first biological sample for the presence of a mutation of the PHOX2B gene at nucleotide positions 2250, 3508, and/or 3511–3525 of SEQ ID NO:1; (c) testing the second biological sample for the presence of a mutation of the PHOX2B gene at nucleotide positions 2250, 3508, and/or 3511–3525 of SEQ ID NO:1; and (d) comparing the mutations present in step (b) and (c); wherein the presence of identical mutation in the first biological sample compared to the second biological sample indicates that the first and second biological samples are obtained from an identical source.

The present invention provides a method to detect the presence of a PHOX2B gene mutation in an individual. The method comprises the steps of: providing a biological sample comprising DNA or RNA from the individual; and assessing the DNA or RNA for the presence of the mutant PHOX2B allele of a nucleotide mutation A→C (3508).

The present invention provides a method to detect the presence of a PHOX2B gene mutation in an individual. The method comprises the steps of: providing DNA or RNA from the individual; and assessing the DNA or RNA for the presence of the mutant PHOX2B allele of a deletion, DEL (3511).

The present invention provides a method to diagnose or detect a predisposition, or increased risk to HSCR by detecting the presence of a PHOX2B gene mutation, wherein the detection can be made in combination with one or more polymorphisms in the PHOX2B gene or other genes including but not limited to, RET, EDNBR, SOX10, EDN3, and GDNF. Thus, in an embodiment of the invention, the method further comprises assessing the DNA or RNA for the presence of any HSCR-associated polymorphisms, wherein the presence of the any HSCR-associated polymorphisms in combination with the presence of at least one other polymorphism indicates that the individual has an increased risk of predisposition or susceptibility to HSCR.

The present invention provides a method to detect the presence or absence of a PHOX2B gene mutation that is associated with HSCR in an individual. The method comprises the steps of subjecting the DNA or RNA of an individual to amplification using oligonucleotide primers flanking the nucleotide polymorphism A→G(2250).

The present invention provides a method to detect the presence of a PHOX2B gene mutation in an individual. The method comprises the steps of subjecting the DNA or RNA of an individual to amplification using oligonucleotide primers flanking the nucleotide polymorphism A→C (3508), or flanking a portion or the entire deletion, DEL (3511).

The present invention provides oligonucleotides for use in an assay to detect the presence of PHOX2B gene mutation in an individual. In specific embodiments, the oligonucleotides of the invention comprise the sequences of SEQ ID NOS:7, 8, 9, 10, 11, and 12. The present invention provides a kit for the detection of the presence of a PHOX2B gene mutation. The kit of the invention comprises the oligonucleotides of the invention.

Another aspect of the invention is a kit for the detection of a polymorphism in the PHOX2B gene which is associated with HSCR in a subject. The sample kit comprises a first oligonucleotide of at least 8 nucleotides in length of a portion of a nucleic acid sequence of SEQ ID NO:3, wherein the oligonucleotide is used to amplify a region comprising two or more nucleotides at position 2250 of the PHOX2B gene in the DNA or RNA from a biological sample of the subject. In another aspect of the invention the kit further comprises at least a second oligonucleotide of 8 nucleotides in length which is a reverse complement of a portion of a nucleic acid sequence of SEQ ID NO:3, wherein the first and second oligonucleotides comprise a primer pair.

A further aspect of the invention is a method for treating a subject diagnosed as having HSCR, comprising modulating the PHOX2B level or activity. The subject can be homozygous for A→G (2250) or heterozygous for A→G (2250).

A further aspect of the invention is a method for forensic testing or paternity testing, comprising determining the genotype of a test individual. The test individual can be homozygous for A→G (2250), A→C (3508) or DEL (3511); or heterozygous for A→G (2250), A→C (3508) or DEL (3511); or compound heterozygous or compound homozygous for A→G (2250) and A→C (3508); A→G (2250) and DEL (3511); or A→C (3508) and DEL (3511).

The present invention provides an animal model for HSCR which comprises a mammal comprises a mutant nucleic acid molecule of the invention.

A further aspect of the invention is a method to screen mammals for susceptibility to HSCR, comprising, screening such mammals for a mutation in the PHOX2B gene and wherein those mammals identified as having a mutation are more susceptible to HSCR than mammals not identified as having a mutation. In a preferred embodiment, the mammal is human.

The present invention provides therapeutics for treatment, mitigation of symptoms associated with HSCR. The therapeutics modulates the level or activity of the PHOX2B gene.

4. BRIEF DESCRIPTION OF THE FIGURES

FIGS. 1A & B. (A) A portion of the sequence of wild-type PHOX2B (Genbank accession number AB015671)(SEQ ID NO:1) which encode a wild-type PHOX2B protein (SEQ ID NO:2). (B) The amino acid sequence of SEQ ID NO:2 is encoded by the nucleic acid molecule of SEQ ID NO:1.

FIG. 2. A novel polymorphism from patients with HSCR having a single base substitution at position 2250 of the wild-type sequence of the PHOX2B gene, where an A is changed to a G (SEQ ID NO:3).

FIG. 3. The sequence of a novel polymorphism identified in the third exon of PHOX2B having a single base substitution at position 3508 of the PHOX2B gene sequence, where an A is changed to a C (A/C) (SEQ ID NO:4).

FIGS. 4A & B. (A) The sequence of a novel polymorphism identified in the third exon of PHOX2B (SEQ ID NO:5). (B) In this case the mutation is a fifteen-base deletion resulting in the loss of 5 amino-acid (alanine-alanine-alanine-alanine-alanine) starting at position 256 of the PHOX2B gene sequence (SEQ ID NO:6).

FIGS. 5A, B, & C. (A) A portion of the sequence of wild-type PHOX2B (Genbank accession number AB015671)(SEQ ID NO:1) which encode a wildtype PHOX2B protein (SEQ ID NO:2). (B) A novel polymorphism from patients with HSCR having a single base substitution at position 2250 of the wild-type sequence of the PHOX2B gene, where an A is changed to a G (SEQ ID NO:3). The figure shows a heterozygous change, in which only one allele of the PHOX2B gene harbors the A to G change. (C) The change A to G (A/G) are shown in both alleles of the gene.

FIGS. 6A & B. (A) A portion of the sequence of wild-type PHOX2B. (B) a novel polymorphism identified in the third exon of PHOX2B having a single base substitution at position 3508 of the PHOX2B gene sequence, where an A is changed to a C (A/C) (SEQ ID NO:4). It shows a heterozygous change, in which only one allele of the PHOX2B gene harbors the A to C change.

FIGS. 7A & B. (A) A portion of the wild-type sequence of this part of the PHOX2B gene (SEQ ID NO:13) (B) A novel polymorphism identified in the third exon of PHOX2B (SEQ ID NO:5). In this case the mutation is a fifteen-base deletion resulting in the sequence of that portion shown in FIG. 7B (SEQ ID NO:14) and loss of 5 amino-acid (alanine-alanine-alanine-alanine-alanine) starting at position 256 of the PHOX2B amino acid sequence (SEQ ID NO:6).

Figure 8:
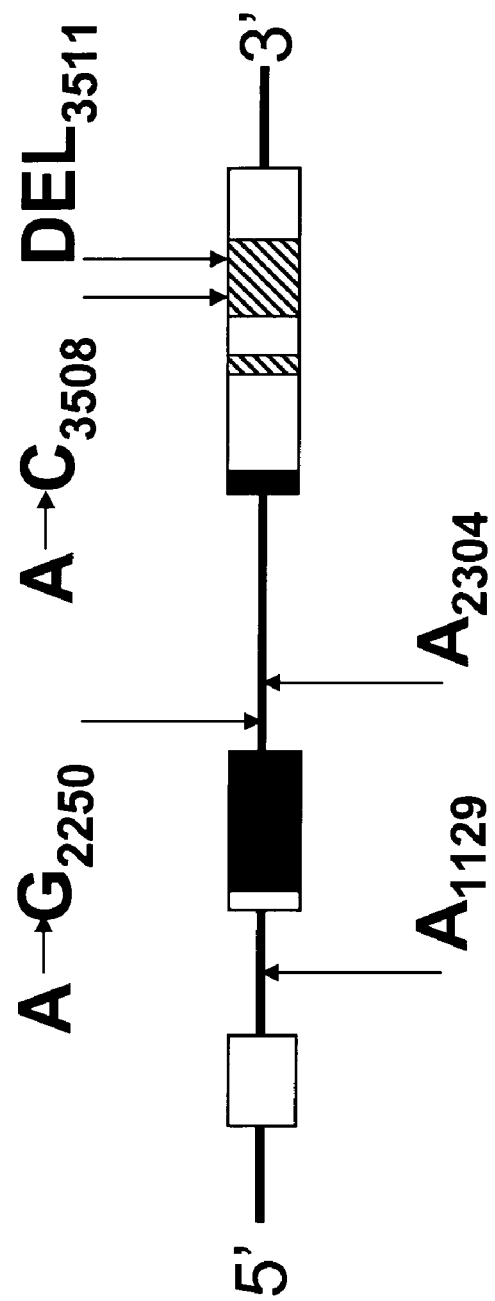

FIG. 8. A schematic diagram of Polymorphisms identified in the PHOX2B gene. The three PHOX2B exons are represented by rectangles. Black boxes indicate the homeodomain. Striped boxes indicate poly-alanine stretches (from codon 159 to 167 and from codon 241 to 260). Downward arrows show polymorphisms with frequencies that differ between patients with HSCR and controls. Upward arrows show polymorphisms found in every sample analyzed.

5. DETAILED DESCRIPTION OF THE INVENTION

The present inventors discovered that a polymorphism at the PHOX2B gene is associated with HSCR. Accordingly, the present invention provides a method for screening subjects for HSCR using the mutation as a genetic marker in the PHOX2B gene. The present invention further provides other genetic markers comprising mutations of the PHOX2B gene including various sequence polymorphisms, and/or sequence variants wherein nucleotide substitutions in the gene sequence that may or may not affect the function of the gene product. The PHOX2B gene as described herein refers to wild-type, variants, analogs, mutants, and polymorphic forms of the PHOX2B gene. The PHOX2B gene comprises not only coding sequences but also regulatory regions such as promoter, enhancer, and terminator regions. The PHOX2B gene further includes all introns and other DNA sequences spliced from the final PHOX2B gene RNA transcript. More specifically, the invention relates to diagnostic methods of HSCR based upon a particular polymorphism in the PHOX2B gene. In certain embodiments, the present invention is directed to an isolated nucleic acid molecule comprising the nucleic acid sequence of SEQ ID NO:1, wherein the nucleic acid molecule comprises mutations from nucleotide positions 1–2250. In specific embodiments, the mutation is selected from the group consisting of substitution, deletion, inversion, insertion, of one or more nucleotides selected from the nucleotide positions 1–2250 of SEQ ID NO:1. In least preferred embodiments, the mutation is a substitution at nucleotide positions 3004, 5343, or 5403 of SEQ ID NO:1.

In a specific embodiment, the polymorphism involves an adenine (A) to a guanine (G) transition at the nucleic acid position 2250 of SEQ ID NO:1. The nucleotide sequence of this polymorphism is shown in SEQ ID NO:3 and is known as A→G (2250).

The present invention also provides a method for diagnosing a subject for HSCR or screening a subject predisposed or susceptible to HSCR associated with a genetic polymorphism in the PHOX2B gene, said method comprising: (a) providing a biological sample from the subject; and (b) testing the sample for the presence mutations from nucleotide positions 1–2250 of SEQ ID NO:1, wherein, the presence of the mutation indicates that the subject is genetically predisposed to HSCR.

The present invention further provides other polymorphisms, which involves an adenine (A) to cytosine (C) transition at the nucleic acid position 3508 of SEQ ID NO:1. The nucleotide sequence of this polymorphism is shown in SEQ ID NO:4 and is known as A→C (3508). In another embodiment, the polymorphism involves a deletion of fifteen nucleotides at nucleic acid position 3511–3525 of SEQ ID NO:1. The nucleotide sequence of this polymorphism is shown in SEQ ID NO:5 and is known as DEL (3511). In other embodiments, the polymorphism involves a substitution of a nucleotide at nucleotide position at 1129 or 2304. These polymorphisms may be used as genetic markers for genomic mapping or in identifying or determining the source of a genetic sample, or correlate a test sample with other biological samples, such as in forensic testing or paternity testing.

The invention provides a method of diagnosing a disease condition associated with the mutation of the PHOX2B gene of the invention. The invention provides a method of identifying a mammal, including a human, predisposed or susceptible to a risk associated with a particular genotype in the PHOX2B gene. The method comprises determining the genotype of the PHOX2B gene in the mammal. In an embodiment, the method is to screen for an individual at risk of a condition or disease such as increased risk of HSCR by identifying the polymorphisms of the invention in the PHOX2B gene. Further, the present invention provides mutant PHOX2B gene which include the coding sequences as well as the non-coding sequences found in non-human species. All DNA sequences provided herein are understood to include complementary strands unless otherwise noted. It is understood that an oligonucleotide may be selected from either strand of the PHOX2B genomic or cDNA sequences. Furthermore, RNA equivalents can be prepared by substituting uracil for thymine, and are included in the scope of this invention, along with RNA copies of the DNA sequences of the invention isolated from cells. The oligonucleotide of the invention can be modified by the addition of peptides, labels, and other chemical moieties and are within the scope of the invention.

The present invention also provides PHOX2B proteins which includes wild-type and mutant forms of the protein, functionally active fragments, derivatives and analogs thereof. The present invention includes protein as isolated from human and animal sources, produced by enzymatic or chemical means, or through recombinant expression in an organism.

In addition, the present invention relates to the creation of appropriate animal models for the common, nonsyndromic HSCR since they do not yet exist. The present invention also provides tests for genetic factors would also serve as biomarkers, valuable for diagnosis, and useful in research on all aspects of the neural crest derived congenital malformations. A biomarker could be used prognostically for predicting whether a non-symptomatic subject is likely to transmit to his/her offsprings a predilection to develop Hirschsprung's disease. In particular there is need for a blood test for polymorphisms causing neural crest derived spectrum disorders. Families with affected members need to know whether they carry a mutation which could affect future pregnancies. The present invention further provides clinicians a test as an aid in diagnosis, and to classify subjects according to the etiology of their disease.

5.1. Mutations in the PHOX2B Gene

Specific diseases or disorders, e.g., genetic diseases or disorders, are associated with an aberrant expression of PHOX2B gene. Specifically, they may be associated with specific allelic variants of polymorphic regions of certain genes, which do not necessarily encode a mutated protein. Thus, the presence of a specific allelic variant of a polymorphic region of a gene, such as a single nucleotide polymorphism ("SNP"), in a subject can render the subject susceptible to developing a specific disease or disorder. Polymorphic regions in genes, e.g., PHOX2B gene, can be identified, by determining the nucleotide sequence of genes in populations of individuals. If a polymorphic region, e.g., SNP is identified, then the link with a specific disease can be determined by studying specific populations of individuals, e.g., individuals which developed a specific disease, such as HSCR. A polymorphic region can be located in any region of a gene, e.g., exons, in coding or non coding regions of exons, introns, and promoter region.

Gene mutations may be a single base substitution mutation resulting in an amino acid substitution, a single base substitution mutation resulting in a translational stop, an insertion mutation, a deletion mutation, or a gene rearrangement. The mutation may be located in an intron, an exon of the gene, or a promotor or other regulatory region which affects the expression of the gene or can serve as a markers in linkage disequilibrium analysis. DNA markers are used to track the inheritance of the genes through families. DNA markers are fragments of DNA with a defined physical location on a chromosome, whose inheritance can be monitored. The closer a DNA marker is to a susceptibility gene, the greater the probability that the marker and the susceptibility gene will be passed together from parent to child. This phenomenon is called genetic linkage. Once linkage to a specific chromosomal region has been obtained, the size of the region is narrowed down using a combination of physical and genetic mapping until the region is small enough to be sequenced and the susceptibility gene can be identified. After identification of the susceptibility gene, any polymorphisms in this gene can be determined and an analysis performed to see whether these mutations occur with greater prevalence in HSCR patients compared to non-HSCR individuals. A single nucleotide polymorphism (SNP) is shown in SEQ ID No:3, which have been identified in HSCR patient's samples. This polymorphism and other mutations are shown herinafter in the examples in Section 6.

PHOX2B comprises polymorphic regions, we have identified a specific allele which is associated with HSCR or with an increased likelihood of developing HSCR. Thus, the invention provides methods for determining the identity of the allele or allelic variant of a polymorphic region of the PHOX2B gene in a subject, to thereby determine whether the subject is at risk of transmitting and/or developing a disease or disorder that is associated with HSCR. Knowledge of the particular alteration or alterations, resulting in defective or deficient PHOX2B gene or protein in an individual (the PHOX2B genetic profile), alone or in conjunction with information on other genetic defects contributing to the same disease (the genetic profile of the particular disease) allows, understanding of disease pathogenesis for the dominant HSCR. Tests for genetic factors would also serve as biomarkers, valuable for diagnosis, and useful in research on all aspects of the neural crest derived congenital malformations. A biomarker could be used prognostically for predicting whether a non-symptomatic subject is likely to transmit to his/her offsprings a predilection to develop HSCR. For example, a PHOX2B population profile can be performed, by determining the PHOX2B gene profile, e.g., the identity of PHOX2B genes, in a patient population having a disease, which is caused by or contributed to by a defective or deficient PHOX2B gene.

The present methods of the invention provide means for determining if a subject is likely to transmit a disease, condition or disorder that is associated with the PHOX2B gene activity. The methods for determining whether a subject is likely to transmit a disease, which might be caused by or contributed to by an aberrant PHOX2B activity is characterized as comprising detecting, in a sample of cells from the subject, the presence or absence of a genetic alteration characterized by at least one of: (i) an alteration affecting the integrity of a gene encoding an PHOX2B polypeptide, or (ii) the mis-expression of the PHOX2B gene. For example, such genetic alterations can be detected by ascertaining the existence of at least one of: (i) a deletion of one or more nucleotides from a PHOX2B gene, (ii) an addition of one or more nucleotides to an PHOX2B gene, (iii) a substitution of one or more nucleotides of an PHOX2B gene, (iv) a gross chromosomal rearrangement of an PHOX2B gene, (v) a gross alteration in the level of a messenger RNA transcript of an PHOX2B gene, (vi) aberrant modification of an PHOX2B gene, such as of the methylation pattern of the genomic DNA, (vii) the presence of a non-wild type splicing pattern of a messenger RNA transcript of PHOX2B gene, (viii) a non-wild type level of an PHOX2B polypeptide, (ix) allelic loss of an PHOX2B gene, and/or (x) inappropriate post-translational modification of PHOX2B polypeptide.

The present invention provides several variants of polynucleotide sequence of SEQ ID No. 1. These variants comprise nucleic acid sequence of SEQ ID No:3, SEQ ID NO:4 and SEQ ID No:5. Only nucleic acid sequence of SEQ ID NO:3 contains a sequence polymorphism that is correlated with HSCR.

In a specific embodiment, the present invention is directed to an isolated nucleic acid molecule comprising the nucleic acid sequence of SEQ ID NO:1, wherein a nucleotide at position 2250 is substituted by a nucleotide base that is not adenine.

In another specific embodiment, the present invention is directed to an isolated nucleic acid molecule comprising the nucleic acid sequence of SEQ ID NO:1, wherein a nucleotide at position 3494 is substituted by a nucleotide base that is not adenine.

In another specific embodiment, the present invention is directed to an isolated nucleic acid molecule comprising the nucleic acid sequence of SEQ ID NO:1, wherein nucleotides from nucleotide positions 3511 to 3525 are deleted.

In another specific embodiment, the present invention is directed to an isolated nucleic acid molecule comprising at least 6 contiguous nucleotides of SEQ ID NO:1 including a nucleotide substitution at position 2250 by a nucleotide base that is not adenine.

In another specific embodiment, the present invention is directed to an isolated nucleic acid molecule comprising at least 6 contiguous nucleotides of SEQ ID NO:1 including a nucleotide substitution at position 3494 by a nucleotide base that is not adenine.

In another specific embodiment, the present invention is directed to an isolated nucleic acid molecule comprising at least 6 contiguous nucleotides of SEQ ID NO:1 including one or more nucleotides at positions 3511 to 3525.

In a specific embodiment, the present invention is directed to an isolated nucleic acid molecule comprising at least 6 contiguous nucleotides of SEQ ID NO:1 including a nucleotide substitution at position 2250 by a nucleotide base that is not adenine and that hybridizes to a nucleic acid molecule consisting of: (a) the nucleic acid sequence of SEQ ID NO:1; or (b) a nucleotide sequence that encodes the amino acid sequence of SEQ ID NO:2, under moderately stringent conditions, wherein the moderately stringent conditions comprise hybridization in 0.5 M $NaHPO_4$, 7% sodium dodecyl sulfate, 1 mM EDTA at 65° C., and washing in 0.5 M $NaHPO_4$, 7% sodium dodecyl sulfate, 1 mM EDTA at 65° C., and washing in 0.2×SSC/0.1% sodium dodecyl sulfate at 42° C., or the complement thereof.

In a specific embodiment, the present invention is directed to an isolated nucleic acid molecule comprising at least 6 contiguous nucleotides of SEQ ID NO:1 including a nucleotide substitution at position 3508 by a nucleotide base that is not adenine and that hybridizes to a nucleic acid molecule consisting of: (a) the nucleic acid sequence of SEQ ID NO:1; or (b) a nucleotide sequence that encodes the amino acid sequence of SEQ ID NO:2, under moderately stringent conditions, wherein the moderately stringent conditions comprise hybridization in 0.5 M NaHPO$_4$, 7% sodium dodecyl sulfate, 1 mM EDTA at 65° C., and washing in 0.5 M NaHPO$_4$, 7% sodium dodecyl sulfate, 1 mM EDTA at 65° C., and washing in 0.2×SSC/0.1% sodium dodecyl sulfate at 42° C., or the complement thereof.

In a specific embodiment, the present invention is directed to an isolated nucleic acid molecule comprising at least 6 contiguous nucleotides of SEQ ID NO:1 including one or more nucleotides at positions 3511 to 3525 and that hybridizes to a nucleic acid molecule consisting of: (a) the nucleic acid sequence of SEQ ID NO:1; or (b) a nucleotide sequence that encodes the amino acid sequence of SEQ ID NO:2, under moderately stringent conditions, wherein the moderately stringent conditions comprise hybridization in 0.5 M NaHPO$_4$, 7% sodium dodecyl sulfate, 1 mM EDTA at 65° C., and washing in 0.5 M NaHPO$_4$, 7% sodium dodecyl sulfate, 1 mM EDTA at 65° C., and washing in 0.2×SSC/0.1% sodium dodecyl sulfate at 42° C., or the complement thereof.

The present invention further provides a method of determining predisposition of a subject to HSCR comprising determining the presence of a polymorphism of the invention which is associated with HSCR. In another aspect, the present invention provides a method of determining predisposition of a subject to transmit HSCR. The method comprises identifying in a biological sample from a subject, a polymorphism or haplotype (a set of polymorphisms which is inherited together as a group) in the PHOX2B gene, as compared with a wild-type DNA from a non-HSCR subject. Certain polymorphisms or haplotypes may correlate with the severity and/or nature of the HSCR phenotype, e.g. with mild, moderate or severe aganglionosis as defined by established clinical parameters. Identification of polymorphisms may therefore be useful for prognosis of various degrees of the HSCR.

The PHOX2B gene is a homeobox gene and since the Homeobox genes are highly conserved among species, the present invention provides screening for related polymorphisms in all animals. The screening method can be utilized to identify animals carrying defects in genes like those which give rise to HSCR and neurodevelopmental disorders in humans. These animals may help to study disease progression and efficacies of treatment methods. These animals include, but are not limited to, non-primate (e.g., cows, pigs, horses, chickens, cats, dogs, rats, etc.), and primate (e.g. monkey such as acynomolgous monkey). The preferred mammal to be screened is human. In specific embodiment, the individuals screened are developmentally disabled children or adults in order to determine whether they carry mutations in the PHOX2B gene that are associated with HSCR. Similarly, the parents or relatives of disabled children may be screened to determine whether they are carriers of the mutated gene, hence may be diagnosed with increased risk of a predisposition or susceptibility associated with HSCR.

As used herein, "PHOX2B gene" refers to both the wild-type and mutants of the PHOX2B gene, which include: (a) a gene containing the DNA sequence shown in FIGS. 1A, 2, 3, or 4A; (b) any DNA sequence that encodes the amino acid sequence shown in FIGS. 1B or 4B; (c) any DNA sequence that hybridizes to the complement of the DNA sequences that encode the amino acid sequence shown in FIGS. 1A, 2, 3, or 4A, under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at page 2.10.3); or (d) any DNA sequence that hybridizes to the complement of the DNA sequences that encode the amino acid sequence shown in FIGS. 1A, 2, 3, or 4A, under moderately stringent conditions, e.g., hybridization in 0.5 M NaHPO$_4$, 7% sodium dodecyl sulfate, 1 mM EDTA at 65° C., and washing in 0.5 M NaHPO$_4$, 7% sodium dodecyl sulfate, 1 mMEDTA at 65° C., and washing in 0.2×SSC/0.1% sodium dodecyl sulfate at 42° C., (Ausubel et al., 1989, supra). In certain embodiments, the PHOX2B gene encodes a gene product functionally equivalent to a PHOX2B gene product encoded by sequences shown in FIGS. 1B or 4B.

In one embodiment of the invention, PHOX2B gene may also encompass fragments and degenerate variants of DNA sequences of (a) through (d), including naturally occurring variants thereof. The PHOX2B gene fragment may be a complementary DNA (cDNA) molecule or a genomic DNA molecule that may comprise one or more intervening sequences or introns, as well as regulating regions located beyond the 5' and 3' ends of the coding region or within an intron.

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide.

A PHOX2B gene sequence preferably exhibits at least about 80% overall similarity at the nucleotide level to the nucleic acid sequence depicted in FIGS. 1A, 2, 3, or 4A, more preferably exhibits at least about 85–90% overall similarity to the nucleic acid sequence in FIGS. 1A, 2, 3, or 4A and most preferably exhibits at least about 95% overall similarity to the nucleic acid sequence in FIGS. 1A, 2, 3, or 4A.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/ total number of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264–2268, modified as in Karlin and Altschul, 1993, Proc. Natl. Acad. Sci. U.S.A. 90:5873–5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to the nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389–3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11–17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted. The sequence alignment techniques as used above may also be used to predict corresponding polymorphisms in all mammals. Polymorphisms in any mammal, other than human, that correspond to the polymorphisms identified in the present invention may be used to correlate a disease phenotype, such as HSCR, with the corresponding polymorphism in the mammal.

The PHOX2B gene sequences of the invention are preferably of mammalian origin, and most preferably human. Mammals, include but are not limited to, mice, rats, cats, dogs, cattle, pigs, sheep, guinea pigs and rabbits.

The invention also encompasses nucleic acid molecules encoding mutant PHOX2B, peptide fragments of PHOX2B, truncated PHOX2B, and PHOX2B fusion proteins.

The PHOX2B gene sequences of the invention further include isolated nucleic acid molecules which hybridize under highly stringent or moderate stringent conditions to at least about 6, preferably about 12, more preferably about 18, consecutive nucleotides of the PHOX2B gene sequences of (a) through (d).

The invention also includes nucleic acid molecules, preferably DNA molecules, that hybridize to, and are therefore the complements of, the DNA sequences (a) through (d), in the preceding paragraph. Such hybridization conditions may be highly stringent or moderately stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as PHOX2B gene antisense molecules useful, for example, in PHOX2B gene regulation. With respect to PHOX2B gene regulation, such techniques can be used to modulate, for example, the phenotype of HSCR. Further, such sequences may be used as part of ribozyme and/or triple helix sequences, also useful for PHOX2B gene regulation.

5.2. Screening for Mutations in the PHOX2B Gene

The present invention provides diagnostic screening of a population for pre-disposition or susceptibility to increased risk for HSCR resulting from aberrant expression of PHOX2B gene. In particular, the screening relates to detecting a polymorphism in the PHOX2B gene. With knowledge of the mutation of the PHOX2B gene as disclosed herein, diagnostic information from the screening may be used in various ways. For example, the screening may be useful in assisting the medical diagnosis of a symptomatic patient or screening for presymptomatic individuals, including prenatal diagnosis. In this application, a patient with a high probability for being affected with HSCR could be tested with the gene-based diagnostic. A positive result would show that the individual may be a carrier of HSCR or that the individual is suceptable to HSCR. Also, first degree relatives of newly diagnosed presymptomatic or symptomatic HSCR individuals may be screened and determine whether these individuals are at a higher risk for disease and, if identified, could benefit from therapeutic intervention. Once identified, such individuals could be targeted for preventative treatment with the therapeutic compositions of the invention. It may also result in substantially different management, especially prevention and treatment, with subsequent substantial improvement in mortality and morbidity from HSCR, especially in at risk populations.

The diagnostic methods of the present invention are particularly useful in combination with a subject's family history of HSCR. For example, a parent suffering from HSCR and who has a family history of HSCR, may well have a child who is susceptible to HSCR, but who has not yet shown symptoms. To alleviate the concern of the parent, as well as the child, and to take any preventive measures which might delay or prevent onset, methods of the present invention can be used to determine whether the child is a carrier of a PHOX2B mutation associated with HSCR. If so, further testing can be performed, for example, neurological tests, clinical diagnosis such as diagnosing the symptoms of HSCR including but not limited to intestinal obstruction, constipation, vomiting, abdominal distension, enterocolitis, diarrhea, fever, septic shock, to provide further support for the predicted susceptibility.

Since marker by marker approach ignores the polygenic nature of HSCR and does not take into account possible interactions among susceptibility genes, sets of SNPs in the different susceptibility loci described for HSCR may be used to screen for HSCR in a population. Accordingly, one embodiment of the present invention is directed to assembling an extensive catalogue of SNPs in candidate genes for HSCR, including but not limited to RET, EDNRB, EDN3 and GDNF genes, for use in diagnosing, screening, and/or staging the population for different degrees of HSCR manifestation by considering mutations in all the candidate genes together.

Accordingly, in one embodiment, the present invention provides a method of screening or diagnosing, or staging HSCR in a subject. The method comprises (a) providing a biological sample from the subject; and (b) testing the sample for the presence of mutation in one or more genes selected from the group consisting of PHOX2B, RET, EDNRB, EDN3 and GDNF, wherein mutations in the PHOX2B gene and one or more genes indicate that the subject is genetically predisposed to HSCR.

Polymorphisms in the PHOX2B gene may be used as genetic markers for genetic mapping. The polymorphisms of the invention may be used in a number of methods including but not limited to, identifying or determining the source of a genetic sample, or correlate a test sample with a biological sample, including but not limited to, uses in forensic testing and paternity testing, use in the study of population genetics, such as evolution, origin of a given race, and population migration.

Accordingly, in an embodiment, the invention is directed to a method of determining the source of a first biological sample from a subject compared to a second biological sample. The method comprises: (a) providing a first biological sample from the subject; (b) testing the first biological sample for the presence of a mutation of the PHOX2B gene at nucleotide positions 2250, 3508, and/or 3511–3525 of SEQ ID NO:1; (c) testing the second biological sample for the presence of a mutation of the PHOX2B gene at nucleotide positions 2250, 3508, and/or 3511–3525 of SEQ ID NO:1; and (d) comparing the mutations present in step (b) and (c); wherein the presence of identical mutation in the first biological sample compared to the second biological sample indicates that the first and second biological samples are obtained from an identical source.

As discussed in Section 2.3, polymorphisms exist in different individuals of a population. These polymorphisms are refer to as polymorphic forms. Determination of which polymorphic forms occupy a set of polymorphic sites in an individual identifies a set of polymorphic forms that distinguishes the individual. See generally National Research Council, The Evaluation of Forensic DNA Evidence (Eds. Pollard et al., National Academy Press, DC, 1996). Since polymorphic sites are generally within a 50,000 bp region in the human genome, the probability of recombination between these polymorphic sites is low. That low probability means the haplotype (a set of polymorphic sites) should be inherited without change for at least several generations. The more sites that are analyzed, the lower the probability that the set of polymorphic forms in one individual is the same as that in an unrelated individual. Preferably, if multiple sites are analyzed, the sites are unlinked.

The capacity to identify a distinguishing or unique set of forensic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance. For calculation of the probability that two random individuals have the same polymorphic or allelic form at a given polymorphic site, see WO 95/12607. If several polymorphic loci are tested, the cumulative probability of non-identity for random individuals becomes very high (e.g., one billion to one). Such probabilities can be taken into account together with other evidence in determining the guilt or innocence of the suspect.

Polymorphisms in the PHOX2B gene may be used in paternity testing. The object of paternity testing is usually to determine whether a male is the father of a child. In most cases, the mother of the child is known and thus, the mother's contribution to the child's genotype can be traced. Paternity testing investigates whether the part of the child's genotype not attributable to the mother is consistent with that of the putative father. Paternity testing can be performed by analyzing sets of polymorphisms in the putative father and the child. If the set of polymorphisms in the child attributable to the father does not match the putative father, it can be concluded, barring experimental error, that the putative father is not the biological father. If the set of polymorphisms in the child attributable to the father does match the set of polymorphisms of the putative father, a statistical calculation can be performed to determine the probability of coincidental match. For calculation of the probability of parentage exclusion, (representing the probability that a random male will have a polymorphic form at a given polymorphic site that makes him incompatible as the father), see WO 95/12607. If several polymorphic loci are included in the analysis, the cumulative probability of exclusion of a random male is very high. This probability can be taken into account in assessing the liability of a putative father whose polymorphic marker set matches the child's polymorphic marker set attributable to his/her father.

Individuals carrying mutations in the PHOX2B gene may be detected at either the DNA, the RNA, or the protein level using a variety of techniques, such as, e.g., Southern, Northern, in situ hybridization, and PCR. A biological sample is isolated from a mammal and then tested for the presence of a mutated gene or a product thereof. In a specific embodiment, the sample is tested for the presence of a polymorphism which is associated with HSCR. In another embodiment, the sample is tested for a polymorphism which matches that of another sample. The genomic DNA used for the diagnosis may be obtained from body cells, such as those present in peripheral blood, urine, saliva, bucca, surgical specimen, and autopsy specimens. In preferred embodiments, biological samples suitable for testing include blood, saliva, amniotic fluid, and tissue. The most preferred biological sample is blood. However, any biological sample from which genetic material or the products of the marker genes can be isolated is suitable.

5.2.1. Nucleic Acid Based Screening

The DNA may be used directly or may be amplified enzymatically in vitro through use of PCR (Saiki et al. *Science* 239:487–491 (1988)) or other in vitro amplification methods such as the ligase chain reaction (LCR) (Wu and Wallace *Genomics* 4:560–569 (1989)), strand displacement amplification (SDA) (Walker et al. *Proc. Natl. Acad. Sci. U.S.A.* 89:392–396 (1992)), self-sustained sequence replication (3SR) (Fahy et al. *PCR Methods Appl.* 1:25–33 (1992)), prior to mutation analysis. The methodology for preparing nucleic acids in a form that is suitable for mutation detection is well known in the art.

The detection of mutations in specific DNA sequences, such as the PHOX2B gene, can be accomplished by a variety of methods including, but not limited to, restriction-fragment-length-polymorphism detection based on allele-specific restriction-endonuclease cleavage (Kan and Dozy, 1978, Lancet ii:910–912), hybridization with allele-specific oligonucleotide probes (Wallace et al., 1978 Nucl Acids Res 6:3543–3557), including immobilized oligonucleotides (Saiki et al., 1989 Proc. Natl. Acad. Sci. U.S.A. 86:6230–6234) or oligonucleotide arrays (Maskos and Southern, 1993, Nucl Acids Res 21:2269–2270), allele-specific PCR (Newton et al., 1989, Nucl Acids Res 17:2503–2516), mismatch-repair detection (MRD) (Faham and Cox, 1995, Genome Res 5:474–482), binding of MutS protein (Wagner et al., 1995, Nucl Acids Res 23:3944–3948), denaturing-gradient gel electrophoresis (DGGE) (Fisher and Lerman et al., 1983, Proc. Natl. Acad. Sci. U.S.A. 80:1579–1583), single-strand-conformation-polymorphism detection (Orita et al., 1983, Genomics 5:874–879), RNAase cleavage at mismatched base-pairs (Myers et al., 1985, Science 230:1242), chemical (Cotton et al. *Proc. Natl. Acad. Sci. U.S.A.* 85:4397–4401 (1988)) or enzymatic (Youil et al. *Proc. Natl. Acad. Sci. U.S.A.* 92:87–91 (1995)) cleavage of heteroduplex DNA, methods based on allele specific primer extension (Syvänen et al. *Genomics* 8:684–692 (1990)), genetic bit analysis (GBA) (Nikiforov et al. *Nuci Acids Res* 22:4167–4175 (1994)), the oligonucleotide-ligation assay (OLA) (Landegren et al. *Science* 241:1077 (1988)), the allele-specific ligation chain reaction (LCR) (Barrany *Proc. Natl. Acad. Sci. U.S.A.* 88:189–193 (1991)), gap-LCR (Abravaya et al. *Nucl Acids Res* 23:675–682 (1995)), and radioactive and/or fluorescent DNA sequencing using standard procedures well known in the art.

In preferred embodiments, screening for mutated nucleic acids can be accomplished by direct sequencing of nucleic acids. In fact, putative mutants identified by other methods may be sequenced to determine the exact nature of the mutation. Nucleic acid sequences can be determined through a number of different techniques which are well known to those skilled in the art, such as but not limited to, RNA or DNA chip hybridization. Fodor et al., 1993, Nature 364: 555–556; Pease, 1994, Proc. Natl. Acad. Sci. USA 91(11): 5022–5026. In order to sequence the nucleic acid, sufficient copies of the material must first be amplified. In preferred embodiments, amplification of a selected, or target, nucleic acid sequence may be carried out by any suitable means. See generally Kwoh, D. and Kwoh, T., Am Biotechnol Lab, 8, 14 (1990). Examples of suitable amplification techniques include, but are not limited to, polymerase chain reaction, ligase chain reaction (see Barany, Proc Natl Acad Sci USA 88, 189 (1991), strand displacement amplification (see generally Walker, G. et al., Nucleic Acids Res. 20, 1691 (1992); Walker. G. et al., Proc Natl Acad Sci USA 89, 392 (1992), transcription-based amplification (see Kwoh, D. et al., Proc Natl Acad Sci USA, 86, 1173 (1989), self-sustained sequence replication (or "3SR") (see Guatelli, J. et al., Proc Natl Acad Sci USA, 87, 1874 (1990), the replicase system (see Lizardi, P. et al., Biotechnology, 6, 1197 (1988), nucleic acid sequence-based amplification (or "NASBA") (see Lewis, R., Genetic Engineering News, 12(9), 1 (1992), the repair chain reaction (or "RCR") (see Lewis, R., Genetic Engineering News, 12(9), 1 (1992), and boomerang DNA amplification (or "BDA")(see Lewis, R., Genetic Engineering News, 12(9), 1 (1992). In a most preferred embodiment, polymerase chain reaction is used.

Single strand polymorphism assay ("SSPA") analysis and the closely related heteroduplex analysis methods may be used for screening for single-base polymorphisms (Orita, M. et al., Proc Natl Acad Sci USA, 86, 2766 (1989). In these methods, the mobility of PCR-amplified test DNA from clinical specimens is compared with the mobility of DNA amplified from normal sources by direct electrophoresis of samples in adjacent lanes of native polyacrylamide or other types of matrix gels. Single-base changes often alter the secondary structure of the molecule sufficiently to cause slight mobility differences between the normal and mutant PCR products after prolonged electrophoresis. The presence of polymorphisms, including mutations, in nucleic acids by using mass spectrometry may be used as discussed in U.S. Pat. No: 5,869,242.

Ligase chain reaction is yet another method of screening for mutated nucleic acids. Ligase chain reaction (LCR) is also carried out in accordance with known techniques. LCR is especially useful to amplify, and thereby detect, single nucleotide differences between two DNA samples. In general, the reaction involves two pairs of oligonucleotide probes: one pair binds to one strand of the sequence to be detected; the other pair binds to the other strand of the sequence to be detected. The reaction is carried out by, first, denaturing (e.g., separating) the strands of the sequence to be detected, then reacting the strands with the two pairs of oligonucleotide probes in the presence of a heat stable ligase so that each pair of oligonucleotide probes hybridize to target DNA and, if there is perfect complementarity at their junction, adjacent probes are ligated together. The hybridized molecules are then separated under denaturation conditions. The process is cyclically repeated until the sequence has been amplified to the desired degree. Detection may then be carried out in a manner like that described above with respect to PCR.

Southern hybridization is also an effective method of identifying differences in sequences. Hybridization conditions, such as salt concentration and temperature can be adjusted for the sequence to be screened. Southern blotting and hybridizations protocols are described in Current Protocols in Molecular Biology (Greene Publishing Associates and Wiley-Interscience), pages 2.9.1–2.9.10. Probes can be labelled for hybridization with random oligomers (primarily 9-mers) and the Klenow fragment of DNA polymerase. Very high specific activity probe can be obtained using commercially available kits such as the Ready-To-Go DNA Labelling Beads (Pharmacia Biotech), following the manufacturer's protocol. Briefly, 25 ng of DNA (probe) is labelled with $^{32}$P-dCTP in a 15 minute incubation at 37° C. Labelled probe is then purified over a ChromaSpin (Clontech) nucleic acid purification column. Possible competition of probes having high repeat sequence content, and stringency of hybridization and washdown will be determined individually for each probe used. Alternatively, fragments of a candidate gene may be generated by PCR, the specificity may be verified using a rodent-human somatic cell hybrid panel, and subcloning the fragment. This allows for a large prep for sequencing and use as a probe. Once a given gene fragment has been characterized, small probe preps can be done by gel or column purifying the PCR product.

These mismatch detection protocols use samples generated by PCR and thus require use of very little genomic template. All of these methods can provide clues regarding the location of the sequence change which leads to the appearance of anomalous bands, hence facilitating subsequent cloning and sequencing strategies.

Methods of screening for mutated nucleic acids can be carried out using either deoxyribonucleic acids ("DNA") or messenger ribonucleic acids ("mRNA") isolated from the biological sample.

In specific embodiments, DNA amplification techniques that may be used involve the use of a probe, a pair of probes, or two pairs of probes which specifically bind to DNA encoding the gene of interest, but do not bind to DNA which does not encode the gene, under the same hybridization conditions, and which serve as the primer or primers for the amplification of the gene of interest or a portion thereof in the amplification reaction.

Identification of a sequence polymorphism may be effected by conventional sequencing and sequence analysis techniques, for example as described in Cotton, R. G. H., Mutation Detection, Oxford University Press, 1997; Landegren, U., Laboratory Protocols for Mutation Detection, Oxford University Press; and R. G. H. Cotton et al, Mutation Detection, Oxford, University Press, 1998. In preferred embodiments, nucleic acid sequencing can be performed by chemical or enzymatic method. The enzymatic method relies on the ability of DNA polymerase to extend a primer, hybridized to the template to be sequenced, until a chain-terminating nucleotide is incorporated. In a preferred embodiment, the methods utilize didoexynucleotides. Primers may be labelled with radioactive or fluorescent labels. Various DNA polymerases are available including Klenow fragment, AMV reverse transcriptase, Thermus aquaticus DNA polymerase, and modified T7 polymerase.

Oligonucleotides useful in diagnostic assays are typically at least 6 consecutive nucleotides in length, and may range at least 6, 7, 8, 9, 10, 11, 12, 13, 14, 15, 16, 17, or 18 nucleotides in length. Such oligonucleotides can be derived from either the PHOX2B genomic or cDNA sequences.

A further aspect of the invention is an oligonucleotide of at least 8 nucleotides in length selected from nucleotides 1-46, 48-123; 120-369; 365-394; 390-540; 538-646; 643-1004; 1001-1080; 1083-1109; 1106-1304; 1301-1366; 1363-1386; 1389-1514; 1516-1778; 1773-1917; 1921-2010; 2051-2146; 2154-2209; 2234-2368; 2367-2422; 2420-2464; 2465-2491; 2488-2568; 2872-2901; 2902-2934; 2936-2954; 2449-3001; 3000-3042; 3420-3435; 3451-3708; 3703-3754; 3750-3770; 3774-3840; 3840-3962; 3964-3978; 3974-3992; 3990-4157; 4153-4251; 4257-4282; 4284-4321; 4316-4333; 4337-4391; 4386-4400; 4398-4436; 4444-4547; 4572-4714; 4709-4777; 5165-5397; and 5394-5508 of SEQ ID NO:1, 3, or 4; or the reverse complement thereof.

A further aspect of the invention is an oligonucleotide of at least 9 nucleotides in length selected from nucleotides 1-47; 47-124; 119-370; 364-395; 389-541; 537-647; 642-1005; 1000-1081; 1082-1110; 1105-1305; 1300-1367; 1362-1387; 1388-1515; 1515-1918; 1920-2011; 2050-2147; 2153-2210; 2233-2369; 2366-2423; 2419-2465; 2464-2492; 2487-2569; 2871-2935; 2935-3002; 2999-3043; 3419-3436; 3450-3755; 3749-3771; 3773-3841; 3839-3963; 3963-3979; 3973-3993; 3989-4158; 4152-4252; 4256-4283; 4283-4334; 4336-4401; 4397-4437; 4443-4548; 4571-4778; 5164-5398; and 5393-5508 of SEQ ID NO:1, 3, or 4; or the reverse complement thereof.

A further aspect of the invention is an oligonucleotide of at least 10 nucleotides in length selected from nucleotides 1-48; 46-125; 118-1006; 999-1082; 1081-1111; 1104-1306; 1299-1368; 1361-1388; 1387-1516; 1514-1919; 1919-2012; 2049-2148; 2152-2211; 2232-2370 2365-2424; 2418-2466; 2463-2493; 2486-2570; 2870-2936; 2934-3003; 2998-3044; 3418-3437; 3449-3772; 3772-3842; 3838-3964; 3962-3994; 3988-4284; 4282-4335; 4335-4402; 4396-4438; 4442-4549; 4570-4779; and 5163-5508 of SEQ ID NO:1, 3, or 4; or the reverse complement thereof.

A further aspect of the invention is an oligonucleotide of at least 11 nucleotides in length selected from nucleotides 1-49; 45-1389; 1386-1517, 1513-1920; 1918-2013; 2048-2149; 2151-2212; 2231-2371; 2364-2425; 2417-2467; 2462-2571; 2869-2937; 2933-3004; 2997-3045; 3417-3438; 3448-3773; 3771-3843; 3837-3965; 3961-3995; 3987-4285; 4281-4336; 4334-4403; 4395-4439; 4441-4550; 4569-4780; and 5162-5508 of SEQ ID NO:1, 3, or 4; or the reverse complement thereof.

A further aspect of the invention is an oligonucleotide of at least 12 nucleotides in length selected from nucleotides 1-50, 44-1390; 1385-1518; 1512-1921; 1917-2014; 2047-2150; 2150-2213; 2230-2372; 2363-2468; 2461-2572; 2868-2938; 2932-3005; 2996-3046; 3416-3439; 3447-3774; 3770-3844; 3836-3966; 3960-4286; 4280-4337; 4333-4440; 4440-4551; 4568-4781; and 5161-5508 of SEQ ID NO:1, 3, or 4; or the reverse complement thereof.

A further aspect of the invention is an oligonucleotide of at least 13 nucleotides in length selected from nucleotides 1-51; 43-1391; 1384-1519; 1511-1922; 1916-2015; 2046-2151; 2149-2214; 2229-2469; 2460-2573; 2867-2939; 2931-3047; 3415-3440; 3446-3775; 3769-3845; 3835-3967; 3959-4287; 4279-4338; 4332-4441; 4439-4552; 4567-4782; and 5160-5508 of SEQ ID NO:1, 3, or 4; or the reverse complement thereof.

A further aspect of the invention is an oligonucleotide of at least 14 nucleotides in length selected from nucleotides 1-52; 42-1392; 1383-1520; 1510-1923; 1915-2016; 2045-2152; 2148-2215; 2228-2574; 2866-2940; 2930-3048; 3414-3441; 3445-3776; 3768-3968; 3959-4288; 4278-4339; 4331-4442; 4438-4553; 4566-4783; and 5159-5508 of SEQ ID NO:1, 3, or 4; or the reverse complement thereof.

A further aspect of the invention is an oligonucleotide of at least 15 nucleotides in length selected from nucleotides 1-53; 41-1393; 1382-1521; 1509-1924; 1914-2017; 2044-2153; 2147-2216; 2227-2575; 2865-2942; 2929-3049; 3413-3442; 3444-3777; 3767-3969; 3958-4289; 4277-4340; 4330-4443; 4437-4554; 4565-4784; and 5158-5508 of SEQ ID NO:1, 3, or 4; or the reverse complement thereof.

A further aspect of the invention is an oligonucleotide of at least 16 nucleotides in length selected from nucleotides 1-1394; 1381-1925; 1913-2018; 2043-2154; 2146-2217; 2226-2576; 2864-3050; 3412-3443; 3443-3778; 3766-4341; 4329-4444; 4436-4555; 4564-4785; and 5157-5508 of SEQ ID NO:1, 3, or 4; or the reverse complement thereof.

A further aspect of the invention is an oligonucleotide of at least 17 nucleotides in length selected from nucleotides 1-1926; 1912-2019; 2042-2155; 2145-2218; 2225-2577; 2863-3051; 3411-3779; 3765-4342; 4329-4445; 4435-4556; 4563-4786; and 5156-5508 of SEQ ID NO:1, 3, or 4; or the reverse complement thereof.

A further aspect of the invention is an oligonucleotide of at least 18 nucleotides in length selected from nucleotides 1-2020; 2041-2156; 2144-2219; 2224-2578; 2862-3052; 3410-3780; 3764-4446; 4434-4557; 4562-4787; and 5155-5508 of SEQ ID NO:1, 3, or 4; or the reverse complement thereof.

A further aspect of the invention is an oligonucleotide of at least 8 nucleotides in length selected from nucleotides 1-46, 48-123; 120-369; 365-394; 390-540; 538-646; 643-1004; 1001-1080; 1083-1109; 1106-1304; 1301-1366; 1363-1386; 1389-1514; 1516-1778; 1773-1917; 1921-2010; 2051-2146; 2154-2209; 2234-2368; 2367-2422; 2420-2464; 2465-2491; 2488-2568; 2872-2901; 2902-2934; 2936-2954;

2449-3001; 3000-3042; 3420-3435; 3451-3708; 3703-3754; 3750-3770; 3774-3840; 3840-3962; 3964-3978; 3974-3992; 3990-4157; 4153-4251; 4257-4282; 4284-4321; 4316-4333; 4337-4391; 4386-4400; 4398-4436; 4444-4547; 4572-4714; 4709-4777; 5165-5397; and 5394-5493 of SEQ ID NO:5; or the reverse complement thereof.

A further aspect of the invention is an oligonucleotide of at least 9 nucleotides in length selected from nucleotides 1-47; 47-124; 119-370; 364-395; 389-541; 537-647; 642-1005; 1000-1081; 1082-1110; 1105-1305; 1300-1367; 1362-1387; 1388-1515; 1515-1918; 1920-2011; 2050-2147; 2153-2210; 2233-2369; 2366-2423; 2419-2465; 2464-2492; 2487-2569; 2871-2935; 2935-3002; 2999-3043; 3419-3436; 3450-3755; 3749-3771; 3773-3841; 3839-3963; 3963-3979; 3973-3993; 3989-4158; 4152-4252; 4256-4283; 4283-4334; 4336-4401; 4397-4437; 4443-4548; 4571-4778; 5164-5398; and 5393-5493 of SEQ ID NO:5; or the reverse complement thereof.

A further aspect of the invention is an oligonucleotide of at least 10 nucleotides in length selected from nucleotides 1-48; 46-125; 118-1006; 999-1082; 1081-1111; 1104-1306; 1299-1368; 1361-1388; 1387-1516; 1514-1919; 1919-2012; 2049-2148; 2152-2211; 2232-2370 2365-2424; 2418-2466; 2463-2493; 2486-2570; 2870-2936; 2934-3003; 2998-3044; 3418-3437; 3449-3772; 3772-3842; 3838-3964; 3962-3994; 3988-4284; 4282-4335; 4335-4402; 4396-4438; 4442-4549; 4570-4779; and 5163-5493 of SEQ ID NO:5; or the reverse complement thereof.

A further aspect of the invention is an oligonucleotide of at least 11 nucleotides in length selected from nucleotides 1-49; 45-1389; 1386-1517, 1513-1920; 1918-2013; 2048-2149; 2151-2212; 2231-2371; 2364-2425; 2417-2467; 2462-2571; 2869-2937; 2933-3004; 2997-3045; 3417-3438; 3448-3773; 3771-3843; 3837-3965; 3961-3995; 3987-4285; 4281-4336; 4334-4403; 4395-4439; 4441-4550; 4569-4780; and 5162-5493 of SEQ ID NO:5; or the reverse complement thereof.

A further aspect of the invention is an oligonucleotide of at least 12 nucleotides in length selected from nucleotides 1-50, 44-1390; 1385-1518; 1512-1921; 1917-2014; 2047-2150; 2150-2213; 2230-2372; 2363-2468; 2461-2572; 2868-2938; 2932-3005; 2996-3046; 3416-3439; 3447-3774; 3770-3844; 3836-3966; 3960-4286; 4280-4337; 4333-4440; 4440-4551; 4568-4781; and 5161-5493 of SEQ ID NO:5; or the reverse complement thereof.

A further aspect of the invention is an oligonucleotide of at least 13 nucleotides in length selected from nucleotides 1-51; 43-1391; 1384-1519; 1511-1922; 1916-2015; 2046-2151; 2149-2214; 2229-2469; 2460-2573; 2867-2939; 2931-3047; 3415-3440; 3446-3775; 3769-3845; 3835-3967; 3959-4287; 4279-4338; 4332-4441; 4439-4552; 4567-4782; and 5160-5493 of SEQ ID NO:5; or the reverse complement thereof.

A further aspect of the invention is an oligonucleotide of at least 14 nucleotides in length selected from nucleotides 1-52; 42-1392; 1383-1520; 1510-1923; 1915-2016; 2045-2152; 2148-2215; 2228-2574; 2866-2940; 2930-3048; 3414-3441; 3445-3776; 3768-3968; 3959-4288; 4278-4339; 4331-4442; 4438-4553; 4566-4783; and 5159-5493 of SEQ ID NO:5; or the reverse complement thereof.

A further aspect of the invention is an oligonucleotide of at least 15 nucleotides in length selected from nucleotides 1-53; 41-1393; 1382-1521; 1509-1924; 1914-2017; 2044-2153; 2147-2216; 2227-2575; 2865-2942; 2929-3049; 3413-3442; 3444-3777; 3767-3969; 3958-4289; 4277-4340; 4330-4443; 4437-4554; 4565-4784; and 5158-5493 of SEQ ID NO:5; or the reverse complement thereof.

A further aspect of the invention is an oligonucleotide of at least 16 nucleotides in length selected from nucleotides 1-1394; 1381-1925; 1913-2018; 2043-2154; 2146-2217; 2226-2576; 2864-3050; 3412-3443; 3443-3778; 3766-4341; 4329-4444; 4436-4555; 4564-4785; and 5157-5493 of SEQ ID NO:5; or the reverse complement thereof.

A further aspect of the invention is an oligonucleotide of at least 17 nucleotides in length selected from nucleotides 1-1926; 1912-2019; 2042-2155; 2145-2218; 2225-2577; 2863-3051; 3411-3779; 3765-4342; 4329-4445; 4435-4556; 4563-4786; and 5156-5493 of SEQ ID NO:5; or the reverse complement thereof.

A further aspect of the invention is an oligonucleotide of at least 18 nucleotides in length selected from nucleotides 1-2020; 2041-2156; 2144-2219; 2224-2578; 2862-3052; 3410-3780; 3764-4446; 4434-4557; 4562-4787; and 5155-5493 of SEQ ID NO:5; or the reverse complement thereof.

It will be appreciated that such preferred oligonucleotides can be a part of a kit for detecting polymorphisms in the PHOX2B gene, especially for the detection of polymorphisms in PHOX2B DNA or RNA in a patient sample. As will be appreciated, the mutation analysis may also be performed on samples of RNA by reverse transcription into cDNA therefrom. The kit of the present invention may be used for the identification, analysis and typing of polymorphic DNA according to the present methods. Kits according to the present invention may comprise a carrying means being compartmentalized to receive in close confinement therein one or more containers such as vials, tubes, bottles and the like. Each of such containers may comprise components or a mixture of components needed to perform genotyping analysis. Optionally associated with such container(s) can be a notice in the form prescribed by a governmental agency regulating the manufacture, use or sale of pharmaceuticals or diagnostic products, which notice reflects approval by the agency of manufacture, use or sale for human administration.

5.2.2. Protein Based Screening

Mutations may also be detected at the protein level using antibodies specific for the mutant PHOX2B protein. It may also be possible to base an PHOX2B mutation assay on altered cellular or subcellular localization of the mutant form of the PHOX2B protein. Alternatively, the detection of a mutated gene associated with HSCR can be carried out by collecting a biological sample and testing for the presence or form of the protein produced by the gene. The mutation in the gene may result in the production of a mutated form of the peptide or the lack of production of the gene product.

In an embodiment, the determination of the presence of the mutant PHOX2B protein can be carried out, for example, by isoelectric focusing, protein sizing, or immunoassay. In an immunoassay, an antibody that selectively binds to the mutated protein can be utilized (for example, an antibody that selectively binds to the mutated form of PHOX2B encoded protein). Such methods for isoelectric focusing and immunoassay are well known in the art, and are discussed in further detail below.

Changes in the size or charge of the polypeptide can be identified by isoelectric focusing or protein sizing techniques. Changes resulting in amino acid substitutions, where the substituted amino acid has a different charge than the original amino acid, can be detected by isoelectric focusing. Isoelectric focusing of the polypeptide through a gel having an ampholine gradient at high voltages separates proteins by their pI. The pH gradient gel can be compared to a simultaneously run gel containing the wild-type protein. Protein sizing techniques such as protein electrophoresis and sizing chromatography can also be used to detect changes in the size of the product.

As an alternative to isoelectric focusing or protein sizing, the step of determining the presence of the mutated polypeptides in a sample may be carried out by an antibody assay with an antibody which selectively binds to the mutated polypeptides (i.e., an antibody which binds to the mutated polypeptides but exhibits essentially no binding to the wild-type polypeptide without the polymorphism in the same binding conditions).

Antibody assays may, in general, be homogeneous assays or heterogeneous. In a homogeneous assay, the immunological reaction usually involves the specific antibody, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include, but are not limited to, free radicals, radioisotopes, fluorescent dyes, enzymes, bacteriophages, and coenzymes.

In a heterogeneous assay approach, the reagents are usually the specimen, the antibody of the invention and means for producing a detectable signal. Similar specimens as described above may be used. The antibody is generally immobilized on a support, such as a bead, plate, or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include, but are not limited to, the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Those skilled in the art will be familiar with numerous specific immunoassay formats and variations thereof which may be useful for carrying out the method disclosed herein. See U.S. Pat. Nos. 4,727,022, 4,659,678, 4,376,110, 4,275,149, 4,233,402, and 4,230,767.

Antibodies to distinct isoforms of the PHOX2B gene (i.e., wild-type or mutant-specific antibodies) can be used to detect the presence or absence of the wild-type or mutant gene products by immunoblotting (Western blotting) or other immunostaining methods. Thus, in accordance with another aspect of the present invention, a kit is provided that is suitable for use in screening and assaying for the presence of the PHOX2B gene by an immunoassay through the use of an antibody which specifically binds to a gene product of the PHOX2B gene in combination with a reagent for detecting the binding of the antibody to the gene product.

5.3. Correlation of Polymorphisms with Phenotypic Traits

The polymorphisms described in the present invention may contribute to the phenotype of an organism in different ways. Some polymorphisms occur within a protein coding sequence and contribute to phenotype by affecting protein structure. The effect may be neutral, beneficial or detrimental, or both beneficial and detrimental, depending on the circumstances. For example, a heterozygous sickle cell mutation confers resistance to malaria, but a homozygous sickle cell mutation is usually lethal. Other polymorphisms occur in noncoding regions but may exert phenotypic effects indirectly via influence on replication, transcription, and translation. A single polymorphism may affect more than one phenotypic trait. Likewise, a single phenotypic trait may be affected by polymorphisms in different genes. Further, some polymorphisms predispose an individual to a distinct mutation that is causally related to a certain phenotype.

Phenotypic traits include diseases that have known but unmapped genetic components. Phenotypic traits also include symptoms of, or susceptibility to, multifactorial diseases of which a component is or may be genetic, such as autoimmune diseases, inflammation, cancer, diseases of the nervous system, and infection by pathogenic microorganisms. Some examples of autoimmune diseases include rheumatoid arthritis, multiple sclerosis, diabetes (insulin-dependent and non-independent), systemic lupus erythematosus and Graves disease. Some examples of cancers include cancers of the bladder, brain, breast, colon, esophagus, kidney, leukemia, liver, lung, oral cavity, ovary, pancreas, prostate, skin, stomach and uterus. Phenotypic traits also include characteristics such as longevity, appearance (e.g., baldness, obesity), strength, speed, endurance, fertility, and susceptibility or receptivity to particular drugs or therapeutic treatments. In the present invention, a particular polymorphism is related to predisposition or susceptibility to HSCR. More specifically, certain polymorphisms in the PHOX2B gene is related to neural crest derived congenital malformation.

Correlation is performed for a population of individuals who have been tested for the presence or absence of a phenotypic trait of interest and for polymorphic marker sets. To perform such analysis, the presence or absence of a set of polymorphisms (i.e. a polymorphic set) is determined for a set of individuals, some of whom exhibit a particular trait, and some of which exhibit lack of the trait. The alleles of each polymorphism of the set are then reviewed to determine whether the presence or absence of a particular allele is associated with the trait of interest. Correlation can be performed by standard statistical methods such as a $X^2$ test and statistically significant correlations between polymorphic form(s) and phenotypic characteristics are noted. For example, it might be found that the presence of allele A1 at polymorphism A correlates with heart disease. As a further example, it might be found that the combined presence of allele A1 at polymorphism A and allele B1 at polymorphism B correlates with increased milk production of a farm animal.

Such correlations can be exploited in several ways. In the case of a strong correlation between a set of one or more polymorphic forms and a disease for which treatment is available, detection of the polymorphic form set in a human or animal patient may justify immediate administration of treatment, or at least the institution of regular monitoring of the patient. Detection of a polymorphic form correlated with serious disease in a couple contemplating a family may also be valuable to the couple in their reproductive decisions. For example, the female partner might elect to undergo in vitro fertilization to avoid the possibility of transmitting such a polymorphism from her husband to her offspring. In the case of a weaker, but still statistically significant correlation between a polymorphic set and human disease, immediate therapeutic intervention or monitoring may not be justified. Nevertheless, the patient can be motivated to begin simple life-style changes (e.g., diet, exercise) that can be accomplished at little cost to the patient but confer potential benefits in reducing the risk of conditions to which the patient may have increased susceptibility by virtue of variant alleles. Identification of a polymorphic set in a patient correlated with enhanced receptiveness to one of several treatment regimes for a disease indicates that this treatment regime should be followed.

For animals and plants, correlations between characteristics and phenotype are useful for breeding for desired characteristics. For example, Beitz et al., U.S. Pat. No. 5,292,639 discuss use of bovine mitochondrial polymorphisms in a breeding program to improve milk production in cows.

5.4. Genetic Mapping of Phenotypic Traits

The present section describes identification of a physical linkage between a genetic locus associated with a trait of interest and polymorphic markers that are not associated with the trait, but are in physical proximity with the genetic locus responsible for the trait and co-segregate with it. Such analysis is useful for mapping a genetic locus associated with a phenotypic trait to a chromosomal position, and thereby cloning gene(s) responsible for the trait. See Lander et al., Proc. Natl. Acad. Sci. (USA) 83, 7353–7357 (1986); Lander et al., Proc. Natl. Acad. Sci. (USA) 84, 2363–2367 (1987); Donis-Keller et al., Cell 51, 319–337 (1987); Lander et al., Genetics 121, 185–199 (1989)). Genes localized by linkage can be cloned by a process known as directional cloning. See Wainwright, Med. J. Australia 159, 170–174 (1993); Collins, Nature Genetics 1, 3–6 (1992).

Linkage studies are typically performed on members of a family. Available members of the family are characterized for the presence or absence of a phenotypic trait and for a set of polymorphic markers. The distribution of polymorphic markers in an informative meiosis is then analyzed to determine which polymorphic markers co-segregate with a phenotypic trait. See, e.g., Kerem et al., Science 245, 1073–1080 (1989); Monaco et al., Nature 316, 842 (1985); Yamoka et al., Neurology 40, 222–226 (1990); Rossiter et al., FASEB Journal 5, 21–27 (1991).

Linkage is analyzed by calculation of LOD (log of the odds) values. A lod value is the relative likelihood of obtaining observed segregation data for a marker and a genetic locus when the two are located at a recombination fraction θ, versus the situation in which the two are not linked, and thus segregating independently (Thompson & Thompson, Genetics in Medicine (5th ed, W.B. Saunders Company, Philadelphia, 1991); Strachan, "Mapping the human genome" in The Human Genome (BIOS Scientific Publishers Ltd, Oxford), Chapter 4). A series of likelihood ratios are calculated at various recombination fractions (.theta.), ranging from θ=0.0 (coincident loci) to θ=0.50 (unlinked). Thus, the likelihood at a given value of θ is: probability of data if loci linked at θ to probability of data if loci unlinked. The computed likelihoods are usually expressed as the $\log_{10}$ of this ratio (i.e., a lod score). For example, a lod score of 3 indicates 1000:1 odds against an apparent observed linkage being a coincidence. The use of logarithms allows data collected from different families to be combined by simple addition. Computer programs are available for the calculation of lod scores for differing values of θ (e.g., LIPED, MLINK (Lathrop, Proc. Nat. Acad. Sci. (USA) 81, 3443–3446 (1984)). For any particular lod score, a recombination fraction may be determined from mathematical tables. See Smith et al., Mathematical tables for research workers in human genetics (Churchill, London, 1961); Smith, Ann. Hum. Genet. 32, 127–150 (1968). The value of θ at which the lod score is the highest is considered to be the best estimate of the recombination fraction.

Positive lod score values suggest that the two loci are linked, whereas negative values suggest that linkage is less likely (at that value of θ) than the possibility that the two loci are unlinked. By convention, a combined lod score of +3 or greater (equivalent to greater than 1000:1 odds in favor of linkage) is considered definitive evidence that two loci are linked. Similarly, by convention, a negative lod score of −2 or less is taken as definitive evidence against linkage of the two loci being compared. Negative linkage data are useful in excluding a chromosome or a segment thereof from consideration. The search focuses on the remaining non-excluded chromosomal locations.

5.5. Production of Mutant PHOX2B Gene Product

In various embodiments of the invention, sequences encoding wild-type or mutant PHOX2B gene product are inserted into an expression vector for propagation and expression in recombinant cells. In a specific embodiment, a mutant PHOX2B gene product comprises the amino acid sequence of SEQ ID NO:6, which is encoded by a nucleic acid molecule comprising the nucleic acid sequence of SEQ ID NO:5. The mutant PHOX2B gene product differs from the wild-type PHOX2B protein comprising the amino acid sequence of SEQ ID NO:2 in that the mutant PHOX2B protein comprises a deletion of five alanine residues at amino acid position 245–249 of SEQ ID NO:2.

In a specific embodiment, a lentiviral vector can be used to express PHOX2B or modified gene product (Case et al., 1999, Proc. Natl. Acad. Sci. 96: 2988–2993; Miyoshi et al., 1998, J. Virology 72: 8150–8157).

An expression construct, as used herein, refers to a nucleotide sequence encoding a PHOX2B gene operably associated with one or more regulatory regions which enables expression of the PHOX2B gene in an appropriate host cell. "Operably-associated" refers to an association in which the regulatory regions and the PHOX2B sequence to be expressed are joined and positioned in such a way as to permit transcription, and ultimately, translation.

Such expression construct can also be used to produce antisense PHOX2B RNA, provided that the nucleotide sequence encoding PHOX2B is inserted in the reverse orientation.

The regulatory regions necessary for transcription of the PHOX2B can be provided by the expression vector. A translation initiation codon (ATG) may also be provided if the PHOX2B gene sequence lacking its cognate initiation codon is to be expressed. In a compatible host-expression construct system, cellular transcriptional factors, such as RNA polymerase, will bind to the regulatory regions on the expression construct to effect transcription of the PHOX2B sequence in the host cell. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5'-non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

Both constitutive and inducible regulatory regions may be used for expression of the PHOX2B gene. It may be desirable to use inducible promoters to control the high level expression of the PHOX2B gene once the expression construct is introduced into patient's cells in vivo. Examples of useful regulatory regions are provided below.

In order to attach DNA sequences with regulatory functions, such as promoters, to the PHOX2B gene sequence or to insert the PHOX2B gene sequence into the cloning site of a vector, linkers or adapters providing the appropriate compatible restriction sites may be ligated to the ends of the cDNAs by techniques well known in the art (Wu et al., 1987, Methods in Enzymol 152:343–349). Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA by use of PCR with primers containing the desired restriction enzyme site.

An expression construct comprising a PHOX2B sequence operably associated with regulatory regions can be directly introduced into appropriate host cells for expression and production of PHOX2B protein without further cloning. See, for example, U.S. Pat. No. 5,580,859. The expression constructs can also contain DNA sequences that facilitate integration of the PHOX2B sequence into the genome of the host cell, e.g., via homologous recombination. In this instance, it is not necessary to employ an expression vector comprising a replication origin suitable for appropriate host cells in order to propagate and express the PHOX2B in the host cells.

5.6. Host-Vector Systems

Described herein are systems of vectors and host cells that can be used for the expression of PHOX2B. A variety of expression vectors may be used in the present invention which include, but are not limited to, plasmids, cosmids, phage, phagemids, or modified viruses. Typically, such expression vectors comprise a functional origin of replication for propagation of the vector in an appropriate host cell, one or more restriction endonuclease sites for insertion of the PHOX2B gene sequence, and one or more selection markers. The expression vector must be used with a compatible host cell which may be derived from a prokaryotic or an eukaryotic organism including but not limited to bacteria, yeasts, insects, mammals, and humans.

In one aspect, expression constructs and vectors are introduced into host cells for the purpose of producing the PHOX2B. Any cell type that can produce mammalian proteins and is compatible with the expression vector may be used, including those that have been cultured in vitro or genetically engineered. Host cells may be obtained from normal or affected subjects, including healthy humans, private laboratory deposits, public culture collections such as the American Type Culture Collection, or from commercial suppliers.

Different host cells have characteristic and specific mechanisms for the post-translational processing and modification of proteins. A host cell may be chosen which modifies and processes the expressed gene products in a specific fashion similar to the way the recipient processes its PHOX2B. For the purpose of producing large amounts of PHOX2B for adminstration to a subject, it is preferable that the type of host cell used in the present invention has been used for expression of heterologous genes, and is reasonably well characterized and developed for large-scale production processes.

Vectors based on E. coli are the most popular and versatile systems for high level expression of foreign proteins (Makrides, 1996, Microbiol Rev, 60:512–538). Non-limiting examples of regulatory regions that can be used for expression in E. coli may include but not limited to lac, trp, lpp, phoA, recA, tac, T3, T7 and $\lambda P_L$ (Makrides, 1996, Microbiol Rev, 60:512–538). Non-limiting examples of prokaryotic expression vectors may include the λgt vector series such as λgt11 (Huynh et al., 1984 in "DNA Cloning Techniques", Vol. I: A Practical Approach (D. Glover, ed.), pp. 49–78, IRL Press, Oxford), and the pET vector series (Studier et al., 1990, Methods Enzymol., 185:60–89). However, a potential drawback of a prokaryotic host-vector system is the inability to perform many of the post-translational processing of mammalian cells. Thus, a eukaryotic host-vector system is preferred, a mammalian host-vector system is more preferred, and a human host-vector system is the most preferred.

For expression of PHOX2B in mammalian host cells, a variety of regulatory regions can be used, for example, the SV40 early and late promoters, the cytomegalovirus (CMV) immediate early promoter, and the Rous sarcoma virus long terminal repeat (RSV-LTR) promoter. Inducible promoters that may be useful in mammalian cells include but are not limited to those associated with the metallothionein gene, mouse mammary tumor virus glucocorticoid responsive long terminal repeats (MMTV-LTR), β-interferon gene, and hsp70 gene (Williams et al., 1989, Cancer Res. 49:2735–42; Taylor et al., 1990, Mol. Cell Biol., 10:165–75).

The following animal regulatory regions, which exhibit tissue specificity and have been utilized in transgenic animals, can also be used in tumor cells of a particular tissue type: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286); gonadotropic releasing hormone gene control region which is active in the hypothalamus (Mason et al., 1986, Science 234:1372–1378); probasin and prostate-specific antigen (PSA) gene control region which is active in the prostate (Brookes et al., 1998, The Prostate 35:18–26).

The efficiency of expression of the PHOX2B in a host cell may be enhanced by the inclusion of appropriate transcription enhancer elements in the expression vector, such as those found in SV40 virus, Hepatitis B virus, cytomegalovirus, immunoglobulin genes, metallothionein, β-actin (see Bittner et al., 1987, Methods in Enzymol. 153:516–544; Gorman, 1990, Curr. Op. in Biotechnol. 1:36–47).

The expression vector may also contain sequences that permit maintenance and replication of the vector in more than one type of host cell, or integration of the vector into the host chromosome. Such sequences may include but are not limited to replication origins, autonomously replicating sequences (ARS), centromere DNA, and telomere DNA. It may also be advantageous to use shuttle vectors which can be replicated and maintained in at least two types of host cells.

In addition, the expression vector may contain selectable or screenable marker genes for initially isolating, identifying or tracking host cells that contain DNA encoding a PHOX2B. For long term, high yield production of PHOX2B-peptide complexes, stable expression in mammalian cells is preferred. A number of selection systems may be used for mammalian cells, including but not limited to the Herpes simplex virus thymidine kinase (Wigler et al., 1977, Cell 11:223), hypoxanthine-guanine phosphoribosyltransferase (Szybalski and Szybalski, 1962, Proc. Natl. Acad. Sci. USA 48:2026), and adenine phosphoribosyltransferase (Lowy et al., 1980, Cell 22:817) genes can be employed in tk$^-$, hgprt$^-$ or aprt$^-$ cells, respectively. Also, antimetabolite resistance can be used as the basis of selection for dihydrofolate reductase (dhfr), which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neomycin phosphotransferase (neo), which confers resistance to the aminoglycoside G-418 (Colberre-Garapin et al., 1981, J. Mol. Biol. 150:1); and hygromycin phosphotransferase (hyg), which confers resistance to hygromycin (Santerre et al., 1984, Gene 30:147). Other selectable markers, such as but not limited to histidinol and Zeocin™ can also be used.

Preferred mammalian host cells include but are not limited to those derived from humans, monkeys and rodents, (see, for example, Kriegler M. in "Gene Transfer and Expression: A Laboratory Manual", New York, Freeman & Co. 1990).

A number of viral-based expression systems may also be utilized with mammalian cells to produce PHOX2B. Vectors using DNA virus backbones have been derived from simian virus 40 (SV40) (Hamer et al., 1979, Cell 17:725), adenovirus (Van Doren et al., 1984, Mol Cell Biol 4:1653), adeno-associated virus (McLaughlin et al., 1988, J Virol 62:1963), and bovine papillomas virus (Zinn et al., 1982, Proc Natl Acad Sci 79:4897). In cases where an adenovirus is used as an expression vector, the donor DNA sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing heterologous products in infected hosts. (See e.g., Logan and Shenk, 1984, Proc. Natl. Acad. Sci. (USA) 81:3655–3659).

Bovine papillomavirus (BPV) can infect many higher vertebrates, including man, and its DNA replicates as an episome. A number of shuttle vectors have been developed for recombinant gene expression which exist as stable, multicopy (20–300 copies/cell) extrachromosomal elements in mammalian cells. Typically, these vectors contain a segment of BPV DNA (the entire genome or a 69% transforming fragment), a promoter with a broad host range, a polyadenylation signal, splice signals, a selectable marker, and "poisonless" plasmid sequences that allow the vector to be propagated in *E. coli*. Following construction and amplification in bacteria, the expression gene construct are transfected into cultured mammalian cells by, for example, the calcium phosphate coprecipitation technique. For those host cells that do not manifest a transformed phenotype, selection of transformants is achieved by use of a dominant selectable marker, such as histidinol and G418 resistance. For example, a PHOX2B gene sequence can be inserted into BPV vectors, such as pBCMGSNeo and pBCMGHis (Karasuyama et al., Eur. J. Immunol. 18:97–104; Ohe et al., Human Gene Therapy, 6:325–33) which can then be transfected into a diverse range of cell types for expression of the PHOX2B.

Alternatively, the vaccinia 7.5K promoter may be used. (See, e.g., Mackett et al., 1982, Proc. Natl. Acad. Sci. (USA) 79:7415–7419; Mackett et al., 1984, J. Virol. 49:857–864; Panicali et al., 1982, Proc. Natl. Acad. Sci. 79:4927–4931.) In cases where a human host cell is used, vectors based on the Epstein-Barr virus (EBV) origin (OriP) and EBV nuclear antigen 1 (EBNA-1; a trans-acting replication factor) can be used. Such vectors can be used with a broad range of human host cells, e.g., EBO-pCD (Spickofsky et al., 1990, DNA Prot Eng Tech 2:14–18); pDR2 and λDR2 (available from Clontech Laboratories).

PHOX2B may also be made with a retrovirus-based expression system. Retroviruses, such as Moloney murine leukemia virus, can be used since most of the viral gene sequence can be removed and replaced with PHOX2B gene sequence while the missing viral functions can be supplied in trans. In contrast to transfection, retroviruses can efficiently infect and transfer genes to a wide range of cell types including, for example, primary hematopoietic cells. Moreover, the host range for infection by a retroviral vector can be manipulated by the choice of envelope used for vector packaging.

For example, a retroviral vector can comprise a 5' long terminal repeat (LTR), a 3' LTR, a packaging signal, a bacterial origin of replication, and a selectable marker. The PHOX2B DNA is inserted into a position between the 5' LTR and 3' LTR, such that transcription from the 5' LTR promoter transcribes the cloned DNA. The 5' LTR comprises a promoter, including but not limited to an LTR promoter, an R region, a U5 region and a primer binding site, in that order. Nucleotide sequences of these LTR elements are well known in the art. A heterologous promoter as well as multiple drug selection markers may also be included in the expression vector to facilitate selection of infected cells. See, McLauchlin et al., 1990, Prog Nucleic Acid Res and Molec Biol 38:91–135; Morgenstern et al., 1990, Nucleic Acid Res 18:3587–3596; Choulika et al., 1996, J Virol 70:1792–1798; Boesen et al., 1994, Biotherapy 6:291–302; Salmons and Gunzberg, 1993, Human Gene Therapy 4:129–141; and Grossman and Wilson, 1993, Curr. Opin. in Genetics and Devel. 3:110–114.

Other useful eukaryotic host-vector system may include yeast and insect systems. In yeast, a number of vectors containing constitutive or inducible promoters may be used with *Saccharomyces cerevisiae* (baker's yeast), *Schizosaccharomyces pombe* (fission yeast), *Pichia pastoris*, and *Hansenula polymorpha* (methylotropic yeasts). For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast *Saccharomyces*, 1982, Eds. Strathern et al., Cold Spring Harbor Press, Vols. I and II.

In an insect system, Autographa californica nuclear polyhidrosis virus (AcNPV) a baculovirus, can be used as a vector to express PHOX2B in Spodoptera frugiperda cells. The PHOX2B gene sequences may be cloned into non-essential regions (for example the polyhedrin gene) of the virus and placed under control of an AcNPV promoter (for example the polyhedrin promoter). These recombinant viruses are then used to infect host cells in which the inserted DNA is expressed. (See e.g., Smith et al., 1983, J Virol 46:584; Smith, U.S. Pat. No. 4,215,051.)

Any of the cloning and expression vectors described herein may be synthesized and assembled from known DNA sequences by well known techniques in the art. The regulatory regions and enhancer elements can be of a variety of origins, both natural and synthetic. Some vectors and host cells may be obtained commercially. Non-limiting examples of useful vectors are described in Appendix 5 of Current Protocols in Molecular Biology, 1988, ed. Ausubel et al., Greene Publish. Assoc. & Wiley Interscience, which is incorporated herein by reference; and the catalogs of commercial suppliers such as Clontech Laboratories, Stratagene Inc., and Invitrogen, Inc.

The resulting recombinant PHOX2B can be delivered to the cells in a patient by various methods known in the art.

5.7. Expression of PHOX2B

Expression constructs containing cloned nucleotide sequence encoding PHOX2B can be introduced into the host cell by a variety of techniques known in the art, including but not limited to, for prokaryotic cells, bacterial transformation (Hanahan, 1985, in DNA Cloning, A Practical Approach, 1:109–136), and for eukaryotic cells, calcium phosphate mediated transfection (Wigler et al., 1977, Cell 11:223–232), liposome-mediated transfection (Schaefer-Ridder et al., 1982, Science 215:166–168), electroporation (Wolff et al., 1987, Proc Natl Acad Sci 84:3344), and microinjection (Cappechi, 1980, Cell 22:479–488).

For long term, high yield production of properly processed PHOX2B, expression in mammalian cells is preferred. Cell lines that stably express PHOX2B may be engineered by using a vector that contains a selectable marker. By way of example but not limitation, following the introduction of the expression constructs, engineered cells may be allowed to grow for 1–2 days in an enriched media, and then are switched to a selective media. The selectable marker in the expression construct confers resistance to the selection and optimally allows cells to stably integrate the expression construct into their chromosomes and to grow in culture and to be expanded into cell lines. Such cells can be cultured for a long period of time while PHOX2B is expressed continuously.

The recombinant cells may be cultured under standard conditions of temperature, incubation time, optical density, and media composition.

In an embodiment where the expression construct comprising sequences encoding a PHOX2B is used in gene therapy, the PHOX2B gene sequence is introduced into cancer cells in vivo. Such introduction can be carried out by any method known in the art, such as but not limited to transfection, transduction, microinjection, infection with a viral or bacteriophage vector containing the PHOX2B gene sequences, liposome-mediated gene transfer, microcell-mediated gene transfer, etc. Numerous techniques are known in the art for the introduction of foreign genes into cells (see e.g., Loeffler and Behr, 1993, Meth. Enzymol. 217:599–618; Cohen et al., 1993, Meth. Enzymol. 217:618–644; Cline, 1985, Pharmac. Ther. 29:69–92) may be used in accordance with the present invention, provided that the physiological functions of the recipient are not disrupted. The technique should provide for the stable transfer of the PHOX2B gene sequence to the cell, so that the sequence is expressible by the cell and preferably heritable and expressible by its cell progeny.

In another embodiment, the expression characteristics of an endogenous gene (e.g., PHOX2B gene) within a cell, cell line or microorganism may be modified by inserting a DNA regulatory element heterologous to the endogenous gene of interest into the genome of a cell, stable cell line or cloned microorganism such that the inserted regulatory element is operatively linked with the endogenous gene and controls, modulates or activates. For example, endogenous genes which are normally "transcriptionally silent", i.e., a PHOX2B gene which is normally not expressed, or are expressed only at very low levels in a cell line or microorganism, may be activated by inserting a regulatory element which is capable of promoting the expression of a normally expressed gene product in that cell line or microorganism. Alternatively, transcriptionally silent, endogenous PHOX2B gene may be activated by insertion of a promiscuous regulatory element that works across cell types.

A heterologous regulatory element may be inserted into a stable cell line or cloned microorganism, such that it is operatively linked with and activates expression of endogenous PHOX2B gene, using techniques, such as targeted homologous recombination, which are well known to those of skill in the art, and described e.g., in Chappel, U.S. Pat. No. 5,272,071; PCT publication No. WO 91/06667, published May 16, 1991; Skoultchi U.S. Pat. No. 5,981,214; Treco et al U.S. Pat. No. 5,968,502 and PCT publication No. WO 94/12650, published Jun. 9, 1994. Alternatively, non-targeted e.g., non-homologous recombination techniques which are well-known to those of skill in the art and described, e.g., in PCT publication No. WO 99/15650, published Apr. 1, 1999, may be used.

5.8. Antibodies to PHOX2B Gene

In another embodiment, the present invention relates to the uses of antibodies or fragments thereof capable of specifically recognizing one or more epitopes of the PHOX2B gene, mutant PHOX2B gene, PHOX2B gene products, mutant PHOX2B gene products, epitopes of conserved variants of the PHOX2B gene products, epitopes of mutant PHOX2B gene products, or peptide fragments of the PHOX2B gene products. In addition, antibodies are useful in a variety of ways in accordance with the present invention. These antibodies can be utilized for the diagnosis of HSCR and in certain applications, targeting of affected tissues. Such antibodies may include, but are not limited to, polyclonal antibodies, monoclonal antibodies (mAbs), humanized or chimeric antibodies, single chain antibodies, Fab fragments, F(ab')₂ fragments, Fv fragments, fragments produced by a Fab expression library, anti-idiotypic (anti-Id) antibodies, and epitope-binding fragments of any of the above.

Such antibodies may be used, for example, in the detection of a PHOX2B gene product in an biological sample and may, therefore, be utilized as part of a diagnostic or prognostic technique whereby patients may be tested for abnormal levels of PHOX2B gene products, and/or for the presence of abnormal forms of the such gene products. Such antibodies may also be included as a reagent in a kit for use in a diagnostic or prognostic technique. Such antibodies may also be utilized in conjunction with, for example, compound screening schemes, as described, below, for the evaluation of the effect of test compounds on PHOX2B gene product levels and/or activity. Antibodies to PHOX2B gene product may be used in a method for the inhibition of abnormal PHOX2B gene product activity. Thus, such antibodies may, therefore, be utilized as part of treatment methods for HSCR. Additionally, such antibodies can be used in conjunction with the gene therapy techniques described, below, to, for example, evaluate the normal and/or engineered PHOX2B-expressing cells prior to their introduction into the patient.

Described herein are methods for the production of antibodies of such antibodies or fragments thereof. Any of such antibodies or fragments thereof may be produced by standard immunological methods or by recombinant expression of nucleic acid molecules encoding the antibody or fragments thereof in an appropriate host organism.

Potentially immunogenic domains of the PHOX2B protein or mutant PHOX2B protein are predicted from hydropathy and surface probability profiles. Then oligopeptides which span the predicted immunogenic sites are chemically synthesized. These oligopeptides can be designed to contain the specific mutant amino acids to allow the detection of and discrimination between the mutant versus wild-type gene products. In specific embodiment, mutant PHOX2B protein comprising the amino acid sequence of SEQ ID NO:6 may be used to raise antibodies for the particular portion of the protein that comprises the deletion of five alanine residues.

For the production of antibodies against a PHOX2B gene product, various host animals may be immunized by injection with a PHOX2B gene product, or a fragment thereof. Fragments of PHOX2B can be synthesized as antigenic peptides in accordance with the known amino acid sequence of PHOX2B. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as a PHOX2B gene product, or an antigenic functional derivative thereof. For the production of polyclonal antibodies, host animals such as those described above, may be immunized by injection with PHOX2B gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against PHOX2B gene products. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., 1988, Science 242:1038–1041).

Antibody fragments which recognize specific epitopes may be generated by known techniques. For example, such fragments include but are not limited to: the F(ab')₂ fragments which can be produced by pepsin digestion of the antibody molecule and the Fab fragments which can be generated by reducing the disulfide bridges of the F(ab')₂ fragments. Alternatively, Fab expression libraries may be constructed (H use et al., 1989, Science, 246:1275–1281) to allow rapid and easy identification of monoclonal Fab fragments with the desired specificity.

5.9. Methods of Treatment, Prophylaxis, Management or Amelioration of Symptoms Associated with HSCR The invention provides a method of diagnosis and therapy comprising diagnosing patients at increased risk of HSCR and treating, prophylactic, management, or ameliorating HSCR in an individual having such increased risk by methods of the invention. Management refers to the beneficial effects that a subject derives from a prophylactic or therapeutic agent, which does not result in a cure of the disease. In certain embodiments, a subject is administered one or more prophylactic or therapeutic agents to "manage" a disorder so as to prevent the progression or worsening of the disorder. Known therapies for HSCR can be effective in halting advancement of the disease, or at least slowing the advancement. It is thus an advantage of the invention for early identification of patients at increased risk of HSCR so that preventive therapy can be started as soon as possible, optimizing any intervention potential for affecting outcome. The decision of a physician on how and whether to initiate therapy in anticipation of the disease can be taken with increased confidence. Diseases or disorders that are related to decreased level or activity of PHOX2B may be treated by administering a therapeutic of the invention that intend to replace or act in place of the functionally deficient endogenous PHOX2B gene. An increased level or activity of PHOX2B may be treated by administering a therapeutic of the invention that inhibit the level or activity of endogenous PHOX2B. A variety of suitable treatments of patients at increased risk of HSCR are described in the art. These treatments include, but are not limited to, surgical removal of aganglionic bowel, anastomosis of ano-rectum with ganglionic bowel, colostomy, gene therapy, regeneration of enteric nerves by administration of growth factors, and intestinal or neural cell transplant. Other treatments will be known to persons of skill in the art.

5.10. Therapeutics of the Invention

The invention provides for treatment, prophylaxis, management or amelioration of one or more symptoms associated with the disease, disorder, or infection by administration of therapeutic compound (termed herein "therapeutics") of the invention. Compounds such as those identified through assays described infra, in Section 5.11, which modulate PHOX2B activity can be used in accordance with the invention to treat HSCR. Such molecules can include, but are not limited to peptides, including soluble peptides, and small organic or inorganic molecules, and can be referred to as PHOX2B agonists or antagonists. Dominant negative mutants of PHOX2B and PHOX2B-repressor fusion proteins are also compounds that interfere with the interaction of PHOX2B with intracellular macromolecules may also be used. Techniques for the determination of effective doses and administration of such compounds are described, in Sections 5.13 and 5.14.

Any technique which serves to selectively administer nucleic acid molecules to a cell population of interest can be used, for example, by using a delivery complex. Such a delivery complex can comprise an appropriate nucleic acid molecule and a targeting means. Such targeting means can comprise, for example, sterols, lipids, viruses or target cell specific binding agents. Viral vectors that can be used with recombiant viruses include, but are not limited to adenovirus, adeno-associated virus, herpes simplex virus, vaccinia virus, and retrovirus vectors, in addition to other particles that introduce DNA into cells, such as liposomes.

The therapeutics can be utilized for the prevention of a variety of disorder or diseases related to neuron development, in particular, HSCR, e.g., in individuals who are predisposed as a result of familial history or in individuals with an enhanced risk due to environmental factors.

Described below are methods and compositions for treating HSCR using the PHOX2B gene or gene product as a therapeutic target. The outcome of a treatment is to at least produce in a treated subject a healthful benefit.

All such methods comprise methods which modulate PHOX2b gene activity and/or expression which in turn modulate the phenotype of the treated subject.

The invention also encompasses methods to increase the transcriptional activity of PHOX2B gene, and methods to increase the expression of genes that are under the transcriptional control of PHOX2B proteins. The invention also encompasses methods to increase the translation of PHOX2B transcripts and increasing the stability of the PHOX2B protein. Furthermore, the invention encompasses decreasing the expression of genes that are negatively regulated by PHOX2B. The increase of the transcriptional activity of the PHOX2B gene may provide a novel therapeutic approach for HSCR and other disease conditions that are associated with reduced transcriptional activity of the PHOX2B protein, or underexpression of the protein.

PHOX2B are responsible for various processes related to neural development, including but not limited to, promoting neuron growth and development, development of autonomic crest derivatives, formation, migration and differentiation of neural crest cells into autonomic neurons, coordination of quantitative and qualitative aspects of neurogenesis, generating neurons of the correct phenotype and in proper numbers at the appropriate times and locations, promoting cell cycle exit, cell migration, and initiates cell differentiation. Hence, PHOX2b gene product may be used as therapeutics for the treatment, prophylaxis, management, or amelioration of symptoms associated with any disorders or diseases that are related to PHOX2b aberrations. In a specific embodiment, the therapeutics of the present invention may be used to treat HSCR. Accordingly, the present invention provides therapeutic compositions comprising the nucleotide sequences of PHOX2B nucleic acid molecules as described in Sections 5.1 and 5.5. In specific embodiments, the PHOX2B nucleic acid molecules comprise the open reading frame depicted in FIG. 1 (SEQ ID NO:1), or nucleotide sequences encoding a PHOX2B protein. The invention provides therapeutic compositions comprising purified nucleic acids consisting of at least 10 contiguous nucleotides (i.e., a hybridizable portion) of a PHOX2B sequence; in other embodiments, the nucleic acids consist of at least 15 (continuous) nucleotides, 25 nucleotides, 50 nucleotides, 100 nucleotides, 150 nucleotides, 200 nucleotides, or 250 nucleotides of a PHOX2B sequence. In another embodiment, the nucleic acids are smaller than 35, 200 or 250 nucleotides in length. Nucleic acids can be single or double stranded. The invention also provides therapeutic compositions comprising nucleic acids hybridizable to or complementary to the foregoing sequences. In specific aspects, the nucleic acids comprise a sequence complementary to at least 10, 25, 50, 100, 200, or 250 nucleotides of a PHOX2B gene. In a specific embodiment, a nucleic acid which is hybridizable to a PHOX2B nucleic acid (e.g., having sequence SEQ ID NO:1, 3, 4, or 5), or to a nucleic acid encoding a PHOX2B derivative, under conditions of moderate stringency is provided.

Therapeutic compositions comprising nucleic acids encoding derivatives and analogs of PHOX2B proteins, and PHOX2B antisense nucleic acids are additionally provided. As is readily apparent, as used herein, a "nucleic acid encoding a fragment or portion of a PHXO2B protein" shall be construed as referring to a nucleic acid encoding only the recited fragment or portion of the PHOX2B protein and not the other contiguous portions of the PHOX2B protein as a continuous sequence.

Therapeutic compositions comprising fragments of PHOX2B nucleic acids comprising regions conserved between other PHOX2B nucleic acids, of the same or different species, are also provided. Therapeutic compositions comprising nucleic acids encoding one or more domains of PHOX2B are provided.

Successful treatment of HSCR may be brought about by techniques which serve to decrease PHOX2B activity. Activity can be decreased by, for example, directly decreasing PHOX2B gene product activity and/or by decreasing the level of PHOX2B gene expression.

For example, compounds such as those identified through assays described, above, which decrease PHOX2B activity can be used in accordance with the invention to treat HSCR.

Further, antisense and ribozyme molecules which inhibit PHOX2B gene expression can also be used in accordance with the invention to reduce the level of PHOX2B gene expression, thus effectively reducing the level of PHOX2B gene product present, thereby decreasing the level of PHOX2B activity. Still further, triple helix molecules can be utilized in reducing the level of PHOX2B gene activity. Such molecules can be designed to reduce or inhibit either wild type, or if appropriate, mutant target gene activity. Techniques for the production and use of such molecules are well known to those of skill in the art.

5.10.1. Antisense Molecules

The use of antisense molecules as inhibitors of gene expression is a specific, genetically based therapeutic approach (for a review, see Stein, in Ch. 69, Section 5 "Cancer: Principle and Practice of Oncology", 4th ed., ed. by DeVita et al., J. B. Lippincott, Philadelphia 1993). The present invention provides the therapeutic or prophylactic use of nucleic acids of at least six nucleotides that are antisense to a gene or cDNA encoding PHOX2B or a portion thereof. An "antisense" PHOX2B nucleic acid as used herein refers to a nucleic acid capable of hybridizing to a portion of a PHOX2B RNA (preferably mRNA) by virtue of some sequence complementarity. The invention further provides pharmaceutical compositions comprising an effective amount of the PHOX2B antisense nucleic acids of the invention in a pharmaceutically acceptable carrier, as described infra.

In another embodiment, the invention is directed to methods for inhibiting the expression of a PHOX2B nucleic acid sequence in a mammalian cell in vitro or in vivo comprising providing the cell with an effective amount of a composition comprising an PHOX2B antisense nucleic acid of the invention.

The antisense nucleic acid of the invention may be complementary to a coding and/or noncoding region of a PHOX2B mRNA. The antisense molecules will bind to the complementary PHOX2B gene mRNA transcripts and reduce or prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Nucleic acid molecules that are complementary to the 5' end of the message, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. See generally, Wagner, R., 1994, Nature 372:333–335. Thus, oligonucleotides complementary to either the 5'- or 3'-non-translated, non-coding regions of the PHOX2B gene, as shown, for example, in FIG. 1, could be used in an antisense approach to inhibit translation of endogenous PHOX2B gene mRNA.

Nucleic acid molecules complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of target or pathway gene mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the PHOX2B coding region could be used, those complementary to the transcribed untranslated region are most preferred.

The antisense molecules should be delivered to cells which express the PHOX2B gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous PHOX2B gene transcripts and thereby prevent translation of the PHOX2B gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art, and described in Section 5.6. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3 ' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc. Any type of plasmid, cosmid, YAC or viral vector can be used to prepare the recombinant DNA construct which can be introduced directly into the tissue site. Alternatively, viral vectors can be used which selectively infect the desired tissue.

5.10.2. Ribozyme Molecules

Ribozymes are enzymatic RNA molecules capable of catalyzing the specific cleavage of RNA (For a review see, for example Rossi, J., 1994, Current Biology 4:469–471). The mechanism of ribozyme action involves sequence specific hybridization of the ribozyme molecule to complementary target RNA, followed by a endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding target gene proteins.

Ribozyme molecules designed to catalytically cleave PHOX2B gene mRNA transcripts can also be used to prevent translation of PHOX2B gene mRNA and expression of target or pathway gene. (See, eg., PCT International Publication WO90/11364, published Oct. 4, 1990; Sarver et al., 1990, Science 247:1222–1225). While ribozymes that cleave mRNA at site specific recognition sequences can be used to destroy PHOX2B gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. Preferably the ribozyme is engineered so that the cleavage recognition site is located near the 5' end of the PHOX2B gene mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in an PHOX2B gene.

As in the antisense approach, the ribozymes can be composed of modified oligonucleotides (e.g. for improved stability, targeting, etc.) and should be delivered to cells which express the PHOX2B gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous PHOX2B gene messages and inhibit translation. Because ribozymes unlike antisense molecules, are catalytic, a lower intracellular concentration is required for efficiency.

Anti-sense RNA and DNA, ribozyme, and triple helix molecules of the invention can be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules can be introduced as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

5.10.3. Therapeutic Antibodies

Antibodies exhibiting capability to downregulate PHOX2B gene product activity can be utilized to treat HSCR. Such antibodies can be generated using standard techniques described in Section 5.8, above, against full length wild type or mutant PHOX2B proteins, or against peptides corresponding to portions of the proteins. The antibodies include but are not limited to polyclonal, monoclonal, Fab fragments, single chain antibodies, chimeric antibodies, and the like.

Because PHOX2B is an intracellular protein, it is preferred that internalizing antibodies be used. However, lipofectin or liposomes can be used to deliver the antibody or a fragment of the Fab region which binds to the PHOX2B gene product epitope into cells. Where fragments of the antibody are used, the smallest inhibitory fragment which binds to the PHOX2B protein's binding domain is preferred. For example, peptides having an amino acid sequence corresponding to the domain of the variable region of the antibody that binds to the PHOX2B protein can be used. Such peptides can be synthesized chemically or produced via recombinant DNA technology using methods well known in the art (e.g., see Creighton, 1983; and Sambrook et al., 1989). Alternatively, single chain antibodies, such as neutralizing antibodies, which bind to intracellular epitopes can also be administered. Such single chain antibodies can be administered, for example, by expressing nucleotide sequences encoding single-chain antibodies within the target cell population by utilizing, for example, techniques such as those described in Marasco et al. (Marasco, W. et al., 1993, Proc. Natl. Acad. Sci. USA 90:7889–7893).

5.11. Screening Assays for Compounds that Modulate PHOX2B Activity

The present invention provides a drug target, PHOX2B gene, for the treatment, prophylaxis, amelioration, and management of HSCR. Hence, a therapeutics of the invention may be a compound that modulates the PHOX2B gene. Such compound may bind or interact with the PHOX2B gene or gene product. Accordingly, provided herein are screening assays for compounds that may, through its interaction with the PHOX2B gene or PHOX2B gene product, affect the onset, or progression of HSCR.

The following assays are designed to identify: (i) compounds that bind to PHOX2B gene products, including mammalian and non-mammalian homologs of PHOX2B; (ii) compounds that bind to other intracellular proteins and/or segments of nucleic acid that interact with a PHOX2B gene product, including mammalian and non-mammalian homologs of PHOX2B; (iii) compounds that interfere with the interaction of the PHOX2B gene product, including mammalian and non-mammalian homologs of PHOX2B, with other intracellular proteins and/or segments of nucleic acid; and (iv) compounds that modulate the activity of PHOX2B gene (i.e., modulate the level of PHOX2B gene expression and/or modulate the level of PHOX2B gene product activity).

Assays may additionally be utilized which identify compounds which bind to PHOX2B gene regulatory sequences (e.g., promoter sequences). See e.g., Platt, 1994, J. Biol. Chem. 269:28558–28562, which is incorporated herein by reference in its entirety. Also provided is a method for identifying compounds that modulate PHOX2B gene expression, comprising: (a) contacting a test compound with a cell or cell lysate containing a reporter gene operatively associated with a PHOX2B gene regulatory element; and (b) detecting expression of the reporter gene product. Also provided is another method for identifying compounds that modulate PHOX2B gene expression comprising: (a) contacting a test compound with a cell or cell lysate containing PHOX2B transcripts; and (b) detecting the translation of the PHOX2B transcript. Any reporter gene known in the art can be used, such as but limited to, green fluorescent protein, β-galactosidase, alkaline phosphatase, chloramphenicol acetyltransferase, etc.

5.11.1. In Vitro Screening Assays for Compounds that Bind to the PHOX2B Gene Product In vitro systems may be designed to identify compounds capable of interacting with, e.g., binding to, the PHOX2B gene products of the invention and homologs of PHOX2B. Compounds identified may be useful, for example, in modulating the activity of wild type and/or mutant PHOX2B gene products, may be useful in elaborating the biological function of the PHOX2B gene product, may be utilized in screens for identifying compounds that disrupt normal PHOX2B gene product interactions, or may in themselves disrupt such interactions.

The principle of the assays used to identify compounds that interact with the PHOX2B gene product involves preparing a reaction mixture of the PHOX2B gene product, or fragments thereof and the test compound under conditions and for a time sufficient to allow the two components to interact with, e.g., bind to, thus forming a complex, which can represent a transient complex, which can be removed and/or detected in the reaction mixture. These assays can be conducted in a variety of ways. For example, one method to conduct such an assay would involve anchoring PHOX2B gene product or the test substance onto a solid phase and detecting PHOX2B gene product/test compound complexes anchored on the solid phase at the end of the reaction. In one embodiment of such a method, the PHOX2B gene product or fragment thereof may be anchored onto a solid surface, and the test compound, which is not anchored, may be labeled, either directly or indirectly.

In practice, microtitre plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for PHOX2B gene product or the test compound to anchor any complexes formed in solution, and a labeled antibody specific for the other component of the possible complex to detect anchored complexes.

5.11.2. Assays for Intracellular Proteins that Interact with the PHOX2B Gene Product Any method suitable for detecting protein-protein interactions or protein-nucleic acid interactions may be employed for identifying PHOX2B protein-intracellular protein interactions, especially interactions mediated by the PHOX2B domain.

Among the traditional methods which may be employed are co-immunoprecipitation, crosslinking and co-purification through gradients or chromatographic columns. Surface display library and yeast-based two-hybrid system can also be utilized to isolate the gene encoding such PHOX2B-binding proteins.

These methods allow the identification of molecules, including intracellular proteins, that interact with PHOX2B gene products. Once isolated, such a protein can be sequenced using techniques well-known to those of skill in the art, such as by Edman degradation (see, e.g., Creighton, 1983, "Proteins: Structures and Molecular Principles," W. H. Freeman & Co., N.Y., pp.34–49). The amino acid sequence obtained may be used as a guide for the generation of oligonucleotide mixtures that can be used to screen for gene sequences encoding such proteins. Screening may be accomplished, for example, by standard hybridization or PCR techniques. Techniques for the generation of oligonucleotide mixtures and the screening are well-known. (See, e.g., Ausubel, supra, and 1990, "PCR Protocols: A Guide to Methods and Applications," Innis, et al., eds. Academic Press, Inc., New York).

Another method that detects protein interactions in vivo is the two-hybrid system, which is described here for illustration only and not by way of limitation. One example of this approach has been described (Chien, et al., 1991, Proc. Natl. Acad. Sci. USA, 88:9578–9582) and a kit is commercially available from Clontech (Palo Alto, Calif.).

The two-hybrid system or related methodologies may be used to screen activation domain libraries for proteins that interact with a "bait" gene product. By way of example, and not by way of limitation, PHOX2B gene products may be used as the bait gene product. Total genomic or cDNA sequences are fused to the DNA encoding an activation domain. This library and a plasmid encoding a hybrid of a bait PHOX2B gene product fused to the DNA-binding domain are co-transformed into a yeast reporter strain, and the resulting transformants are screened for those that express the reporter gene. For example, a bait PHOX2B gene sequence, such as the open reading frame of the PHOX2B gene, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait PHOX2B gene product are to be detected can be made using methods routinely practiced in the art. According to the particular system described herein, for example, the cDNA fragments can be inserted into a vector such that they are translationally fused to the transcriptional activation domain of GAL4. Such a library can be co-transformed along with the bait PHOX2B gene-GAL4 fusion plasmid into a yeast strain that contains a lacZ gene driven by a promoter that contains GAL4 activation sequence. A cDNA encoded protein, fused to a GAL4 transcriptional activation domain that interacts with bait PHOX2B gene product will reconstitute an active GAL4 protein and thereby drive expression of the HIS3 gene. Colonies that express HIS3 can be detected by their growth on petri dishes containing semi-solid agar based media lacking histidine. The cDNA can then be purified from these strains, and used to produce and isolate the bait PHOX2B gene product-interacting protein using techniques routinely practiced in the art.

Additionally, methods may be employed which result in the identification of nucleic acids which interact with the PHOX2B protein, i.e., PHOX2B target sites. These methods include, for example, probing gene libraries with labeled PHOX2B protein or fragments thereof (e.g., PHOX2B domain), using PHOX2B protein or fragments thereof in a manner similar to the well-known technique of antibody probing of λgt11 libraries. Such methods can also be adapted to monitor the interactions of dominant negative mutants of PHOX2B and PHOX2B target sites. Furthermore, novel PHOX2B target sequences can be isolated by the RNA differential display technique and whole genome PCR. See Robinson et al., 1997, Proc. Natl. Acad. Sci. USA, 94:7170–7175.

5.11.3. Assays for Compounds that Interfere with PHOX2B Gene Product/Intracellular Marcromolecular Interaction The PHOX2B gene products of the invention, fragments thereof, and homologs of PHOX2B may, in vivo, interact with one or more intracellular macromolecules, such as proteins and nucleic acid molecules. Such macromolecules may include, but are not limited to DNA, RNA (including polyadenylated (poly(A)) RNA and RNA with the 5' cap structure) and those proteins identified via methods such as those described, above, in Section 5.8.2. For purposes of this discussion, such intracellular macromolecules are referred to herein as "interacting partners". Compounds that disrupt PHOX2B interactions in this way may be useful in regulating the activity of the PHOX2B gene product, including mutant PHOX2B gene products. Such compounds may include, but are not limited to molecules such as peptides, and the like, which would be capable of gaining access to the intracellular PHOX2B gene product.

The basic principle of the assay systems used to identify compounds that interfere with the interaction between the PHOX2B gene product and its intracellular interacting partner or partners involves preparing a reaction mixture containing the PHOX2B gene product, or fragments thereof, and the interacting partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of PHOX2B gene product and its intracellular interacting partner. Control reaction mixtures are incubated without the test compound or with a vehicle or carrier. The formation of any complexes between the PHOX2B gene product or fragments thereof and the intracellular interacting partner is then detected. The formation of a complex in the control reaction, but not in the reaction mixture containing the test compound, indicates that the compound interferes with the interaction of the PHOX2B gene protein and the interacting partner. Additionally, complex formation within reaction mixtures containing the test compound and normal PHOX2B gene protein may also be compared to complex formation within reaction mixtures containing the test compound and a mutant PHOX2B gene protein. This comparison may be important in those cases wherein it is desirable to identify compounds that disrupt interactions of mutant but not normal PHOX2B gene proteins.

5.11.4. Cell-Based Assays for Identification of Compounds that Modulate PHOX2B Cell-based methods are presented herein which identify compounds capable of treating HSCR by modulating PHOX2B activity. Specifically, such assays identify compounds which affect PHOX2B-dependent processes, such as but not limited to promoting neuron growth and development, development of autonomic crest derivatives, formation, migration and differentiation of neural crest cells into autonomic neurons, coordination of quantitative and qualitative aspects of neurogenesis, generating neurons of the correct phenotype and in proper numbers at the appropriate times and locations, promoting cell cycle exit, cell migration, and initiates cell differentiation.

In another embodiment, the cell-based assays are based on expression of the PHOX2B gene product in a mammalian cell and measuring the PHOX2B-dependent process. Any mammalian cells that can express the PHOX2B gene and allow the functioning of the PHOX2B gene product can be used. Recombinant expression of the PHOX2B gene in these cells can be achieved by methods described above. In these assays, cells producing functional PHOX2B gene products are exposed to a test compound for an interval sufficient for the compound to modulate the activity of the PHOX2B gene product. The activity of PHOX2B gene product can be measured directly or indirectly through the detection or measurement of PHOX2B-dependent cellular processes such as, for example, the manifestation of a transformed phenotype. As a control, a cell not producing the PHOX2B gene product may be used for comparisons. Depending on the cellular process, any techniques known in the art may be applied to detect or measure it.

5.12. Gene Therapy

Gene therapy refers to treatment or prevention of a disease performed by the administration of a nucleic acid to a subject. In this embodiment of the invention, the therapeutic nucleic acid produces intracellularly a nucleic acid molecule of the invention that mediates a therapeutic effect by modulating PHOX2B expression. In an embodiment, nucleic acids comprising a sequence encoding a wild-type PHOX2B gene are administered to treat symptoms related to HSCR.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5): 155–215). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds.), 1994, Current Protocols in Human Genetics, John Wiley & Sons, N.Y.

Delivery of the nucleic acid into a patient may be either direct, in which case the patient is directly exposed to the nucleic acid or nucleic acid-carrying vector or a delivery complex, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the nucleic acid molecule of the invention or encoded functional PHOX2B gene product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in biopolymers (e.g., poly-$\beta$-1->→4-N-acetylglucosamine polysaccharide; see U.S. Pat. No. 5,635, 493), encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:4429–4432), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342: 435–438).

In a specific embodiment, a viral vector that contains the PHOX2B nucleic acid molecule of the invention is used. For example, a retroviral vector can be used (see Miller et al., 1993, Meth. Enzymol. 217:581–599). These retroviral vectors have been modified to delete retroviral sequences that are not necessary for packaging of the viral genome and integration into host cell DNA. The nucleic acid molecule of the invention to be used in gene therapy is cloned into the vector, which facilitates delivery of the gene into a patient.

The form and amount of therapeutic nucleic acid envisioned for use depends on the symptoms presented by the HSCR patient, desired effect, patient state, etc., and can be determined by one skilled in the art.

5.13. Pharmaceutical Preparations and Methods of Administration

The compounds and nucleic acid sequences described herein can be administered to a patient at therapeutically effective doses to treat or prevent cancer. A therapeutically effective dose refers to that amount of a compound sufficient to result in a healthful benefit in the treated subject. Formulations and methods of administration that can be employed when the therapeutic composition comprises a nucleic acid are described below.

Pharmaceutical compositions for use in accordance with the present invention can be formulated in conventional manner using one or more physiologically acceptable carriers or excipients.

Thus, the compounds and their physiologically acceptable salts and solvents can be formulated for administration by inhalation or insufflation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the compound and a suitable powder base such as lactose or starch.

The compounds can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

5.14. Characterization and Demonstration of Therapeutic or Prophylactic Utility Toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The therapeutics used in accordance with the present invention also can be determined by using various experimental animal models.

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which a patient tissue sample is grown in culture, and exposed to or otherwise administered a protocol, and the effect of such protocol upon the tissue sample is observed. A lower level of proliferation or survival of the contacted cells indicates that the Therapeutic is effective to treat the condition in the patient. Alternatively, instead of culturing cells from a patient, Protocols may be screened using cells of a tumor or malignant cell line. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc.

Compounds for use in therapy can be tested in suitable animal model systems prior to testing in humans, including but not limited to in rats, mice, chicken, cows, monkeys, rabbits, etc.

Further, any assays known to those skilled in the art can be used to evaluate the prophylactic and/or therapeutic utility of the therapies disclosed herein for treatment or prevention of HSCR.

Efficacy in treating HSCR may be demonstrated by detecting the ability of the Therapeutics of the present invention, or a composition of the invention to reduce or inhibit HSCR in an animal or to ameliorate or alleviate one or more symptoms associated with HSCR. The treatment is considered therapeutic if there is, for example, a reduction is in or amelioration of one or more symptoms following administration of the therapeutics, or a composition of the invention.

5.15. Animal Models

The generation of a mouse or other animal model of HSCR is important for both an understanding the biology of the disease but also for testing of potential therapies. Currently, there is no animal model available for the common nonsyndromic HSCR.

The present invention provides an animal model of HSCR by introduction of a mutant PHOX2B gene such as, but not limited to the mutant PHOX2B gene comprising the nucleic acid sequence of SEQ ID NO:3, in a number of species including mice, rats, pigs, and primates. Methods for specifically mutating genes by homologous recombination in embryonic stem cells (ES cells) have been described (Capecci 1989, Science 244:1288). A wild-type PHOX2B gene may be replaced by a mutated PHOX2B gene. Methods for transgenic procedures are well known in the art. Murphy and Carter, 1992, Curr. Opin.Cell. Biol.4:273–279.

6. EXAMPLES

The following examples are provided to illustrate certain aspects of the present invention and not intended as limiting the subject matter thereof:

6.1. Collection of Blood Samples from HSCR Patients

A total of 91 ethnic Chinese patients, diagnosed with HSCR between 1984 and 2001, were included in this study. Diagnosis was made at Queen Mary Hospital, Hong Kong SAR, and was based on histological examination of either biopsy or surgical resection material for absence of enteric plexuses. Eighty-six patients were affected with sporadic HSCR (4 individuals with total aganglionosis, 4 individuals with long-segment aganglionosis and 78 individuals with short-segment aganglionosis) and five patients (with short-segment aganglionosis) also had affected relatives (2 unrelated families in total). Within the sporadic group, 8 patients (1 with total aganglionosis and 7 with short-segment aganglionosis) presented with associated anomalies (5 with Down's syndrome; 1 with Waardenburg syndrome; 1 with renal agenesis and 1 with parathyroid adenoma). Normal controls (39 individuals) were unselected, unrelated, ethnic Chinese subjects from Hong Kong without a diagnosis of HSCR. DNA was extracted from peripheral blood as previously described (Sancandi et al. 2000). All patients and controls assented to molecular analysis. The study was approved by the local ethical committee.

6.2. Amplification and Sequencing the PHOX2B Gene

Polymerase chain reaction (PCR) was used to amplify the three coding regions (including 5' and 3' flanking regions) of PHOX2B. For exons 1 and 2, PCR was performed in a 25 µl reaction volume containing 100 ng genomic DNA; a mixture of all four nucleotides (final concentration 0.2 mM for each nucleotide); 2.5 µl of 10× reaction buffer; 0.5 µM of each appropriate primer; 1 mM of MgCl2, and 1.25 U of AmpliTaq Gold polymerase (Applied Biosystems, Foster City, Calif.). Due to its high GC content, amplification of exon 3 was performed using the GC-RICH PCR System (Roche Molecular Biochemicals, USA). Exon 3 PCR was performed in 25 µl reaction volume containing 100 ng genomic DNA; a mixture of all four nucleotides (final concentration 0.2 mM for each nucleotide); 5 µl of 5× GC-RICH PCR reaction buffer; 2.5 µl of 5 M GC-RICH resolution solution; 0.5 µM of each appropriate primer, and 1.25 U of a blend of Taq DNA Polymerase and Tgo DNA Polymerase.

Primers used to amplify the three coding regions, including intron-exon boundaries, were derived from the PHOX2B gene sequence available in GenBank (accession number AB015671). The primers were as follow (size of amplified DNA is in parenthesis; forward primer is first shown in each set): exon 1: GACCTCAGACAAGGCATCTCA (SEQ ID No. 7) and AATTACCCCTCCCTGCAATC (SEQ ID No. 8) (586 bp); exon 2: CTGCCGTATGACCTGACCTT (SEQ ID No. 9) and ACAGCCACACCAAATCCAGT (SEQ ID No. 10) (442 bp); exon 3: ACCCTAACCGGTGCTTTTCT (SEQ ID No. 11) and ACAATAGCCTTGGGCCTACC (SEQ ID No. 12) (687 bp). The cycling conditions for the three exons were 95° C. for 8 min followed by 35 cycles of 95 ° C. for 1 min, 62° C. for 1 min and 72° C. for 45 s. A final 10 min extension was included at the end of the 35 cycles. Prior to sequencing, PCR products were column purified (Life Technologies, UK) to remove reaction buffer and unincorporated primers and visualized by running 5 µl of each sample on 2% agarose gels. PCR products were screened for mutations by direct sequencing using a dye terminator cycle sequencing kit (ABI PRISM® Big Dye™ Terminator v 2.0 Cycle sequencing kit, Applied Biosystems, Foster City, Calif.) and an ABI 3100 automated sequencer (Applied Biosystems, Foster City, Calif.). For those samples in which DNA sequence variation had been observed, PCR amplification from genomic DNA and sequencing using both forward and reverse primers, were repeated up to five times.

The first polymorphism identified was an A to G transition at position 2250 of the SEQ ID No 1 in intron 2, 100 bp away from the intron/exon boundary. The second polymorphism identified was an A to C change at position 3508 of the SEQ ID No 1, in codon 255 of the PHOX2B exon 3. A to C2607 is a silent transition that does not alter the amino acid sequence. The third sequence variant was a 15 bp deletion at position 3511 of the SEQ ID No 1, in exon 3, starting from codon 256 and just 3 bp downstream of the A to C change at position 3508. This 15 bp deletion occurs in one of the two poly-alanine stretches in the C-terminus, resulting in the loss of five alanine residues (codons 256–260).

6.3. Association of the Newly-Discovered Alleles with HSCR

Allele and genotype frequencies for each polymorphism in the control group and the unrelated patients were calculated. Allele and genotype frequency comparisons between the control group and the patient group were performed using $X^2$ (chi-square) tests. Chi-square tests were also performed to determine whether each polymorphism was in Hardy-Weinberg equilibrium within each group.

The level of association between genotypes involving two or three polymorphic sites and HSCR was assessed using both chi-square contingency tables and the EH program (Terwilliger and Ott, 1994). Haplotype frequencies for each polymorphism (with and without allelic association) were estimated by the EH program. To test whether haplotype frequencies were significantly different between cases and controls, we performed three separate analysis using the EH program: on the case subjects alone, on the control subjects alone, and on the combination of case subjects and controls. The three log-likelihoods obtained (lnLcase, lnLcontrol, and lnLcombined) were used to calculate the relevant statistic test $2[ln(Lcase)+ln(Lcontrol)-ln(Lcombined)]$ which gives an approximate $X^2$ distribution under the hypothesis that allelic association is allowed. The EH program, which assumes Hardy-Weinberg equilibrium, was also used to estimate LD between polymorphisms.

TABLE 1

Genotype frequency distribution of the PHOX2B gene polymorphisms

| Polymorphisms | Total patients (91) | Total controls (39) |
|---|---|---|
| $A/G_{2250}$ | | |
| AA | 0.81 (73) | 0.62 (24) |
| AG | 0.16 (15) | 0.38 (15) |
| GG | 0.03 (3) | 0.00 (0) |
| | $X^2 = 8.28; p = 0.015$ | |
| $A/C_{3508}$ | | |
| AA | 0.90 (82) | 0.85 (33) |
| AC | 0.10 (9) | 0.15 (6) |
| CC | 0.00 (0) | 0.00 (0) |
| | $X^2 = 0.72; p = 0.39$ | |
| $DEL_{3511}$ | | |
| NN[a] | 0.92 (84) | 0.82 (32) |
| ND[b] | 0.08 (7) | 0.18 (7) |
| DD | 0.00 (0) | 0.00 (0) |
| | $X^2 = 2.99; p = 0.08$ | |

Number of individuals in brackets. [a]N no deletion; [b]D deletion;

Comparison of the genotype frequencies of the three new polymorphisms between patient and control groups (Table 1) revealed statistically significant differences for A to G2550 ($X^2=8.28$; p=0.015). For this particular polymorphism, genotypes comprising G were under-represented in the patient group (19% in patients versus 38% in controls). Within each group, no statistically significant differences in genotype frequencies for any of the identified polymorphisms were found between genders. Within each group, each of the three polymorphic sites was in Hardy-Weinberg equilibrium.

6.4. Identification of Additional Polymorphisms in PHOX2B Associated with HSCR The procedures for evaluating the candidate gene PHOX2B, as well as for finding additional polymorphisms, will be the same as for those already identified. Mutation detection in the coding sequence of these genes will consist of PCR amplification and sequencing. Mutation detection for the entire genes will include large deletion/insertion analysis of 200–400 bp fragments by SSCP or heteroduplex analysis, and of course sequencing when heterozygosity becomes apparent for any region of the genes. Current Protocols in Human Genetics (John Wiley & Sons, Inc.), Chapter 7, "Searching Candidate Genes for Mutations." Biological samples already isolated from patients with HSCR which did not show any abnormalities in PHOX2B will be screened for polymorphisms mother HSCR genes. Although preferred embodiments have been depicted and described in detail herein, it will be apparent to those skilled in the relevant art that various modifications, additions, substitutions, and the like can be made without departing from the spirit of the invention and these therefore are considered within the scope of the invention.

7. RESULTS

7.1. Polymorphic Sites

By direct sequencing the entire coding region and portions of 5' and 3' flanking regions, two new SNPs and one deletion in the PHOX2B gene (FIG. 8) were identified. Nucleotide positions are defined in relation to the first nucleotide of the start codon, which is designated position +1.

The first polymorphism identified was an A→G transition (referred as AG 2250) in intron 2,100 bp away from the intron/exon boundary. The second polymorphism identified was an A→C change (referred as AC 3508) of the PHOX2B exon 3. AC 3508 is a silent transition that does not alter the amino acid sequence (GCA GCC). The third sequence variant was a 15 bp deletion (referred as DEL 3511) in exon 3, just two base pair downstream of the AC 3508 polymorphism (FIG. 8). This 15 bp deletion occurs in one of the two poly-alanine stretches in the C-terminus, resulting in the loss of five alanine residues. The poly-alanine region in the normal PHOX2B protein may form α-helical structures and serve as a flexible linker (Shoemaker et al. 1987). Among the 39 normal individuals studied, 7 individuals had this deletion in one of their PHOX2B alleles. Specific PCR amplification enzymes were used to the resolve the high GC sequence content of exon 3. In addition, those samples with the deletion were re-amplified and re-sequenced 5 to 10 times.

Finally, in every sample analyzed there was an A at both positions 1129 and 2304 of the PHOX2B gene (intron 2 and 3 respectively; FIG. 8). The Genbank accession numbers for PHOX2B (AB015671 and AFI 17979) record T and G respectively. These may represent sequencing errors in the GenBank entries. Alternatively, the Chinese population analyzed in this study has these SNPs.

In addition to the three polymorphisms described in this study, there are three other PHOX2B SNPs recorded in GenBank. Polymorphism ss3136952 (also rs2196822) is a A→C 3004 transition at position 3004 of the PHOX2B gene (intron 2); polymorphism ss1551093 (also rs1063611) is a T→A 5343 transversion at position 5343 (end of 3' untranslated region) and polymorphisms ss1551094 (also rs1063612) is a C→A5403 transversion at position 5403 (end of 3' untranslated region).

7.2. Allelic Variation Between Patients and Controls

To determine the significance of these three novel polymorphisms in HSCR, a case-control association study was conducted to investigate whether they were directly related to the HSCR phenotype. Differences in allele frequencies between the patient group and the control group were not statistically significant for any of the polymorphisms (AC 3508 $X^2=0.76$; p=0.38; DEL3511 $X^2=2.82$; p=0.09). Also within each group, allele frequencies of each gender were compared. No statistically significant differences for any of the identified polymorphisms were found.

7.3. Haplotype Frequencies and Linkage Disequilibrium Among the Three Polymorphic Sites The level of association between HSCR and the genotypes involving two or three polymorphic sites was also assessed. When comparing frequencies of haplotypes generated by the combination AG2250+AC3508 and by the combination AG2250+DEL3511 statistically significant differences between patients and controls were found for both haplotype combinations ($X^2=8.45$; p=0.03 and $X^2=10.13$; p=0.03 respectively). Contributions to $X^2$ were dissected and demonstrated that the major contribution was that of genotypes of the polymorphic site AG2250. In contrast, no statistically significant difference in frequencies was found for the combination AC 3508+DEL3511. When haplotypes comprising the three polymorphisms were analyzed for differences in frequencies, a statistical trend toward association ($X^2=9.47$; p 0.05, 4 df) was found mainly due to the major contribution of the AG 2250 polymorphism. Using the EH program, the haplotype frequencies of the three polymorphisms in 91 patients and 39 controls were estimated (Table 2).

TABLE 2

Estimated haplotype frequencies in the 91 patients and 39 control determined by EH

| Haplotypes | | | Frequencies | | |
|---|---|---|---|---|---|
| Intro 2 | Exon 3 | | | | |
| AG 2250 | AC 3508 | DEL 3511 | Patients | Controls | All subjects |
| A | A | ND | 0.855 | 0.795 | 0.828 |
| A | A | D | 0.029 | 0.028 | 0.029 |
| A | C | ND | 0.000 | 0.014 | 0.004 |
| A | C | D | 0.000 | 0.000 | 0.000 |
| G | A | ND | 0.056 | 0.067 | 0.060 |
| G | A | D | 0.009 | 0.061 | 0.024 |
| G | C | ND | 0.049 | 0.062 | 0.053 |
| G | C | D | 0.000 | 0.000 | 0.000 |

The two most common haplotypes for both cases and controls were A-A-ND and G-A-ND (allele designations as shown in Table 1). When haplotype frequencies were compared, none of the haplotype combinations showed statistically significant differences in frequencies between patients and controls (Table 3). Hence, the associations found were driven by the presence of AG 2250.

TABLE 3

Association testing based on the haplotype frequencies of AG 2250, AC 3508 and DEL 3511

| Group | $N^a$ | ln(L) | $X^2$ | $p^b$ |
|---|---|---|---|---|
| Patients | 91 | −90.84 | 36.54 | 0.3 |
| Controls | 39 | −55.89 | 15.19 | |
| All subjects | 130 | −150.92 | 49.24 | |

$^a$Number of individuals; $^b$Calculated from 2[ln(Lcase) + ln(Lcontrol) − ln(Lcombined)]; df = 7

Significant evidence for LD was found among the three polymorphisms for both patients and controls, either analyzed independently or combined LD between two polymorphisms were also assesed (Table 4).

TABLE 4

Pairwise linkage disequilibrium

| Pairwise comparison | Patients | | Controls | | All subjects | |
|---|---|---|---|---|---|---|
| | $X^2$ | P | $X^2$ | p | $X^2$ | p |
| AG 2250 vs. AC 3508 | 34.67 | 0.00 | 6.36 | 0.50 | 38.68 | 0.00 |
| AG 2250 vs. DEL 3511 | 0.12 | 0.90 | 4.08 | 0.25 | 2.13 | 0.50 |
| AC 3508 vs. DEL 3511 | 0.72 | 0.86 | 1.18 | 0.75 | 1.29 | 0.70 |

The AG 2250 polymorphism was in LD with AC 3508 when cases and controls were analyzed combined and in the patient population. AG 2250 was not in LD with AC 3508 in the control group. No LD was found between AG 2250+ DEL 3511, nor between AC 3508+DEL 3511, despite being two base pairs apart only. The AG 2250 polymorphism is directly associated with HSCR and that the discrepancies in the analysis of haplotype frequencies are due to incomplete LD.

8. DISCUSSION

SNPs are used as markers in human genetics studies ranging from comparative population variation (Chakravarti 1999) to disease linkage studies (Kruglyak 1997). SNPs also have potential as direct functional polymorphic variants involved in common and genetically complex human diseases (Collins et al. 1997) and pharmacogenetic traits (Housman and Ledley 1998). In addition, SNPs can also serve as surrogates for unrecognized functional SNPs that may be identified by disease-marker LD studies (Chakravarti 1999; Collins et al. 1997).

The entire coding region of the PHOX2B gene was sequenced as well as intron/exon boundaries of ethnically matched patients and controls in the search for mutations or polymorphisms that could contribute to the clinical manifestation of HSCR. Two new SNPs (AG 2250, AC 3508) and one deletion (DEL 3511) have been identified. The DEL 3511 showed no association with HSCR despite causing the loss of 5 alanine-residues in the PHOX2B protein. In both patients and controls, the DEL 3511 was always heterozygous. In mice, heterozygous disruption of PHOX2B homeodomain shows no obvious phenotype, but homozygous mutants are embryonic lethal. In those individuals carrying DEL 3511, any functional consequence caused by the DEL 3511 polymorphism may be compensated by the normal allele.

For AG 2250 statistically significant difference in genotype distribution was found when patients were compared to controls indicating an association of AG 2250 polymorphism with HSCR. This under-representation may indicate that the transition AG 2250 is relatively recent in evolutionary terms, as shown by the relatively low frequency of the allele G in the population. If the minor allele G conferred a protective effect, its frequency in the population would be rising to become the major allele (Cargill 1999).

The association found may be due to a direct contribution of AG 2250 to the HSCR phenotype or being in LD with another susceptibility locus. Direct involvement of AG 2250 in HSCR may be through the alteration of intronic sequences crucial for splicing and/or regulation of the expression of PHOX2B gene. Genotypes comprising allele G were under represented in the patient group (19% vs 38%; $X^2$=8.28; p=0.015) and in males (19% vs. 44%; $X^2$=8.71; p=0.012) compared with male controls. The association of PHOX2B AG 2250 polymorphism with HSCR may represent a protective effect against HSCR phenotype in male or provide a linkage marker for other HSCR susceptibility gene loci.

There were LD among the three polymorphisms that spread over 1.2 Kb, which was expected given their physical proximity. Pairwise disequilibrium test showed lack of LD between AC 3508 and DEL 3511 polymorphisms which are only two base pairs apart. This indicates that these two polymorphisms are probably situated in a recombination hot spot. Detailed sequence examination of exon 3 (from nucleotide 3176 to 3691) in which these polymorphisms are located showed that there is a high GC content and CGG repeats which may serve as foci for recombination. Recombination across the hot spot would explain the results obtained in the pairwise disequilibrium test and haplotype analysis. This suggests that if there are other polymorphisms or mutations in and around the PHOX2B gene which are also contributing to HSCR, they should be located upstream of the AG 2250 polymorphism. These other possible susceptibility loci may not be in LD with the polymorphisms (AC 3508 and DEL 3511) found in the recombination hot spot that defines the breakpoint of a LD block (Goldstein 2001).

In humans both the RET and EDNRB signaling pathways are crucial in the development of enteric neurons and have been associated to HSCR. Nevertheless, mutations in RET account for less than 50% of the HSCR patients challenging the understanding of the disease etiology. It is likely that a combination of specific variations in multiple genes of both the RET and EDNRB signaling pathways confer either protection or susceptibility to the disease. Co-existence of RET mutations with mutations or polymorphisms in GDNF and EDNRB genes have been described in patients with HSCR (Hofstra et al. 1997; Salomon et al. 1996). Therefore, there may be a role for PHOX2B in HSCR, acting in combination with mutations in RET or other genes such as EDNRB, EDN3, and GDNF genes.

All references (including books, articles, papers, patents, and patent applications) cited herein are hereby expressly incorporated by reference in their entirety for all purposes. While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

What is claimed is:

1. A method for screening a human subject predisposed or susceptible to Hirschsprung's disease (HSCR) associated with a genetic polymorphism in the PHOX2B gene, said method comprising:
   (a) providing a biological sample from the subject; and
   (b) testing the sample for the presence of an adenine at nucleotide position 2250 of SEQ ID NO:1, wherein the presence of the adenine in both copies of the subject's PHOX2B gene at this position indicates that the subject is genetically predisposed to HSCR.

2. A method for diagnosing a human subject with increased risk of HSCR associated with a genetic polymorphism in the PHOX2B gene, said method comprising:
   (a) providing a biological sample from the subject; and
   (b) testing the sample for the presence of an adenine in both copies of the subject's PHOX2B gene at nucleotide position 2250 of SEQ ID NO:1, wherein the presence of the adenine at this position indicates that the subject is genetically predisposed to Hirschsprung's disease (HSCR).

3. The method of claim 1 or 2, wherein step (b) comprises amplifying a fragment of the PHOX2B gene comprising two or more nucleotides including a nucleotide at position 2250.

4. The method of claim 3, wherein the fragment is amplified using PCR primers comprising nucleotide sequence of SEQ ID NOS:9 and 10.

5. The method of claim 1 or 2, wherein the biological sample is selected from the group consisting of blood, saliva, amniotic fluid, and urine.

* * * * *

SEQUENCE LISTING

<160> NUMBER OF SEQ ID NOS: 6

<210> SEQ ID NO 1
<211> LENGTH: 5508
<212> TYPE: DNA
<213> ORGANISM: Homo sapiens

<400> SEQUENCE: 1
cctgagtctc ttgaaagcac atttagctgc aagaagaaat gcaatttata agatgctttc    60

```
tctctgtctc tctttgtttt taaccccctc taaccaggtg tattttaaa gaaatccgct      120
tatcgttcac ataaacccc ttggcccact tactctatgt tacagggcgc ctgagtcttg       180
ccaatgtccc agtcctttat aacatttcat gcacttcggg gggtaggctt gttgttaaat     240
tgagcgtgta acactcttac aaaacaggtt ttctatgaca tcaaggtttc ttctccctaa     300
ccgaggggga aaaaagaag aggacgaaga aggggaaaa cacacacact atctcaattt       360
atgcctaagg tatatgatca gttaaaaagg cttaaaagct cggggaaatt ggatcaggga     420
gaatcgtcac ccaactttca ttatttccaa gtagtgtgat tgaattaaag ggcagggagc     480
tggttagaag ggaggatcag gggctcggtg cgtaatggtg tggtattaaa ttctaattag     540
agatgcagga atcaatgata gggaggttgg acagctcagt tccccagtgc cagcccaata     600
gacggatgag ttattgtcat gtaaaaagcg ccagcaataa gaccaaccgc tttgctattg     660
tccaagtgga aagagccaag tttattatga ggactatatg ctctagagac ctcagacaag     720
gcatctcata ggaggctttt tcataaaact aggctctgct ggtagtaagg aggccagttt     780
ggaggcaggc gttgagctgt gcacatctcc ccactccagc caccttctcc atatccatct     840
tttatttcat ttttccactt ggctgagcca tccagaacct tttcaatgta taaaatggaa     900
tattcttacc tcaattcctc tgcctacgag tcctgtatgg ctgggatgga cacctcgagc    960
ctggcttcag cctatgctga cttcagttcc tgcagccagg ccagtggctt ccagtataac   1020
ccgataagga ccacttttgg ggccacgtcc ggctgcccctt ccctcacgcc gggatcctgc   1080
agcctgggca ccctcaggga ccaccagagc agtccgtacg ccgcaggtta ggaccttcag   1140
cttttctcagc ggaggaagcc gccttccgc ccgtatatag gaagccttga ttgcatttga   1200
aaatggaaat gtgtttagta tttaccaaac gaaatttgct tacacaaatg aaagaattta   1260
tcacgtttga agcgattgca gggaggggta attcacttac agggttacac tatcctagtc    1320
acacccgaac cgcccacaaa attatcttaa gctgccaaaa tgataggcat aatttattta   1380
ctttgcgatg agacgtatag cttagaaaat aattgaatta caaagagtaa agctcattac   1440
tggcagtgtc tctttttta agaaccgaga gcggctcaca cttcttgggc tggtcatttt   1500
tatgattatt tctttaattt attattattt ttttgcagct cttt ccccca acttttgagc   1560
cgggtcaact ttctgagaat tgaaaagttc ccaaagtggg actgtttggt aacttctttc   1620
cctggctccc ctgatattcc gactgatgtt ttgggatttt tttcctctct ggttttttcc   1680
tgctgaaagc actatctcaa gtccgtcaca tcgcgctgtt tcaatccacc caaaggcgct   1740
tgtgccagaa aggactccgc caagcccgaa gtttgagccc aggtttccgc agataacaaa   1800
tttcctcggt ttcttcccgc agcttctctc ggcaactctc tcgcgcgggt gtaggtagcg   1860
gctgccgtat gacctgacct tggagtcctc acattctagc tccacggccg gcgagctgcc   1920
ggctgatttg ctcactttct gtctcctctg tcatactcta gttccttaca aactcttcac   1980
ggaccacggc ggcctcaacg agaagcgcaa gcagcggcgc atccgcacca ctttcaccag   2040
tgcccagctc aaagagctgg aaagggtctt cgcggagact cactacccg acatctacac   2100
tcgggaggag ctggccctga agatcgacct cacagaggcg cgagtccagg tacgcgcgcc   2160
tggaaaccga ccccgctccg ccgcactggt ccggggaggt gtgggtgag gggcggctgg   2220
tgaaattcga agtcctggag cctcgagtga aaggaccta gggccccatg ccgatcaga    2280
aatactggat ttggtgtggc tgtgcgttcg agagaggctt agagcgcacg ctcttggcat   2340
tttatttaca gttgcgaagt gtttcccacc cgagcagaga catgggggc cttgggacgt    2400
```

-continued

```
ggatgagcga tgcaatttcg gggacaggaa gtgcctgtgg tggaaggtgt gcagactttg    2460
ctcccgtatt ataagttttt ccttctcccc tcccgccccc caaaaaaatg cctcctaact    2520
caagtgcttt taacctggcc ccatggcata taggttcatt ttcccggaaa ctgtgacttg    2580
cattagattt gcaaagggtc tgtgacttca tgaaggtcaa gaaccatgac ttactccaac    2640
ctgttaaaca caggtgcgct cacgagttgg ccacagcgcc ttttgggtg agccccccgac    2700 cgagaagcgg tgcgcaccat tgcacgcttt tccaggctca aaggccgggg atgggcagcg    2760
gagcaaaccc agagaggatc ccttttcctt ttaccaatta gagtttaact ttagaactta    2820
ggcttagggg tgaatggcga gctcgggggct tgctcaagaa gccgactgaa cagaggccca    2880
ccaaaataag gccttccctt ttcgggtctt tctgggacct gcggcttttt aaactctgcc    2940
gcaagccttc atgtccctgg cgtgctcact ccccctaaga aagtttctcc gaaaatgcac    3000
agcaataaga agcggtagac ttggtggatg tgcgcgcggg ggtgatcaca gcgcatgggg    3060
aggagggtgt taaaacaagc cgaagtagaa cttgggccac cctaaccggt gcttttcttt    3120
cccatttcct tcttctcccc cctgcttcac cgtctctcct tccgtcttgg gccaggtgtg    3180
gttccagaac cgccgcgcca agtttcgcaa gcaggagcgc gcagcggcag ccgcagcggc    3240
cgcggccaag aacggctcct cgggcaaaaa gtctgactct tccagggacg acgagagcaa    3300
agaggccaag agcactgacc cggacagcac tggggcccca ggtcccaatc caaccccac    3360 ccccagctgc ggggcgaatg gaggcggcgg cggcgggccc agcccggctg gagctccggg    3420
ggcggcgggg cccgggggcc cggggaggcga acccggcaag ggcggcgcag cagcagcggc    3480
ggcggccgcg gcagcggcgg cggcggcagc ggcagcggcg gcagctggag gcctggctgc    3540
ggctgggggc cctggacaag gctgggctcc cggccccgc cccatcacct ccatcccgga    3600
ttcgcttggg ggtcccttcg gcagcgtcct atcttcgctc caaagaccca acggtgccaa    3660
agccgcctta gtgaagagca gtatgttctg atctggaatc ctgcggcggc ggcggcggcg    3720
gcgacagcgg gcgagccagg gcccggggcgg gcgagtgggc gagcgggtag gcccaaggct    3780
attgtcgtcg ctgctgccat ggcttttttca ttgagggcct aaagtaatcg cgctaagaat    3840
aaagggaaaa cggcgtcgcc ctcatttcaa ccccactcct accccccttcc tcaaccccca    3900 aacaaaacaa acaaacttcc ctggcttcgc acctgcctgg ggcctcgcag cggggccagg    3960
gctccgcctg ctgatcgggg gttgtgagca gcgcggcctg gacgcggggc actctcaggg    4020
ggctgtgtct gcgtgtcagt ttgtgtctgt ctcggggaat gtgtgtctgt ggcccaagca    4080
ggtgacagga agagatgggg ggcctcaacc aacttagtga cttgtttaga aaaaaaagac    4140
aaaaaagtaa aaataaaaac aaaaaagttg gaaggcagaa accattaaaa aacaaaaagc    4200
caacaaccca gaaaggttta aaaaacataa ggaaaaaaaa gacaaattaa aggagggggct    4260 aggggagaag ctgcagctgg agctgaaggc tcgatcttgt gaaccccctaa atccgctccc    4320 tcctaacagc acggattctc ttggggctct tcttcaggga agagtaggga cgccgttcca    4380
gccccccttc ctatcgtgtc cttgggttcg ggtcactgcg gcgacgactt gctcagactg    4440
tcccggcggc cggagtgact ttctcgcacc cccttgcctg tcccacctcg ctgaacacca    4500
tcccgccatt agcgcatcgg aaccccacac agttgcaact cccaacccgg aatctttgca    4560
gccgttcggc cctgaaagat gccctatcca tgagatgcct tttcatctgc aaactctgca    4620
aaatgtgtct catgtttcgc aactcttttt ttcccctcg ctcccgccta ccccgtcggc    4680
attttcttct tccaccagct tttactgaac tttttggcac tgctttggat tggggtcaat    4740
tgcagtccac gtaactggct gcagagaaat ctaccgagca aggaaaaggc acacacacac    4800
```

```
gtttgcaggg gtgtctcggt ttgcatttct gttggaatga tccgaactgg actcacatcc   4860
tgtatggtgg atggactgta tattgagggt tccattcttc gcgcagttta gacatctctg   4920
ttttgattct ttgttgttgt ttttatttta aaaggcacaa actctagata ttagttgaat   4980
gttgaggctt taacttttc ggtgtctttc tacaactgtg ttctgtgact caattgtatc   5040
gtgttaatat cagtgcagac tgtctcctct acgtgaccgt ataatgtttt tctcgtcttg   5100
tagtctctat ggcgtgtctt tatggtgtaa taaggttctc acggggtcaa tcttttgtgt   5160
ttagagaggc cacggttcag acaatggtat atatttttgt tatcaggtgc atgtctgtct   5220
gatttctttt ttttcctgt tggactatgt ttgtgaacat aattgtcata agttatgttt   5280
cagatttttg aatttattta tatgtgttat aatgaatgct tctatttaaa agggaaatat   5340
ttctacatgt gcttatagtt ttccaagagt gtaccattaa cttgattgtt gataataaaa   5400
accaaaagca agtctagcaa ttgaactctt cttttcttg attctttttt tttttttttt   5460
tttgggttgg tcattgtttt tttttttaa gtttttttt aaaggat               5508
```

<210> SEQ ID NO 2
<211> LENGTH: 314
<212> TYPE: PRT
<213> ORGANISM: Homo sapiens

<400> SEQUENCE: 2

```
Met Tyr Lys Met Glu Tyr Ser Tyr Leu Asn Ser Ser Ala Tyr Glu Ser
 1               5                  10                  15

Cys Met Ala Gly Met Asp Thr Ser Ser Leu Ala Ser Ala Tyr Ala Asp
            20                  25                  30

Phe Ser Ser Cys Ser Gln Ala Ser Gly Phe Gln Tyr Asn Pro Ile Arg
        35                  40                  45

Thr Thr Phe Gly Ala Thr Ser Gly Cys Pro Ser Leu Thr Pro Gly Ser
    50                  55                  60

Cys Ser Leu Gly Thr Leu Arg Asp His Gln Ser Ser Pro Tyr Ala Ala
65                  70                  75                  80

Val Pro Tyr Lys Leu Phe Thr Asp His Gly Gly Leu Asn Glu Lys Arg
                85                  90                  95

Lys Gln Arg Arg Ile Arg Thr Thr Phe Thr Ser Ala Gln Leu Lys Glu
            100                 105                 110

Leu Glu Arg Val Phe Ala Glu Thr His Tyr Pro Asp Ile Tyr Thr Arg
        115                 120                 125

Glu Glu Leu Ala Leu Lys Ile Asp Leu Thr Glu Ala Arg Val Gln Val
    130                 135                 140

Trp Phe Gln Asn Arg Arg Ala Lys Phe Arg Lys Gln Glu Arg Ala Ala
145                 150                 155                 160

Ala Ala Ala Ala Ala Ala Lys Asn Gly Ser Ser Gly Lys Lys Ser
                165                 170                 175

Asp Ser Ser Arg Asp Asp Glu Ser Lys Glu Ala Lys Ser Thr Asp Pro
            180                 185                 190

Asp Ser Thr Gly Gly Pro Gly Asn Pro Asn Pro Thr Pro Ser Cys
        195                 200                 205

Gly Ala Asn Gly Gly Gly Gly Gly Pro Ser Pro Ala Gly Ala Pro
    210                 215                 220

Gly Ala Ala Gly Pro Gly Gly Pro Gly Gly Glu Pro Gly Lys Gly Gly
225                 230                 235                 240

Ala Ala Ala Ala Ala Ala Ala Ala Ala Ala Ala Ala Ala Ala Ala
                245                 250                 255
```

```
Ala Ala Ala Ala Gly Gly Leu Ala Ala Ala Gly Gly Pro Gly Gln Gly
            260                 265                 270

Trp Ala Pro Gly Pro Gly Pro Ile Thr Ser Ile Pro Asp Ser Leu Gly
        275                 280                 285

Gly Pro Phe Gly Ser Val Leu Ser Ser Leu Gln Arg Pro Asn Gly Ala
    290                 295                 300

Lys Ala Ala Leu Val Lys Ser Ser Met Phe
305                 310

<210> SEQ ID NO 3
<211> LENGTH: 5508
<212> TYPE: DNA
<213> ORGANISM: Homo sapiens

<400> SEQUENCE: 3
```

| | | | | | |
|---|---|---|---|---|---|
| cctgagtctc | ttgaaagcac | atttagctgc | aagaagaaat | gcaatttata | agatgctttc | 60 |
| tctctgtctc | tctttgtttt | taacccctc | taaccaggtg | tatttttaaa | gaaatccgct | 120 |
| tatcgttcac | ataaaccccc | ttggcccact | tactctatgt | tacagggcgc | ctgagtcttg | 180 |
| ccaatgtccc | agtcctttat | aacatttcat | gcacttcggg | gggtaggctt | gttgttaaat | 240 |
| tgagcgtgta | acactcttac | aaaacaggtt | ttctatgaca | tcaaggtttc | ttctccctaa | 300 |
| ccgaggggga | aaaaagaag | aggacgaaga | aggggaaaa | cacacacact | atctcaattt | 360 |
| atgcctaagg | tatatgatca | gttaaaaagg | cttaaaagct | cggggaaatt | ggatcaggga | 420 |
| gaatcgtcac | ccaactttca | ttatttccaa | gtagtgtgat | tgaattaaag | ggcagggagc | 480 |
| tggttagaag | ggaggatcag | gggctcggtg | cgtaatggtg | tggtattaaa | ttctaattag | 540 |
| agatgcagga | atcaatgata | gggaggttgg | acagctcagt | tccccagtgc | cagcccaata | 600 |
| gacggatgag | ttattgtcat | gtaaaaagcg | ccagcaataa | gaccaaccgc | tttgctattg | 660 |
| tccaagtgga | aagagccaag | tttattatga | ggactatatg | ctctagagac | ctcagacaag | 720 |
| gcatctcata | ggaggctttt | tcataaaact | aggctctgct | ggtagtaagg | aggccagttt | 780 |
| ggaggcaggc | gttgagctgt | gcacatctcc | ccactccagc | caccttctcc | atatccatct | 840 |
| tttatttcat | ttttccactt | ggctgagcca | tccagaacct | tttcaatgta | taaaatggaa | 900 |
| tattcttacc | tcaattcctc | tgcctacgag | tcctgtatgg | ctgggatgga | cacctcgagc | 960 |
| ctggcttcag | cctatgctga | cttcagttcc | tgcagccagg | ccagtggctt | ccagtataac | 1020 |
| ccgataagga | ccacttttgg | ggccacgtcc | ggctgcccct | ccctcacgcc | gggatcctgc | 1080 |
| agcctgggca | ccctcaggga | ccaccagagc | agtccgtacg | ccgcaggtta | ggaccttcag | 1140 |
| cttttctcagc | ggaggaagcc | gcctttccgc | ccgtatatag | gaagccttga | ttgcatttga | 1200 |
| aaatggaaat | gtgtttagta | tttaccaaac | gaaatttgct | tacacaaatg | aaagaattta | 1260 |
| tcacgtttga | agcgattgca | gggagggta | attcacttac | agggttacac | tatcctagtc | 1320 |
| acacccgaac | cgcccacaaa | attatcttaa | gctgccaaaa | tgataggcat | aatttattta | 1380 |
| ctttgcgatg | agacgtatag | cttagaaaat | aattgaatta | caaagagtaa | agctcattac | 1440 |
| tggcagtgtc | tctttttta | agaaccgaga | gcggctcaca | cttcttgggc | tggtcatttt | 1500 |
| tatgattatt | tctttaattt | attattattt | ttttgcagct | cttttccccca | acttttgagc | 1560 |
| cgggtcaact | ttctgagaat | tgaaaagttc | ccaaagtggg | actgtttggt | aacttctttc | 1620 |
| cctggctccc | ctgatattcc | gactgatgtt | ttgggatttt | ttcctctct | ggttttttcc | 1680 |
| tgctgaaagc | actatctcaa | gtccgtcaca | tcgcgctgtt | tcaatccacc | caaaggcgct | 1740 |

```
tgtgccagaa aggactccgc caagcccgaa gtttgagccc aggtttccgc agataacaaa    1800
tttcctcggt ttcttcccgc agcttctctc ggcaactctc tcgcgcgggt gtaggtagcg    1860
gctgccgtat gacctgacct tggagtcctc acattctagc tccacggccg gcgagctgcc    1920
ggctgatttg ctcactttct gtctcctctg tcatactcta gttccttaca aactcttcac    1980
ggaccacggc ggcctcaacg agaagcgcaa gcagcggcgc atccgcacca ctttcaccag    2040
tgcccagctc aaagagctgg aaagggtctt cgcggagact cactacccg acatctacac     2100 tcgggaggag ctggccctga agatcgacct cacagaggcg cgagtccagg tacgcgcgcc    2160
tggaaaccga ccccgctccg ccgcactggt ccggggaggt gtggggtgag gggcggctgg    2220
tgaaattcga agtcctggag cctcgagtgg aaggaccta gggccccatg ccgatcaga     2280 aatactggat ttggtgtggc tgtgcgttcg agagaggctt agagcgcacg ctcttggcat    2340
tttatttaca gttgcgaagt gtttcccacc cgagcagaga catggggggc cttgggacgt    2400
ggatgagcga tgcaatttcg gggacaggaa gtgcctgtgg tggaaggtgt gcagactttg    2460
ctcccgtatt ataagttttt ccttctcccc tcccgccccc caaaaaaatg cctcctaact    2520
caagtgcttt taacctggcc ccatggcata taggttcatt ttcccggaaa ctgtgacttg    2580
cattagattt gcaaagggtc tgtgacttca tgaaggtcaa gaaccatgac ttactccaac    2640
ctgttaaaca caggtgcgct cacgagttgg ccacagcgcc ttttgggtg agcccccgac    2700 cgagaagcgg tgcgcaccat tgcacgcttt tccaggctca aaggccgggg atgggcagcg    2760
gagcaaaccc agagaggatc cctttccctt ttaccaatta gagtttaact ttagaactta    2820
ggcttagggg tgaatggcga gctcggggct tgctcaagaa gccgactgaa cagaggccca    2880
ccaaaataag gccttccctt ttcggtgtctt tctgggacct gcggcttttt aaactctgcc    2940
gcaagccttc atgtccctgg cgtgctcact cccctaaga aagtttctcc gaaaatgcac    3000
agcaataaga agcggtagac ttggtggatg tgcgcgcggg ggtgatcaca gcgcatgggg    3060
aggagggtgt taaaacaagc cgaagtagaa cttgggccac cctaaccggt gcttttcttt    3120
cccatttcct tctttctccc cctgcttcac cgtctctcct tccgtcttgg gccaggtgtg    3180
gttccagaac cgccgcgcca agtttcgcaa gcaggagcgc gcagcggcag ccgcagcggc    3240
cgcggccaag aacggctcct cgggcaaaaa gtctgactct tccagggacg acgagagcaa    3300
agaggccaag agcactgacc cggacagcac tgggggccca ggtcccaatc ccaaccccac    3360
ccccagctgc ggggcgaatg gaggcggcg cggcggcc agcccggctg gagctccggg       3420
ggcggcgggg cccgggggcc cggaggcga acccggcaag ggcggcgcag cagcagcggc     3480
ggcggccgcg gcagcggcgg cggcggcagc ggcagcggcg gcagctggag gcctggctgc    3540
ggctgggggc cctggacaag gctgggctcc cggccccggc ccatcacct ccatcccgga     3600 ttcgcttggg ggtccttcg gcagcgtcct atcttcgctc caaagaccca acggtgccaa     3660
agccgcctta gtgaagagca gtatgttctg atctggaatc ctgcggcggc ggcggcggcg    3720
gcgacagcgg gcgagccagg gcccgggcgg gcgagtgggc gagcgggtag gcccaaggct    3780
attgtcgtcg ctgctgccat ggcttttca ttgagggcct aaagtaatcg cgctaagaat     3840
aaagggaaaa cggcgtcgcc ctcatttcaa ccccactcct acccccttcc tcaaccccca    3900
aacaaaacaa acaaacttcc ctggcttcgc acctgcctgg ggcctcgcag cggggccagg    3960
gctccgcctg ctgatcgggg gttgtgagca gcgcggcctg gacgcggggc actctcaggg    4020
ggctgtgtct gcgtgtcagt ttgtgtctgt ctcggggaat gtgtgtctgt ggcccaagca    4080
ggtgacagga agagatgggg ggcctcaacc aacttagtga cttgtttaga aaaaaaagac    4140
```

```
aaaaaagtaa aaataaaaac aaaaaagttg gaaggcagaa accattaaaa aacaaaaagc      4200
caacaaccca gaaaggttta aaaaacataa ggaaaaaaaa gacaaattaa aggaggggct      4260
aggggagaag ctgcagctgg agctgaaggc tcgatcttgt gaaccectaa atccgctccc      4320 tcctaacagc acggattctc ttggggctct tcttcaggga agagtaggga cgccgttcca      4380 gcccccttc ctatcgtgtc cttgggttcg ggtcactgcg gcgacgactt gctcagactg       4440
tcccggcggc cggagtgact ttctcgcacc cccttgcctg tcccacctcg ctgaacacca      4500
tcccgccatt agcgcatcgg aaccccacac agttgcaact cccaaccccg aatctttgca      4560
gccgttcggc cctgaaagat gccctatcca tgagatgcct tttcatctgc aaactctgca      4620
aaatgtgtct catgtttcgc aactcttttt ttcccctcg ctcccgccta cccgtcggc        4680 attttcttct tccaccagct tttactgaac tttttggcac tgctttggat tggggtcaat     4740
tgcagtccac gtaactggct gcagagaaat ctaccgagca aggaaaaggc acacacacac      4800
gtttgcaggg gtgtctcggt ttgcatttct gttggaatga tccgaactgg actcacatcc     4860
tgtatggtgg atggactgta tattgagggt tccattcttc gcgcagttta gacatctctg     4920
ttttgattct ttgttgttgt ttttatttta aaggcacaa actctagata ttagttgaat      4980
gttgaggctt taactttttc ggtgtctttc tacaactgtg ttctgtgact caattgtatc     5040
gtgttaatat cagtgcagac tgtctcctct acgtgaccgt ataatgtttt tctcgtcttg     5100
tagtctctat ggcgtgtctt tatggtgtaa taaggttctc acgggtcaa tcttttgtgt      5160 ttagagaggc cacggttcag acaatggtat atattttgt tatcaggtgc atgtctgtct      5220
gatttctttt ttttttcctgt tggactatgt ttgtgaacat aattgtcata agttatgttt    5280 cagattttg aatttattta tatgtgttat aatgaatgct tctatttaaa agggaaatat      5340
ttctacatgt gcttatagtt ttccaagagt gtaccattaa cttgattgtt gataataaaa     5400
accaaaagca agtctagcaa ttgaactctt cttttttcttg attcttttt tttttttttt     5460 tttgggttgg tcattgtttt ttttttttaa gtttttttt aaaaggat                   5508
```

<210> SEQ ID NO 4
<211> LENGTH: 5508
<212> TYPE: DNA
<213> ORGANISM: Homo sapiens

<400> SEQUENCE: 4

```
cctgagtctc ttgaaagcac atttagctgc aagaagaaat gcaatttata agatgctttc       60
tctctgtctc tctttgtttt taaccccctc taaccaggtg tattttaaa gaaatccgct      120 tatcgttcac ataaaccccc ttggcccact tactctatgt tacagggcgc ctgagtcttg     180
ccaatgtccc agtcctttat aacatttcat gcacttcggg gggtaggctt gttgttaaat     240
tgagcgtgta acactcttac aaaacaggtt ttctatgaca tcaaggtttc ttctccctaa     300 ccgagggga aaaaagaag aggacgaaga aggggaaaa cacacacact atctcaattt       360
atgcctaagg tatatgatca gttaaaaagg cttaaaagct cggggaaatt ggatcaggga     420
gaatcgtcac ccaactttca ttatttccaa gtagtgtgat tgaattaaag ggcagggagc     480
tggttagaag ggaggatcag gggctcggtc cgtaatggtg tggtattaaa ttctaattag     540
agatgcagga atcaatgata gggaggttgg acagctcagt tccccagtgc cagcccaata     600
gacggatgag ttattgtcat gtaaaaagcg ccagcaataa gaccaaccgc tttgctattg     660
tccaagtgga aagagccaag tttattatga ggactatatg ctctagagac ctcagacaag     720
```

-continued

| | |
|---|---|
| gcatctcata ggaggctttt tcataaaact aggctctgct ggtagtaagg aggccagttt | 780 |
| ggaggcaggc gttgagctgt gcacatctcc ccactccagc caccttctcc atatccatct | 840 |
| tttatttcat ttttccactt ggctgagcca tccagaacct tttcaatgta taaaatggaa | 900 |
| tattcttacc tcaattcctc tgcctacgag tcctgtatgg ctgggatgga cacctcgagc | 960 |
| ctggcttcag cctatgctga cttcagttcc tgcagccagg ccagtggctt ccagtataac | 1020 |
| ccgataagga ccacttttgg ggccacgtcc ggctgcccct ccctcacgcc gggatcctgc | 1080 |
| agcctgggca ccctcaggga ccaccagagc agtccgtacg ccgcaggtta ggaccttcag | 1140 |
| cttttctcagc ggaggaagcc gccttttccgc ccgtatatag gaagccttga ttgcatttga | 1200 |
| aaatggaaat gtgtttagta tttaccaaac gaaatttgct tacacaaatg aaagaattta | 1260 |
| tcacgtttga agcgattgca gggagggta attcacttac agggttacac tatcctagtc | 1320 |
| acacccgaac cgcccacaaa attatcttaa gctgccaaaa tgataggcat aatttattta | 1380 |
| ctttgcgatg agcgtatag cttagaaaat aattgaatta caaagagtaa agctcattac | 1440 |
| tggcagtgtc tcttttttta agaaccgaga gcggctcaca cttcttgggc tggtcatttt | 1500 |
| tatgattatt tctttaattt attattattt ttttgcagct cttteccca acttttgagc | 1560 |
| cgggtcaact ttctgagaat tgaaaagttc ccaaagtggg actgtttggt aacttctttc | 1620 |
| cctggctccc ctgatattcc gactgatgtt ttgggatttt tttcctctct ggttttttcc | 1680 |
| tgctgaaagc actatctcaa gtccgtcaca tcgcgctgtt tcaatccacc caaaggcgct | 1740 |
| tgtgccagaa aggactccgc caagcccgaa gtttgagccc aggtttccgc agataacaaa | 1800 |
| tttcctcggt ttcttcccgc agcttctctc ggcaactctc tcgcgcgggt gtaggtagcg | 1860 |
| gctgccgtat gacctgacct tggagtcctc acattctagc tccacggccg gcgagctgcc | 1920 |
| ggctgatttg ctcactttct gtctcctctg tcatactcta gttccttaca aactcttcac | 1980 |
| ggaccacggc ggcctcaacg agaagcgcaa gcagcggcgc atccgcacca ctttcaccag | 2040 |
| tgcccagctc aaagagctgg aaagggtctt cgcggagact cactacccccg acatctacac | 2100 |
| tcgggaggag ctggccctga agatcgacct cacagaggcg cgagtccagg tacgcgcgcc | 2160 |
| tggaaaccga ccccgctccg ccgcactggt ccggggaggt gtggggtgag gggcggctgg | 2220 |
| tgaaattcga agtcctggag cctcgagtga aaggaccta gggcccccatg gccgatcaga | 2280 |
| aatactggat ttggtgtggc tgtgcgttcg agagaggctt agagcgcacg ctcttggcat | 2340 |
| tttatttaca gttgcgaagt gtttcccacc cgagcagaga catggggggc cttgggacgt | 2400 |
| ggatgagcga tgcaatttcg gggacaggaa gtgcctgtgg tggaaggtgt gcagactttg | 2460 |
| ctcccgtatt ataagttttt ccttctcccc tcccgcccccc caaaaaaatg cctcctaact | 2520 |
| caagtgcttt taacctggcc ccatggcata taggttcatt ttcccggaaa ctgtgacttg | 2580 |
| cattagattt gcaaagggtc tgtgacttca tgaaggtcaa gaaccatgac ttactccaac | 2640 |
| ctgttaaaca caggtgcgct cacgagttgg ccacagcgcc ttttttgggtg agcccccgac | 2700 |
| cgagaagcgg tgcgcaccat tgcacgcttt tccaggctca aaggccgggg atgggcagcg | 2760 |
| gagcaaaccc agagaggatc cctttttcctt ttaccaatta gagtttaact ttagaactta | 2820 |
| ggcttagggg tgaatggcga gctcgggct tgctcaagaa gccgactgaa cagaggccca | 2880 |
| ccaaaataag gccttccctt ttcgggtctt tctgggacct gcggcttttt aaactctgcc | 2940 |
| gcaagccttc atgtccctgg cgtgctcact cccctaagaa agtttctcc gaaaatgcac | 3000 |
| agcaataaga agcggtagac ttggtggatg tgcgcgcggg ggtgatcaca gcgcatgggg | 3060 |
| aggagggtgt taaaacaagc cgaagtagaa cttgggccac cctaaccggt gcttttctttt | 3120 |

```
cccattttct tctttctccc cctgcttcac cgtctctcct tccgtcttgg gccaggtgtg   3180
gttccagaac cgccgcgcca agtttcgcaa gcaggagcgc gcagcggcag ccgcagcggc   3240
cgcggccaag aacggctcct cgggcaaaaa gtctgactct tccagggacg acgagagcaa   3300
agaggccaag agcactgacc cggacagcac tgggggccca ggtcccaatc ccaaccccac   3360
ccccagctgc ggggcgaatg gaggcggcgg cggcgggccc agcccggctg gagctccggg   3420
ggcggcgggg cccgggggcc cggaggcga acccggcaag ggcggcgcag cagcagcggc   3480
ggcggccgcg gccgcggcgg cggcggcagc ggcagcggcg gcagctggag gcctggctgc   3540
ggctgggggc cctggacaag gctgggctcc cggccccggc cccatcacct ccatcccgga   3600
ttcgcttggg ggtcccttcg gcagcgtcct atcttcgctc caaagaccca acggtgccaa   3660
agccgcctta gtgaagagca gtatgttctg atctggaatc ctgcggcggc ggcggcggcg   3720
gcgacagcgg gcgagccagg gcccggcgg gcgagtgggc gagcgggtag gcccaaggct   3780
attgtcgtcg ctgctgccat ggcttttca ttgagggcct aaagtaatcg cgctaagaat   3840
aaagggaaaa cggcgtcgcc ctcatttcaa ccccactcct accccttcc tcaaccccca   3900 aacaaaacaa acaaacttcc ctggcttcgc acctgcctgg ggcctcgcag cggggccagg   3960
gctccgcctg ctgatcgggg gttgtgagca gcgcggcctg gacgcggggc actctcaggg   4020
ggctgtgtct gcgtgtcagt ttgtgtctgt ctcggggaat gtgtgtctgt ggcccaagca   4080
ggtgacagga agatgggg ggcctcaacc aacttagtga cttgtttaga aaaaaagac   4140 aaaaagtaa aaataaaac aaaaagttg aaggcagaa accattaaaa aacaaaaagc   4200
caacaaccca gaaaggtta aaaaacataa ggaaaaaaa gacaaattaa aggagggct   4260 aggggagaag ctgcagctgg agctgaaggc tcgatcttgt gaaccctaa atccgctccc   4320 tcctaacagc acggattctc ttggggctct tcttcaggga agagtaggga cgccgttcca   4380 gcccccttc ctatcgtgtc cttgggttcg ggtcactgcg gcgacgactt gctcagactg   4440
tcccggcggc cggagtgact ttctcgcacc cccttgcctg tcccacctcg ctgaacacca   4500 tccccgccatt agcgcatcgg aacccccacac agttgcaact cccaacccg aatctttgca   4560 gccgttcggc cctgaaagat gccctatcca tgagatgcct tttcatctgc aaactctgca   4620
aaatgtgtct catgtttcgc aactcttttt tccccctcg ctcccgccta ccccgtcggc   4680
attttcttct tccaccagct tttactgaac ttttttggcac tgctttggat tggggtcaat   4740
tgcagtccac gtaactggct gcagagaaat ctaccgagca aggaaaaggc acacacacac   4800
gtttgcaggg gtgtctcggt ttgcatttct gttggaatga tccgaactgg actcacatcc   4860
tgtatggtgg atggactgta tattgagggt tccattcttc gcgcagttta gacatctctg   4920
ttttgattct ttgttgttgt ttttatttta aaaggcacaa actctagata ttagttgaat   4980
gttgaggctt taacttttc ggtgtctttc tacaactgtg ttctgtgact caattgtatc   5040
gtgttaatat cagtgcagac tgtctcctct acgtgaccgt ataatgtttt tctcgtcttg   5100
tagtctctat ggcgtgtctt tatggtgtaa taaggttctc acgggtcaa tcttttgtgt   5160 ttagagaggc cacggttcag acaatggtat atatttttgt tatcaggtgc atgtctgtct   5220
gatttctttt tttttcctgt tggactatgt ttgtgaacat aattgtcata agttatgttt   5280
cagatttttg aatttattta tatgtgttat aatgaatgct tctatttaaa agggaaatat   5340
ttctacatgt gcttatagtt ttccaagagt gtaccattaa cttgattgtt gataataaaa   5400
accaaaagca agtctagcaa ttgaactctt cttttttcttg attctttttt tttttttttt   5460
``` tttggttgg tcattgtttt tttttttaa gttttttttt aaaaggat         5508

<210> SEQ ID NO 5
<211> LENGTH: 5493
<212> TYPE: DNA
<213> ORGANISM: Homo sapiens

<400> SEQUENCE: 5

| | |
|---|---|
| cctgagtctc ttgaaagcac atttagctgc aagaagaaat gcaatttata agatgctttc | 60 |
| tctctgtctc tctttgtttt taacccctc taaccaggtg tatttttaaa gaaatccgct | 120 |
| tatcgttcac ataaaccccc ttggcccact tactctatgt tacagggcgc ctgagtcttg | 180 |
| ccaatgtccc agtcctttat aacatttcat gcacttcggg gggtaggctt gttgttaaat | 240 |
| tgagcgtgta acactcttac aaaacaggtt ttctatgaca tcaaggtttc ttctccctaa | 300 |
| ccgagggga aaaaagaag aggacgaaga aggggaaaa cacacacact atctcaattt | 360 |
| atgcctaagg tatatgatca gttaaaaagg cttaaaagct cggggaaatt ggatcaggga | 420 |
| gaatcgtcac ccaactttca ttatttccaa gtagtgtgat tgaattaaag ggcagggagc | 480 |
| tggttagaag ggaggatcag gggctcggtg cgtaatggtg tggtattaaa ttctaattag | 540 |
| agatgcagga atcaatgata gggaggttgg acagctcagt tccccagtgc cagcccaata | 600 |
| gacggatgag ttattgtcat gtaaaaagcg ccagcaataa gaccaaccgc tttgctattg | 660 |
| tccaagtgga aagagccaag tttattatga ggactatatg ctctagagac ctcagacaag | 720 |
| gcatctcata ggaggctttt tcataaaact aggctctgct ggtagtaagg aggccagttt | 780 |
| ggaggcaggc gttgagctgt gcacatctcc ccactccagc caccttctcc atatccatct | 840 |
| tttatttcat tttccactt ggctgagcca tccagaacct tttcaatgta taaaatggaa | 900 |
| tattcttacc tcaattcctc tgcctacgag tcctgtatgg ctgggatgga cacctcgagc | 960 |
| ctggcttcag cctatgctga cttcagttcc tgcagccagg ccagtggctt ccagtataac | 1020 |
| ccgataagga ccacttttgg ggccacgtcc ggctgcccctt ccctcacgcc gggatcctgc | 1080 |
| agcctgggca ccctcaggga ccaccagagc agtccgtacg ccgcaggtta ggaccttcag | 1140 |
| cttttctcagc ggaggaagcc gcctttccgc ccgtatatag gaagccttga ttgcatttga | 1200 |
| aaatggaaat gtgtttagta tttaccaaac gaaatttgct tacacaaatg aaagaattta | 1260 |
| tcacgtttga agcgattgca gggagggta attcacttac agggttacac tatcctagtc | 1320 |
| acacccgaac cgcccacaaa attatcttaa gctgccaaaa tgataggcat aatttattta | 1380 |
| ctttgcgatg agacgtatag cttagaaaat aattgaatta caaagagtaa agctcattac | 1440 |
| tggcagtgtc tctttttta agaaccgaga gcggctcaca cttcttgggc tggtcatttt | 1500 |
| tatgattatt tctttaattt attattattt ttttgcagct ctttccccca acttttgagc | 1560 |
| cgggtcaact ttctgagaat tgaaaagttc ccaaagtggg actgtttggt aacttctttc | 1620 |
| cctggctccc ctgatattcc gactgatgtt ttgggatttt ttcctctct ggttttttcc | 1680 |
| tgctgaaagc actatctcaa gtccgtcaca tcgcgctgtt tcaatccacc caaaggcgct | 1740 |
| tgtgccagaa aggactccgc caagcccgaa gtttgagccc aggtttccgc agataacaaa | 1800 |
| tttcctcggt ttcttcccgc agcttctctc ggcaactctc tcgcgcgggt gtaggtagcg | 1860 |
| gctgccgtat gacctgacct tggagtcctc acattctagc tccacggccg gcgagctgcc | 1920 |
| ggctgatttg ctcactttct gtctcctctg tcatactcta gttccttaca aactcttcac | 1980 |
| ggaccacggc ggcctcaacg agaagcgcaa gcagcggcgc atccgcacca ctttcaccag | 2040 |
| tgcccagctc aaagagctgg aaagggtctt cgcggagact cactacccg acatctacac | 2100 |

```
tcgggaggag ctggccctga agatcgacct cacagaggcg cgagtccagg tacgcgcgcc    2160
tggaaaccga ccccgctccg ccgcactggt ccggggaggt gtggggtgag gggcggctgg    2220
tgaaattcga agtcctggag cctcgagtga aaggaccta gggcccccatg gccgatcaga    2280 aatactggat ttggtgtggc tgtgcgttcg agagaggctt agagcgcacg ctcttggcat    2340
tttatttaca gttgcgaagt gtttcccacc cgagcagaga catggggggc cttgggacgt    2400
ggatgagcga tgcaatttcg gggacaggaa gtgcctgtgg tggaaggtgt gcagactttg    2460
ctcccgtatt ataagttttt ccttctcccc tcccgccccc caaaaaaatg cctcctaact    2520
caagtgcttt taacctggcc ccatggcata taggttcatt ttcccggaaa ctgtgacttg    2580
cattagattt gcaaagggtc tgtgacttca tgaaggtcaa gaaccatgac ttactccaac    2640
ctgttaaaca caggtgcgct cacgagttgg ccacagcgcc tttttgggtg agccccgac    2700 cgagaagcgg tgcgcaccat tgcacgcttt tccaggctca aaggccgggg atgggcagcg    2760
gagcaaaccc agagaggatc ccttttcctt ttaccaatta gagtttaact ttagaactta    2820
ggcttagggg tgaatggcga gctcgggggct tgctcaagaa gccgactgaa cagaggccca    2880
ccaaaataag gccttccctt ttcgggtctt tctgggacct gcggcttttt aaactctgcc    2940
gcaagccttc atgtccctgg cgtgctcact cccctaaga aagtttctcc gaaaatgcac    3000
agcaataaga agcggtagac ttggtggatg tgcgcgcggg ggtgatcaca gcgcatgggg    3060
aggagggtgt taaaacaagc cgaagtagaa cttgggccac cctaaccggt gcttttcttt    3120
cccattttct tctttctccc cctgcttcac cgtctctcct tccgtcttgg gccaggtgtg    3180
gttccagaac cgccgcgcca agtttcgcaa gcaggagcgc gcagcggcag ccgcagcggc    3240
cgcggccaag aacggctcct cgggcaaaaa gtctgactct tccagggacg acgagagcaa    3300
agaggccaag agcactgacc cggacagcac tgggggccca ggtcccaatc ccaaccccac    3360
ccccagctgc ggggcgaatg gaggcggcgg cggcgggccc agcccggctg gagctccggg    3420
ggcggcgggg cccgggggcc cggaggcga acccggcaag ggcggcgcag cagcagcggc    3480
ggcggccgcg gcagcggcag cggcggcagc tggaggcctg gctgcggctg ggggccctgg    3540
acaaggctgg gctcccggcc ccggccccat cacctccatc ccggattcgc ttgggggtcc    3600
cttcggcagc gtcctatctt cgctccaaag acccaacggt gccaaagccg ccttagtgaa    3660
gagcagtatg ttctgatctg gaatcctgcg gcggcggcgg cggcggcgac agcgggcgag    3720
ccagggcccg gcgggcgag tgggcgagcg ggtaggccca aggctattgt cgtcgctgct    3780
gccatggctt tttcattgag ggcctaaagt aatcgcgcta agaataaagg gaaaacggcg    3840
tcgccctcat ttcaacccca ctcctacccc cttcctcaac ccccaaacaa aacaaacaaa    3900
cttccctggc ttcgcacctg cctggggcct cgcagcgggg ccagggctcc gctgctgat    3960 cgggggttgt gagcagcgcg gcctggacgc ggggcactct caggggctg tgtctgcgtg    4020 tcagtttgtg tctgtctcgg ggaatgtgtg tctgtggccc aagcaggtga caggaagaga    4080 tgggggggcct caaccaactt agtgacttgt ttagaaaaaa aagacaaaaa agtaaaata    4140 aaacaaaaa agttggaagg cagaaaccat taaaaaacaa aaagccaaca acccagaaag    4200
gtttaaaaaa cataaggaaa aaaaagacaa attaaaggag gggctagggg agaagctgca    4260
gctggagctg aaggctcgat cttgtgaacc cctaaatccg ctccctccta acagcacgga    4320
ttctcttggg gctcttcttc agggaagagt agggacgccg ttccagcccc ccttcctatc    4380
gtgtccttgg gttcgggtca ctgcggcgac gacttgctca gactgtcccg gcggccggag    4440
```

-continued

```
tgactttctc gcaccccctt gcctgtccca cctcgctgaa caccatcccg ccattagcgc     4500
atcggaaccc cacacagttg caactcccaa ccccgaatct tgcagccgt tcggccctga      4560 aagatgccct atccatgaga tgccttttca tctgcaaact ctgcaaaatg tgtctcatgt     4620
ttcgcaactc tttttttccc cctcgctccc gcctaccccg tcggcatttt cttcttccac     4680
cagcttttac tgaactttt ggcactgctt tggattgggg tcaattgcag tccacgtaac      4740
tggctgcaga gaaatctacc gagcaaggaa aaggcacaca cacacgtttg cagggtgtc     4800 tcggtttgca tttctgttgg aatgatccga actggactca catcctgtat ggtggatgga     4860
ctgtatattg agggttccat tcttcgcgca gtttagacat ctctgttttg attctttgtt     4920
gttgttttta ttttaaaagg cacaaactct agatattagt tgaatgttga ggctttaact     4980
ttttcggtgt ctttctacaa ctgtgttctg tgactcaatt gtatcgtgtt aatatcagtg     5040
cagactgtct cctctacgtg accgtataat gttttctcg tcttgtagtc tctatggcgt     5100
gtctttatgg tgtaataagg ttctcacggg gtcaatcttt tgtgtttaga gaggccacgg     5160
ttcagacaat ggtatatatt tttgttatca ggtgcatgtc tgtctgattt cttttttttt     5220
cctgttggac tatgtttgtg aacataattg tcataagtta tgtttcagat ttttgaattt     5280
atttatatgt gttataatga atgcttctat ttaaaaggga aatatttcta catgtgctta     5340
tagttttcca agagtgtacc attaacttga ttgttgataa taaaaaccaa aagcaagtct     5400
agcaattgaa ctcttctttt tcttgattct tttttttttt tttttttttgg gttggtcatt   5460 gttttttttt tttaagttt tttttaaaag gat                                   5493
```

<210> SEQ ID NO 6
<211> LENGTH: 309
<212> TYPE: PRT
<213> ORGANISM: Homo sapiens

<400> SEQUENCE: 6

```
Met Tyr Lys Met Glu Tyr Ser Tyr Leu Asn Ser Ser Ala Tyr Glu Ser
 1               5                  10                  15

Cys Met Ala Gly Met Asp Thr Ser Ser Leu Ala Ser Ala Tyr Ala Asp
             20                  25                  30

Phe Ser Ser Cys Ser Gln Ala Ser Gly Phe Gln Tyr Asn Pro Ile Arg
         35                  40                  45

Thr Thr Phe Gly Ala Thr Ser Gly Cys Pro Ser Leu Thr Pro Gly Ser
     50                  55                  60

Cys Ser Leu Gly Thr Leu Arg Asp His Gln Ser Ser Pro Tyr Ala Ala
 65                  70                  75                  80

Val Pro Tyr Lys Leu Phe Thr Asp His Gly Gly Leu Asn Glu Lys Arg
                 85                  90                  95

Lys Gln Arg Arg Ile Arg Thr Thr Phe Thr Ser Ala Gln Leu Lys Glu
            100                 105                 110

Leu Glu Arg Val Phe Ala Glu Thr His Tyr Pro Asp Ile Tyr Thr Arg
        115                 120                 125

Glu Glu Leu Ala Leu Lys Ile Asp Leu Thr Glu Ala Arg Val Gln Val
    130                 135                 140

Trp Phe Gln Asn Arg Arg Ala Lys Phe Arg Lys Gln Glu Arg Ala Ala
145                 150                 155                 160

Ala Ala Ala Ala Ala Ala Lys Asn Gly Ser Ser Gly Lys Lys Ser
                165                 170                 175

Asp Ser Ser Arg Asp Asp Glu Ser Lys Glu Ala Lys Ser Thr Asp Pro
            180                 185                 190
```

```
-continued

Asp Ser Thr Gly Gly Pro Gly Pro Asn Pro Asn Pro Thr Pro Ser Cys
    195                 200             205

Gly Ala Asn Gly Gly Gly Gly Gly Pro Ser Pro Ala Gly Ala Pro
    210             215             220

Gly Ala Ala Gly Pro Gly Gly Pro Gly Gly Glu Pro Gly Lys Gly Gly
225             230             235                 240

Ala Ala Ala Ala Ala Ala Ala Ala Ala Ala Ala Ala Ala Ala Ala Gly
                245             250                 255

Gly Leu Ala Ala Ala Gly Gly Pro Gly Gln Gly Trp Ala Pro Gly Pro
            260             265             270

Gly Pro Ile Thr Ser Ile Pro Asp Ser Leu Gly Gly Pro Phe Gly Ser
        275             280             285

Val Leu Ser Ser Leu Gln Arg Pro Asn Gly Ala Lys Ala Ala Leu Val
    290             295             300

Lys Ser Ser Met Phe
305
```